United States Patent [19]
Kimchi

[11] Patent Number: 5,968,816
[45] Date of Patent: Oct. 19, 1999

[54] TUMOR SUPPRESSOR GENES, PROTEINS ENCODED THEREBY AND USE OF SAID GENES AND PROTEINS

[75] Inventor: Adi Kimchi, Reaanana, Israel

[73] Assignee: Yeda Research and Development Company Ltd., Rehovot, Israel

[21] Appl. No.: 08/631,097

[22] Filed: Apr. 12, 1996

Related U.S. Application Data

[63] Continuation-in-part of application No. PCT/US94/11598, Oct. 12, 1994.

[30] Foreign Application Priority Data

Oct. 12, 1993 [IL] Israel ........................................ 107250
Oct. 12, 1994 [WO] WIPO ...................... PCT/US94/11598

[51] Int. Cl.$^6$ .................................................. C12N 15/63
[52] U.S. Cl. ........................ 435/320.1; 435/69.1; 435/7.1; 435/6; 435/325; 435/172.3; 436/63; 514/44; 536/23.1; 536/24.3; 536/24.1
[58] Field of Search ......................... 514/44, 2; 536/23.1, 536/24.3, 24.1; 435/69.1, 7.1, 6, 320.1, 325; 935/52, 55, 66, 77

[56] References Cited

U.S. PATENT DOCUMENTS 5,298,407   3/1994   Anderson et al. ...................... 435/69.1
5,585,479  12/1996   Hoke et al. ............................. 536/24.5

OTHER PUBLICATIONS

Kozopas et al. P.N.A.S 1993, Vol. 90:3516–3520.
Ronald Crystal. Science. 1995, 270:404–409.
Herrman J. Mol. Med. Today. 1995, 73:157–163.
Collins et al. Trend in Biochemical sciences. 1993, Vol. 18, No. 8:307–309.
John Cohen. TibTech. 1995, 13:281–284.
Sinkovics et al. Leukemia. 1994, 8, Suppl. 1, pp. S98–102.
Arai et al. Annu. Rev. Biochem. 1990, 59:783–836.
Hwu et al. J. Immun. May 1993, Vol. 150, 9:4104–4115.
Faust et al. P.N.A.S. 1985, 82:4910–4914.
Coghlan. New Scientist, 1995, Vol. 149, pp. 14–15.
Hirt, Bernhard, "Selective Extraction of Polyoma DNA. . . Cultures", J. Mol. Biol. (1967) 26, 365–369.
Cowburn, David, "Helical Encounter", Structural Biology, Vol. 1, No. 8, Aug. '94.
Kimchi, Adi, "Cytokine Triggered Molecular. . . Arrest", J. of Cellular Biochem., 50:1–9 (1992).
Plentenpol, Jennifer A., et al., "TGF–β1 Inhibition of c–myc . . . Domains", Cell, Vol. 61, 777–785, Jun. '90.
Levy, Naomi, "Complementation by Wild–Type p53 . . . Suppression", Molecular and Cellular Biol., Dec. 1993, 7942–7952, Vol. 13, No. 12.
Deiss, Louis P. et al, "A Genetic Tool Used to Identify . . . Signal", Science, Vol. 252, 117–120, Apr. '91.
Herring, B. Paul, "Domain Characterization . . . Kinase", J. Biol. Chem., 1990, Vol. 265, No. 3, 1724–1730.
Shoemaker, Michael O., et al., "Use of DNA . . . Activity", J. Cell Biol., Vol. 111, Sep. 1990, 1107–1125.
Cruzalegui, Francisco H., et al., "Regulation of Intersteric . . . Kinase", Proc. Natl. Acad. Sci., Vol. 89, pp. 12127–12131, Dec. '92.
Michaely, Peter, "The ANK Repeat . . . Recognition", Trends in Cell Biology, Vol. 2, May 1992, 127–129.
Chan, Timothy A., et al., "Identification of a Gene Encoding . . . Repeats", Oncogene (1994), 9, 1253–1259.
Sen, Soumitra, "Programmed Cell Death . . . Control", Biol. Rev. (1992), 67, pp. 287–319.
Lee, Sooja, et al., "Apoptosis and Signal . . . Mechanism", Current Opinion in Cell Biology, 1993, 5:286–291.
Dowd, Diane R., "Evidence for Early . . . Apoptosis", J. Biol. Chem., Vol. 266, No. 28, Oct. 91, 1843–1846.
Wright, Susan C., et al., "Role of Protein Phosphorylation . . . Variants", J. Cell. Biochem., 53:222–233 (1993).
Matus, Andrew, et al., "Aged–Related Increase . . . Proteins", Biochemistry 1987, 8083–8086.
Faust, Phyllis L. et al., "Cloning and Sequence . . . Cathepsin D", Proc. Natl. Acad. Sci., Vol. 82, 4910–4914, Aug. 1985.
Brendel, Volker et al., "Methods and Algorithms . . . Sequences", Proc. Natl. Acad. Sci., Vol. 89, 2002–2006, Mar. 1992.
Henikoff, Steven et al., "Automated Assembly . . . Searching", Nucleic Acids Research, Vol. 19, No. 23, 6565–6572, 1991.
Shaw, Gray et al., "A Conserved AU . . . Degradation", Cell, Vol. 46, 659–667, Aug. 1986.

*Primary Examiner*—Jasemine C. Chambers
*Assistant Examiner*—Dave Trong Nguyen
*Attorney, Agent, or Firm*—Wigman, Cohen, Leitner & Myers, P.C.

[57] ABSTRACT

The present invention describes the isolation and nucleic acid sequence of genes associated with cyptokine induced cell death. As long as these genes function normally, cytokines induce cell death; once the expression of these genes is inhibited, cytokine induced cell death is inhibited One aspect of the invention comprises expressing or the use of expression vectors to promote cell death in abnormal, pathological, cell growth such as cancer and psoriasis and another aspect of the invention is the protection of cells from programmed cell death in abnormal conditions such as Alzheimer's or Parkinson's disease. The invention can also be used as a screening device for predisportion to cancer or other uncontrolled cell growth diseases.

6 Claims, 23 Drawing Sheets

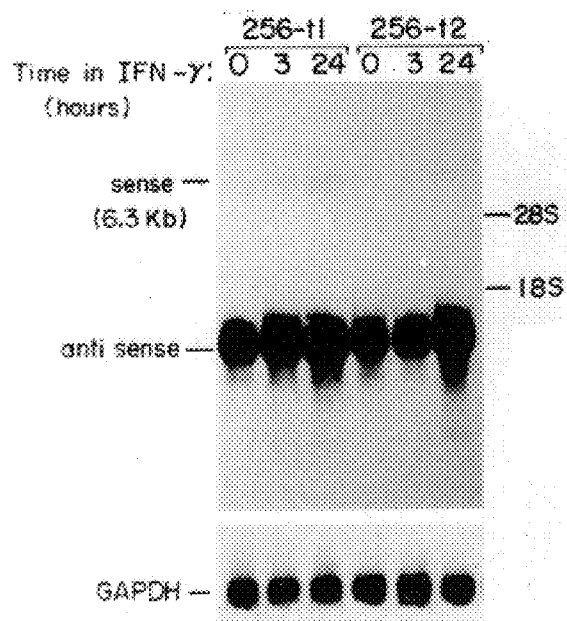
FIG. 2A
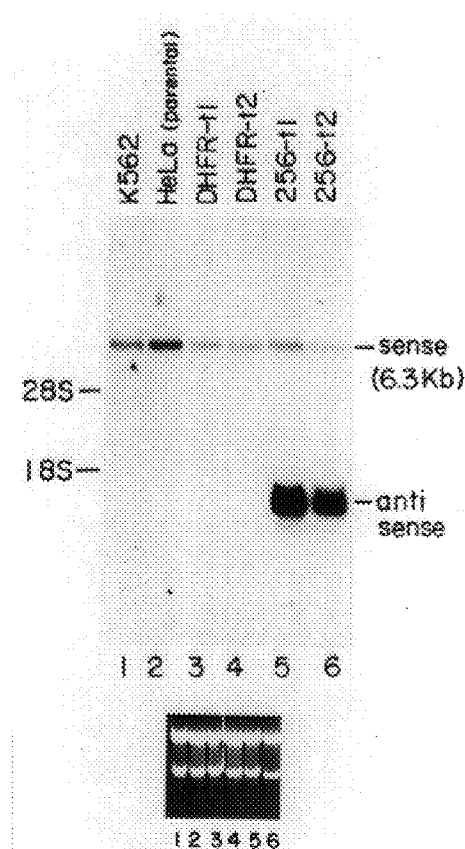
FIG. 2B
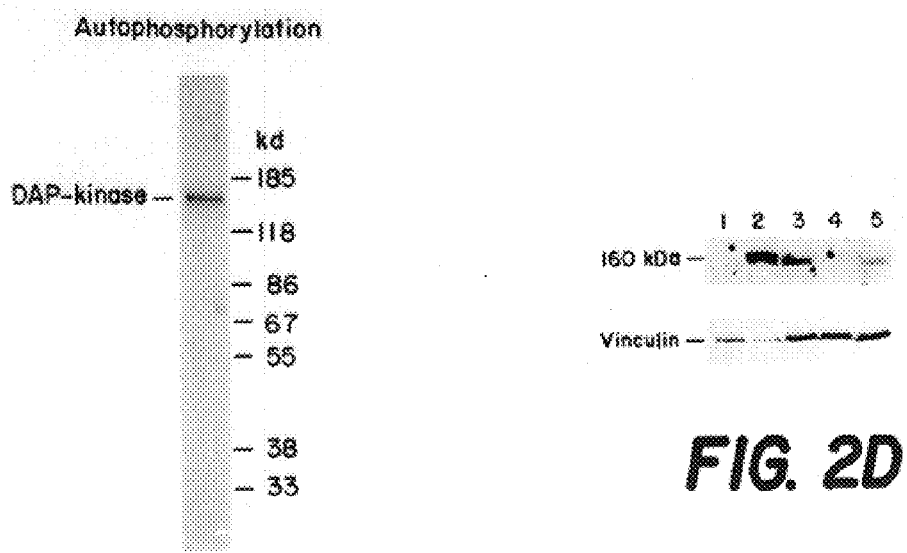
FIG. 2C
FIG. 2D

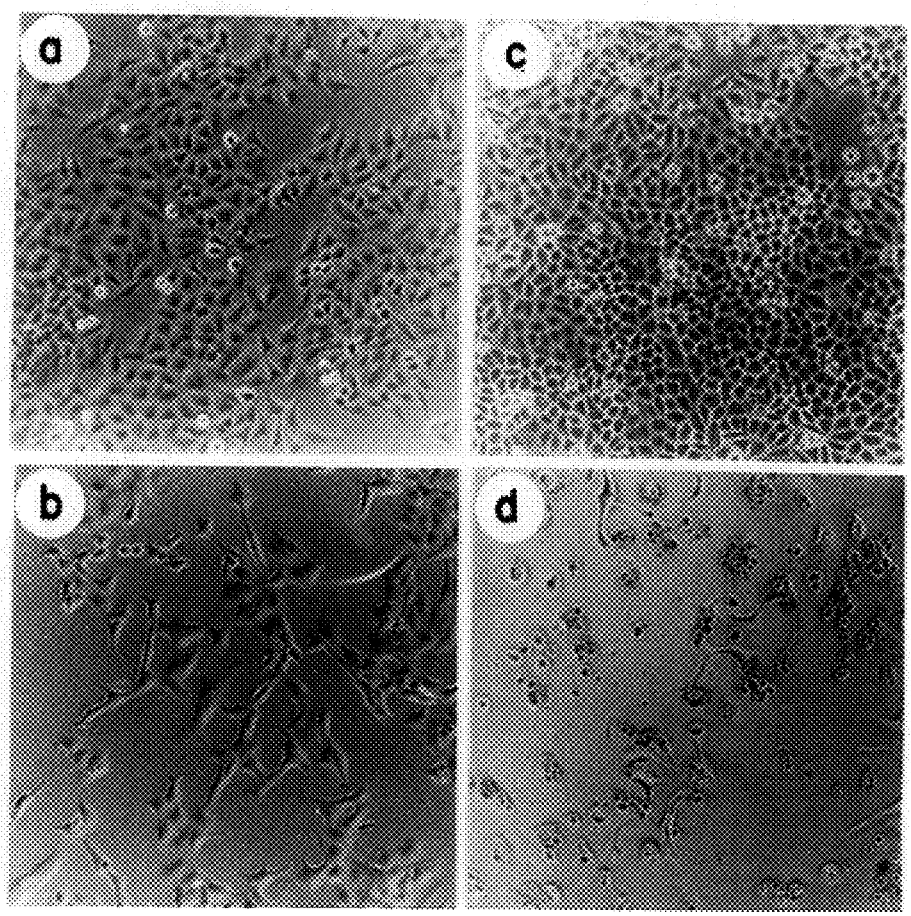

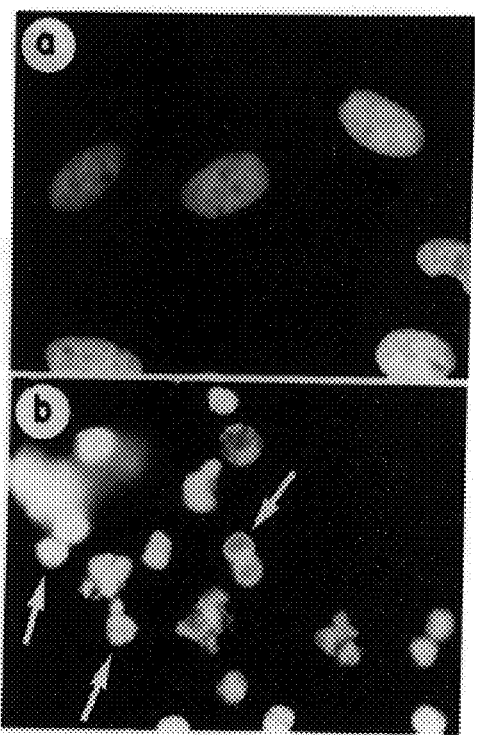
FIG. 3B(a)
FIG. 3B(b)
FIG. 3C(a)  FIG. 3C(c)  FIG. 3C(e)
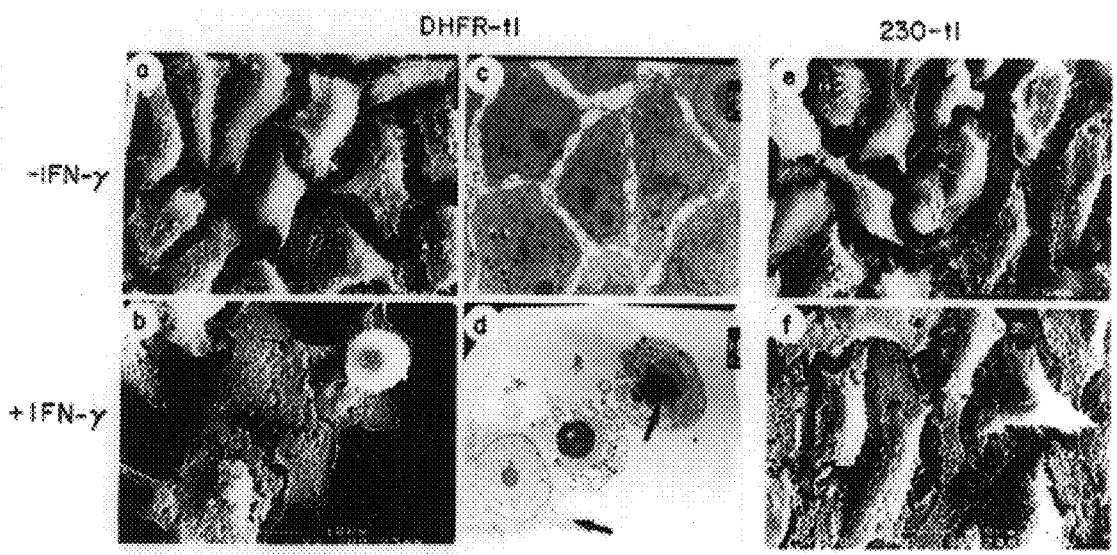
FIG. 3C(b)  FIG. 3C(d)  FIG. 3C(f)

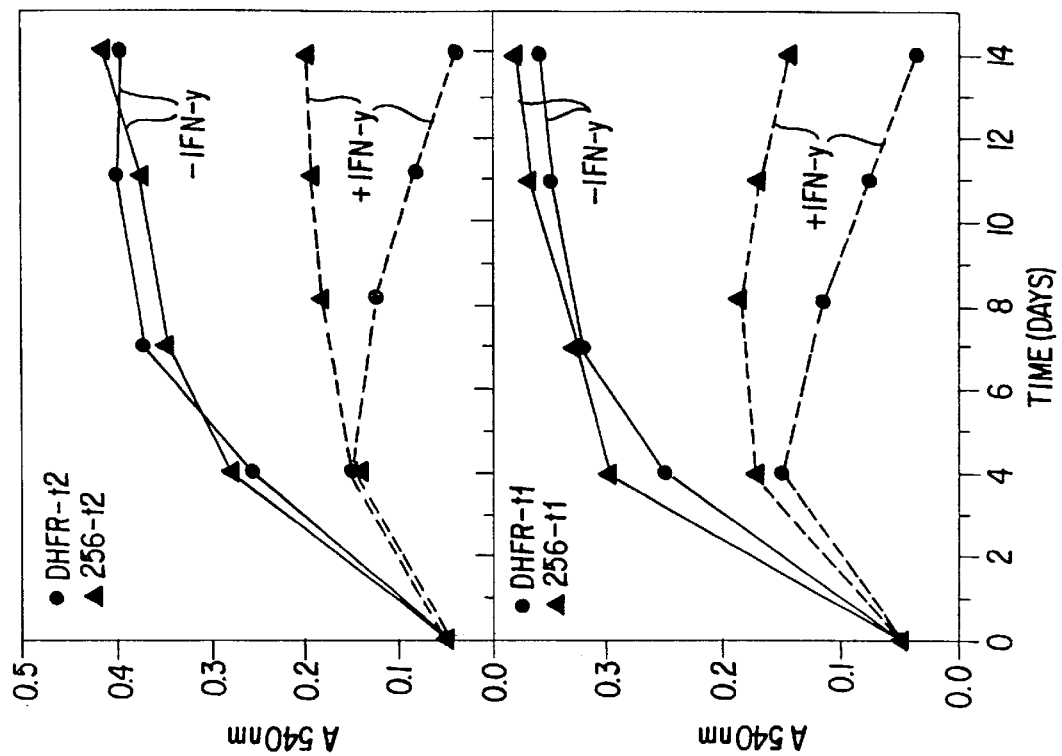
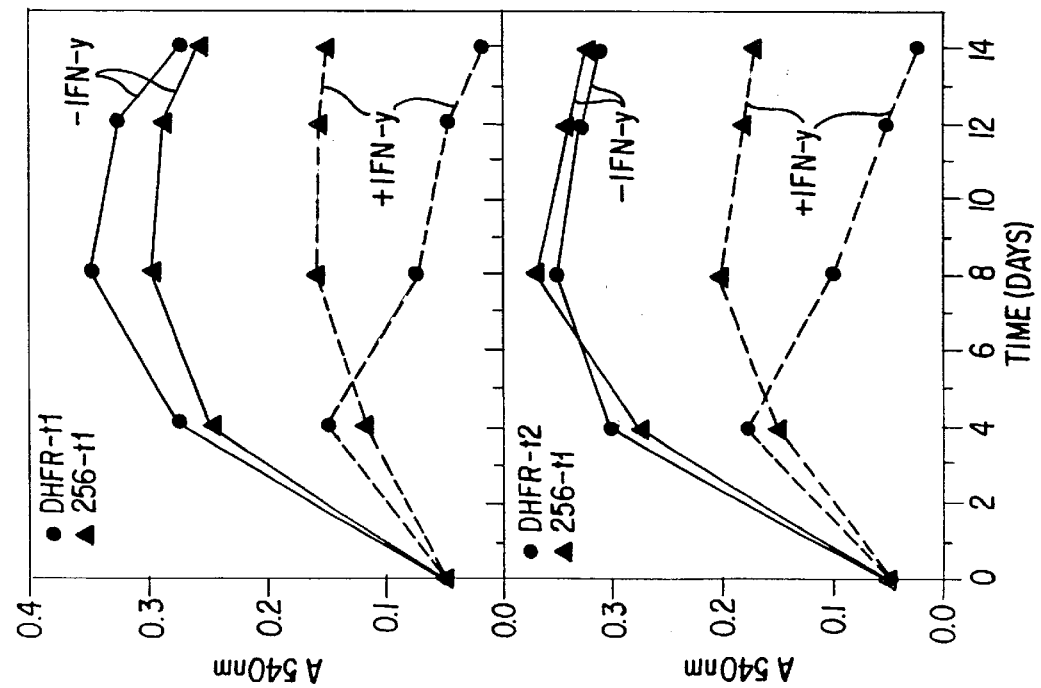
FIG. 4A
FIG. 4B

```
CCTGGTGTGCACAGTTGCTGGGTCATTGTCACTTGGTGTGCATCAGGTTGTCCTCCGATTTTTAGATGAGTTCCTGTCTAGAGATGTC   1530
CTAGTCTGCTCACTGGCTGTGTGGCAGTAGGTACCCTGCTGTCCTTGAAAAGCCAGAGGGTTCACCTAGTCAGACGAAACTCCAGACAGT   1620
GCTTGTGTGGAGGGCCTGACTGTCCTGTCCTCACCACAGCCGATCTGCTGCAGGTCAGTGTGCTGCAGAGGCAGCTGCCAACCACCAGCCT   1710
TTCTGGTGTGTTCTCCAGTTCAGTGTGAGGCAGTTGGTCAGACCTGGTCAGAGACCCAGCAGCCCTCCTCCTGAGGGAGC   1800
ATGGCACAGCCTCACACTTGAAAGACGGTGTTGGTATAAACTGAGGTGGCTTTAGAGACCCAGACTTGGTTGGCAGCGTGCCATGTACCCTTCAAGGCCTGTCA   1890
CCACCTATTTCCTGATCAGTTGGTATAAACTGAGGTGGCTTTAGAGACCCAGACTTGGTTGGCAGCGTGCCATGGAACACCCCAGC   1980
AAGCACCTCCAGCCTGCCTTTCGGACAGCAGCACCCAGGAGGGATGCCGCCTCCAGCAAACACCAGGTCAGGCTGTGCAGACCCCTGCC   2070
CTGCCGCTGCAGAAATCAGCAGCATCCTTAATGCTTCAGTCTTCAGCAGAGGGCTGTATTTCCAGAGGTGCGCTTTTATG   2160
TACTTTTAGCTAGATGGGCATGCATGTGTGAGCTTTAGATCATTAAATCCAAAATGTTTGCCTAAATGAGG   2232
```

FIG. 13

```
CTAGATGAGGCAGATATAAGAGTCA                25
TCCAAAAAAGGACAGAGAGAAAAAAA              50
CAGACAAATCAGTTGTCAGTATCCA                75
TGGCCTCTGATTCTGTCTCAACCAT               100
GAAACAGAAGTGACACATATAC                  122
CTGCTAAAAG
```

FIG. 14

```
        AAC TCA GTC CCT TTC CTT CCA AAA TCT   27
        CCA ACA TGC GGT GCA TTT CCT TAT GAT CAA   54
TTT CTG GGA TTT GTT GAA CTT TCT GCA TAT TGA   81
CCT TGC ATT CTC GAT CTT AAA GTT CTG TTA   108
ACC ATT GCT GAA GAC AAA GTA ATT TAG CTA   135
ACT GCT GAA GAC TGC CAC TTT GTA GGA AGA GAG   162
GAA AAT GGG TGC CAC TGC CTA GTG GTT   189
GAG CTA GTT CTG AAA TGC TCA CCA GCT   216
CTG AAA TGA AAA TGG CAC GAG CTG CAA ACT   243
GTG CTA AAT AGC
```

```
CGGAGGACAGCGGACCGAGCCAACGCCGGGGACTTTGTTCCCTCCACGGAGGGACTCGGCAACTCGGCAGGGAGGGTCTGGGGCCGG    90
CGCCTGGGAGGGGATCTGCGCGCCCACTCACTCCTCGCCCCAGTCTGTGTTCCGGGCCGGCTTCCCGGGCTGTGGCGCTATGGTCG   180
GCCTCCGACAGCGCTCCGGAGGGACCGGGGGAGCTCCAGGCAGTCCCAGGGAGCTCCCAGGCGCCCGGGACTGATGCATGGAGACTGGAGGGCAGGAG   270
                                                                   M  T  V  F  R  Q  E  N    8
CGGTGGTGATGGTCTGGGAAGCGGAGCTGGAGTTGAAGTCCCCCTGGGCTTTGGTGAGGCGTGACAGTTTATCATGACCGTGTTCAGGCAGGAAAAC   360
        ↳ Y  D  T  G  E  E  L  S  G  Q  F  A  V  V  K  K  C  R  E  K  S  T  G  L  Q    38
→ PROTEIN KINASE DOMAIN
GTGGATGATTACTACGACACGGGCGAGGAACTTGGACAGTTTGCGGTTGTGAAGAAAGTGCCGTGAGAAAGTACGGCCTCCAG   450
  Y  P  A  K  F  I  K  K  R  R  T  K  S  R    R  G  V  S  R  E  D  I  E  R  E  V  S  I  L    68
TATCCCGCCAAATTCATCAAGAAAAGGAGGACTAAGTCCAGCCGGGGGGTGAGCCGGGAGGACATCGAGCGGGAGGTCAGCATCCTG   540
  K  E  I  Q  H  P  N  V  I  T  L  H  E  V  Y  E  N  K  T  D  V  I  L  I  L  E  L  V  A  G    98
AAGGAGATCCAGCACCCCAATGTCATCACCCTGCACGAGGTCTATGAGAACAAGACGGACGTCATCCTGATCTTGGAACTCGTTGCAGGT   630
  G  E  L  F  D  F  L  A  E  K  E  S  L  T  E  E  E  A  T  E  F  L  K  Q  I  L  N  G  V  Y   128
GGCGAGCTGTTTGACTTCTTAGCTGAAAAGGAATCTTTAACTGAAGAGGAAGCAACTGAATTTCTCAAACAATTCTTAATGGTGTTAC   720
  Y  L  H  S  L  Q  I  A  H  F  D  L  K  P  E  N  I  M  L  L  D  R  N  V  P  K  P  R  I  K   158
TACCTGCACTCCCTTCAAATCGCCCACTTTGATCTTAAGCCTGAGAACATAATGTCTTTGGATAGAAATGTCCCAAACCTCGGATCAAG   810
  I  I  D  F  G  N  E  F  K  N  I  F  G  T  P  E  F  V  A  P  E  I  V  N  Y  E  P  L  G  L   188
ATCATTGACTTTGGAAATGAATTTAAAAACATATTTGGGACTCCAGAGTTTGTCGCTCCTGAGATAGTCAACTATGAACCTCTTGGTCTT   900
```

FIG. 8A

```
E  A  Q  M  W  S  I  G  V  I  T  Y  I  L  L  S  G  A  S  P  F  L  G  Q  T  K  Q  E  T  L                                  218
GAGGCAGATATGTGGAGTATCGGGGTAATAACCTATATCCTCCTAAGTGGGGCTCCCATTTCTTGGAGACACTAAGCAAGAAACGTTA                                   990

A  N  V  S  A  V  N  Y  E  F  E  D  E  Y  F  S  N  T  S  A  L  A  K  D  F  I  R  R  L  L                                  248
GCAAATGTATCCGCTGTCAACTACGAATTTGAGGATGAATACTTCAGTAATACCAGTGCCCTAGCAAAGATTTCATAAGAAGACTTCTG                                 1080
                                    PROTEIN KINASE DOMAIN ⟶

V  K  D  P  K  K  R  M  T  I  Q  D  S  L  Q  H  P  W  I  K  P  K  D  T  Q  Q  A  L  S  R                                  278
GTCAAGGATCCAAAGAAGAGAATGACAATTCAAGATAGTTTGCAGCATCCCTGGATCAAGCCTAAAGATACAACAGGCACTTAGTAGA                                  1170
                                       CALMODULIN REGULATORY REGION

K  A  S  A  V  N  M  E  K  F  K  F  A  A  R  K  K  W  K  Q  S  V  R  L  I  S  L  C  Q                                     308
AAAGCATCAGCAGTAAACATGGAGAAATTCAAGAAGTTTGCAGCCCGGAAAAAATGGAAACAATCCGTTCGCTTGATATCACTGTGCCAA                                 1260

R  L  S  R  S  F  L  S  R  S  N  M  S  V  A  R  S  D  D  T  L  D  E  E  D  S  F  V  J  M  K                               338
AGATTATCCAGGTCATTCCTGTCCAGAGTAACATGAGTGTTGCCAGAAGTGATGATACTCTGGATGAAGACTCCTTTGTGATGAAA                                    1350

A  I  I  H  A  I  N  D  D  N  V  P  G  L  Q  H  L  L  G  S  L  S  N  Y  D  V  N  Q  P  N                                  368
GCCATCATCCATGCCATCAACGATGACAATGTCCCAGGCCTGCAGCADDTTCTGGGTCTTATTCAACTATGATGTTAACCAACCAAC                                   1440
                                                                             gr1

K  H  G  T  P  P  L  L  I  A  G  C  G  N  I  Q  I  D  L  L  I  K  R  G  S  R  I  D                                        398
AAGCACGGGGACACCTCCATTACTCATTGCTGGCTGTGTGGAATATTCAAATACTACAGTTGCTCATTAAAAGAGGCTCGAGAATCGAT                                 1530
                                                    gr2

V  Q  D  K  G  G  S  N  A  V  Y  W  A  A  R  H  G  H  V  D  T  L  K  F  L  S  E  N  K  C                                  428
GTCCAGGATAAGGGCGGGTCCAATGCCGTCTACTGGGCTGCTCGGCATGGCCACGTCGATACCCTTGAAATTTCTCAGTGAGAACAAATGC                               1620
                                                    gr3

P  L  D  V  K  D  K  S  G  E  M  A  L  H  V  A  A  R  Y  G  H  A  D  V  A  Q  V  T  C  A                                  458
CCTTTGGATGTGAAAGACAAGAGTCTGGAGAGATGGCCCCCTCCACGTGGCAGTGGCTATGGCCATGCTGATGTTGCTCAAGTTACTTGTGCA                              1710
```

```
L  A  S  K  P  T  V  S  V  S  I  N  N  L  Y  P  G  C  E  N  V  S  V  R  S  R  S  M  M  F          758
CTGGCTTCTAAGCCCACAGTCTCAGTGAGCATCAACAACCTGTACCCAGGCTGCGAGAACGTGAGTGTGAGGAGCCGCAGCATGATGTTC         2610

E  P  G  L  T  K  G  M  L  E  V  F  V  A  P  T  H  H  P  H  C  S  A  D  D  Q  S  T  K  A          788
GAGCCGGGTCTTACCAAAGGGATGCTGGAGGTGTTTGTGGCCCCGACTCACCACCCGCACTGCTCGGCTGATGACCAGTCCACCAAGGCC         2700

I  Q  I  N  A  Y  L  N  G  V  G  D  F  S  V  W  E  F  S  G  N  P  V  Y  F  C  Y  D              818
ATCCAGATCAACGCTTATTTGAATGGAGTTGGCGATTTCAGCGTGTGGGAGTTCTCTGGAAATCCTGTGTATTTCTGCTATGAC             2790

Y  F  A  A  N  D  P  T  S  I  H  V  V  F  S  L  E  E  P  Y  E  I  Q  L  N  P  V  I  F          848
TATTTTGCTGCAAATGATCCCACGTCAATCCATGTTGTTTCTTTAGTCTAGAAGAGCCCTATGAGATCCAGCTGAACCCAGTGATTTTC         2880

W  L  S  F  L  K  S  L  V  P  V  E  E  P  I  A  F  G  G  K  L  K  N  P  L  Q  V  L  V          878
TGGCTCAGTTTCCTGAAGTCCCTTGTCCCAGTGGAAGAACCCATAGCCTTCGGTGGCAAGTTGAAGAACCCACTCCAAGTTGTCCTGGTG       2970

A  T  H  A  D  I  M  N  V  P  R  P  A  G  G  E  F  G  Y  Q  K  D  T  S  L  L  K  E  I  R       908
GCCACCCACGCTGACATCATGAATGTTCCTCGACCGGCTGGAGGCGAGTTTGGATATCAGAAAGACACATCGTTGTTGAAAGAGATTAGG       3060

N  R  F  G  N  D  L  H  I  S  N  K  L  F  V  L  D  A  G  A  S  G  S  K  D  M  K  V  L  R       938
AACAGGTTTGGAAATGACCTGCACATTTCAAATAAGCTGTTTGTTCTGGATGCTGGGGCTTCTGGGTCAAAGGACATGAAGGTACTTCGA       3150

N  H  L  Q  E  I  R  S  Q  I  V  S  V  C  P  P  M  T  H  L  C  E  K  I  I  S  T  L  P  S       968
AATCATCTGCAAGAAATACGAAGCCAGATTGTTTCGGTCTGTCCTCCAATGACTCACTTGTGTGAGAAAATCATCTCCACGCTGCCTTCC       3240

W  R  K  L  N  G  P  N  Q  L  M  S  L  Q  D  F  V  Y  D  V  Q  D  L  N  P  L  A  S  E          998
TGGAGGAAGCTCAATGGACCCAACCAGCTGATGTCGCTCCAGGACTTTGTGTACGACGTGCAGGACCTGAACCCCCTGGCCAGCGAG         3330
```

```
  1 GAATTCCGCGGCCCCAGGCAGGCGTGTGTGGTGCGCCTAGGCTGGAGAACTAGTCCTGA   60
 61 CTCAGTGCAAGGATGATGCTGAAAGGAATAACAAGGCTTATCTTGCAAGCATTGTGTCACCT  120
                M  M  L  K  G  I  T  R  L  I  S  R  I  H  K  L
121 GGACCCTGGGCGTTTTTACACATGGGAACCAGGCTGCCAAAGCATTCTGTGCTCACCT     180
     D  P  G  R  F  L  H  M  G  T  Q  A  R  Q  S  I  A  H  L
181 AGATAACCAGGTTCCAGTTGAGAGTCCGAGAGCTATTTCCGACCAATGAGAATGACCC    240
     D  N  Q  V  P  V  E  S  P  R  A  I  S  R  T  N  E  N  D  P
241 GGCCAAGCATGGGGATCAGCAGACGAGGGTCAGCATTCCCTCGCTTTGTGATGCAGGATTTGGA  300
     A  K  H  G  D  Q  H  E  G  Q  H  Y  N  I  S  P  Q  D  L  E
301 GACTGTATTTCCCATGGCCTTCCTCGCTTTGTGATGCAGGTGAAGACATTCAGTGA     360
     T  V  F  P  H  G  L  P  P  R  F  V  M  Q  V  K  T  F  S  E
361 AGCTTGCCTGATGGTAAGGAAACCAGCCTAGAACTTCTGCATTACCTGAAAAACACCAG    420
     A  C  L  M  V  R  K  P  A  L  E  L  L  H  Y  L  K  N  T  S
421 TTTTGCTTATCCAGCTATACGATATCTTCATTTGTGCAAAACAGGACTGGCTGATACTATTCC   480
     F  A  Y  P  A  I  R  Y  L  L  Y  G  E  K  G  T  G  K  T  L
481 AAGTCTTTGCCATGTTATTCATTTTGGGTGAAAAATTGTCGGGATCTTCTGCAGTCCAACAAACA  540
     S  L  C  H  V  I  H  F  C  A  K  D  W  L  I  L  H  I  P
541 AGATGCTCATCTTTGGGTGAAAAATTGTCGGGATCTTCTGCAGTCCAGCTACAACAAACA    600
     D  A  H  L  W  V  K  N  C  R  D  L  L  Q  S  S  Y  N  K  Q
601 GCGCTTTGATCAACTTAGAGGCTTCAACTGGCTGAAGAATTTCAAAACTACAAATGA     660
     R  F  D  Q  L  E  A  S  T  W  L  K  N  F  K  T  T  N  E
661 GCGCTTCCTGAACCAGATAAAAGTTCAAGAGAAGTATGTCTGGAATAAGAGAAAGCAC    720
     R  F  L  N  Q  I  K  V  Q  E  K  Y  V  W  N  K  R  E  S  T
721 TGAGAAAGGGAGTCCTCTGGAGAAGTGGTTGAACAGGGCATAACAGGGTGAGGAACGC    780
     E  K  G  S  P  L  G  E  V  E  Q  G  I  T  R  V  R  N  A
781 CACAGATGCAGTTGGCATTGTGCTGAAGAGCTAAAGAGGCAAAGTTCTTTGGGTATGTT   840
     T  D  A  V  G  I  V  L  K  E  L  K  R  Q  S  S  L  G  M  F
841 TCACCTCCTAGTGGCCGTGGATGGAATCAATGCTCTTTGGGGAAGAACCACTCTGAAAAG   900
     H  L  L  V  A  V  D  G  I  N  A  L  W  G  R  T  T  L  K  R
901 AGAAGATAAAAAGCCCGATTGCCCCGAGGAATTAGCACTTGTTCACAACTTGAGGAAAAT   960
```

```
                                                               M  Q  P
  1  GGCTATAAGGCAGGCTTCGGGAGCCTTCTCCGACCCTCGGCGCCGGCCATGCAGCCC    60
     S  S  L  L  P  L  A  L  C  L  L  L  A  A  P  A  S  A  L  V  R
 61  TCCAGCTTTCTGCCGCTTGCCCTGTGCCTTCTGCTGGCTGCACCCGCCTCGGCTGTCAGG  120
     I  P  L  H  K  F  T  S  I  R  R  T  M  S  E  V  G  G  S  V
121  ATCCCGCTGCACAAGTTCACGTCCATCCGGAGGACCATGTCGGAGGTTGGGGGCTCTGTG  180
     E  D  L  I  A  K  G  P  V  S  K  Y  S  Q  A  V  P  A  V  T
181  GAGGACCTGATTGCCAAAGGCCCCGTCTCAAGTACTCCCAGGCAGTGCCAGCCGTGACC   240
     E  G  P  I  P  E  V  L  K  N  Y  M  D  A  Q  Y  Y  G  E  I
241  GAGGGGCCCATTCCGGAGGTGCTCAAGAACTACATGGACGCCCAGTACTACGGGGAGATT  300
     G  I  G  T  P  P  Q  L  F  T  V  V  F  D  T  G  S  S  N  L
301  GGCATCGGGACGCCCCCCCAGTGCTTCACAGTGGTCTTTGACACGGGCTCCTCAAACCTG  360
     W  V  P  S  I  H  C  K  L  L  D  I  A  C  W  I  H  H  K  Y
361  TGGGTCCCCTCCATCCACTGCAAACTGCTGGACATCGCTTGTTGGATCCACCACAAGTAC  420
     N  S  D  K  S  S  T  Y  V  K  N  G  T  S  F  D  I  H  Y  G
421  AACAGCGACAAGTCCAGCACCTACGTGAAGAATGGTACCTCGTTTGACATCCACTATGGC  480
     S  G  S  L  S  G  Y  L  S  Q  D  T  V  S  V  P  C  Q  S  A
481  TCGGGCAGCCTCTCCGGCTACCTGAGCCAGGACACTGTGTCGGTGCCCTGCCAGTCAGCG  540
     S  S  A  S  A  L  G  G  V  K  V  E  R  Q  V  F  G  E  A  T
541  TCGTCAGCCTCTGCCCTGGGGGTGAAAGTGGAGAGGCAGGTCTTTGGGGAGGCCACC     600
     K  Q  P  G  I  T  F  I  A  A  K  F  D  G  I  L  G  M  A  Y
601  AAGCAGCCAGGCATCACCTTCATCGCAGCCAAGTTCGATGGCATCCTGGGCATGGCCTAC  660
     P  R  I  S  V  N  N  V  L  P  V  F  D  N  L  M  Q  Q  K  L
661  CCCCGCATCTCCGTCAACAACGTGCTGCCTGTCTTTGACAACCTGATGCAGCAGAAGCTG  720
     V  D  Q  N  I  F  S  F  Y  L  S  R  D  P  D  A  Q  P  G  G
721  GTGGACCAGAACATCTTCTCCTTCTACCTGAGCAGGGACCCAGATGCGCAGCCTGGGGGT  780
     E  L  M  L  G  G  T  D  S  K  Y  Y  K  G  S  L  S  Y  L  N
781  GAGCTGATGCTGGGTGGCACAGACTCCAAGTATTACAAGGGTTCTCTGTCCTACCTGAAT  840
```

FIG. 15A

```
     V  T  R  K  A  Y  W  Q  V  H  L  D  Q  V  E  V  A  S  G  L
841  GTCACCCGCAAGGCCTACTGGCAGGTCCACCTGGACCAGGTGGAGGTGGCCAGCGGGCTG   900
      T  L  C  K  E  G  C  E  A  I  V  D  T  G  T  S  L  M  V  G
901  ACCCTGTGCAAGGAGGGCTGTGAGGCCATTGTGGACACAGGCACTTCCCTCATGGTGGGC   960
      P  V  D  E  V  R  E  L  Q  K  A  I  G  A  V  P  L  I  Q  G
961  CCGGTGGATGAGGTGCGCGAGCTGCAGAAGGCCATCGGGGCTGTGCCGCTGATTCAGGGC  1020
      E  Y  M  I  P  C  E  K  V  S  T  L  P  A  I  T  L  K  L  G
1021 GAGTACATGATCCCTGTCAGAAAGGTGTCCACCCTGCCGGATCACACTGAAGCTGGGA   1080
      G  K  G  Y  K  L  S  P  E  D  Y  T  L  K  V  S  Q  A  G  K
1081 GGCAAAGGCTACAAGCTGTCCCCAGAGGACTACACTCTCAAGGTGTCCCAGGCCGGGAAG  1140
      T  L  L  S  G  F  M  G  M  D  I  P  P  P  S  G  P  L  W
1141 ACCCTCTGCTGAGCGGCTTCATGGGCATGGACATCCCGCCACCCAGCGGGCCACTCTGG  1200
      I  L  G  D  V  F  I  G  R  Y  Y  T  V  F  D  R  D  N  N  R
1201 ATCCTGGGGGACGTCTTCATCGGCCGCTACTACACTGTGTTTGACCGTGACAACAACAGG  1260
      V  G  F  A  E  A  A  R  L  *
1261 GTGGGCTTCGCTGAGGCTGCCGAGCCTCTAGTTCCCAAGGGTCCGCGCGCCAGCACAGAA  1320
1321 ACAGAGGAGAGTCCCAGAGCAGGAGAGGCCCTGGGGCCTGGAGCCCCTCCACACACACCA  1380
1381 CACACTGCCCGCCACTGTCCTGGGCCTGGAAGCCGGCTGCCTGCTGCTCTCCGACTTGC  1440
1441 TGTTTGTTCGTGTTTCCCCCTGGTTCAGAGCTGATCCAGAGCACAGATGCCTGTCTGTCTC  1500
1501 TCCATCTGTTTGGTGGGGTAGAGCTGATCCAGAGCTGAGCTGTTGTGTCATTGGAA    1560
1561 GACCCCACCCAAGCTTGGTGGGGCTTGGCAGCAGCCTGTATCCTGGGCTCCTTCCAGG    1620
1621 AGTCCTCCGGCCCTCCCTGGAGCCTGACCTGCTGAGGCCCCTACCCACACCAGGCCG    1680
1681 TCCTCCCGGCCCTCCCTTGGAAACCTGTCACCCTGTTCAGTGTCCCGGGCCCCAGCTTGGG  1740
1741 CCCAGCTGGGCCTCTGCACCTGTAGAGGGACACAAAACCACTTGTTGGAG       1800
1801 GACCCCAAGCTGGGGGACTGAGCCAGTCCAGGGGCATGTATTGGCCTGTGACCTCTGTCT  1860
1861 CTGCAGGCTGGTGCTGGGACTGAGCCAGTCCAGGGGCATGTATTGGCCTGTGACCTCTGTCT  1920
1921 TTGGGATTGGGGCTGGTGCCAGCCTTCCTGCAGCTGACTGACCTCTGTGTCCTGTTG   1980
1981 GGCGGCTGAGAGCCCCAGTGTTGGCCTTGGCCTTCCGGCCTCCCTC   2038
```

FIG. 15B

TUMOR SUPPRESSOR GENES, PROTEINS ENCODED THEREBY AND USE OF SAID GENES AND PROTEINS

This is a continuation-in-part of International Application PCT/US94/11598, with an international filing date of Oct. 12, 1994 which designated the United States.

FIELD OF THE INVENTION

The present invention relates to the field of tumor-suppressor genes in general, and programmed cell death in particular.

BACKGROUND OF THE INVENTION

One of the factors which determines the proliferation state of cells is the balance between the growth-promoting effects of proto-oncogenes, and the growth-constraining effects of tumor-suppressor genes.

One mechanism by which these tumor-suppressor genes exert their growth-constraining effect is by inducing the cell to undergo a physiological type of death. Such a controlled cell death is evident in a multitude of physiological conditions including metamorphosis, synaptogenesis of neurons, death of lymphocytes during receptor repertoire selection, controlled homeostasis in the bone-marrow and other proliferative tissues, and others. Such cell death is regulated by the interaction of the cell with other cells or with cell products, for example through the activity of suitable cytokines.

Genetic mutation that inactivates the suppressor genes, liberate the cell from normal growth constraint imposed by other cells, resulting in an uncontrolled growth of the cell without any relation to external signals. This uncontrolled growth is a step in tumorigenesis.

To date, only a few tumor-suppressor genes have been fully characterized including the retinoblastoma (Rb) gene, p53, DCC, NM23 WT-1, NF-1, APC, and ras suppressor genes. A mutation in either of the above genes, probably in both alleles, which leads to either blockage of expression, or production of a faulty protein, hampers the normal control of growth and viability of cells and may thus give rise to cancer.

Growth-inhibiting cytokines have a double effect on the target cell. They can either inhibit the proliferation of the cell, and/or give rise to cell death. To date, blockage or activation of expression of known tumor-suppressor genes was shown to counteract or enhance, respectively, cytokines' inhibition of cells' growth (reviewed by A. Kimchi, 1992, J. Cell Biochem., 50: 1–9) but did not have any effect on the death promoting action of cytokines. For example, the growth inhibitory response to cytokines such as TGF-β, was markedly reduced by the inactivation of the Rb gene, or the response to IL-6 was enhanced by introducing activated p53 genes (Pietenpol et al., 1990, Cell, 61:777–785; Levy et al., 1993, Mol. Cell. Biol., 13:7942–7952).

Thioredoxin, a small hydrogen carrier protein, has previously been implicated in the IFN-γ-mediated growth arrest of HeLa cells (Deiss, L. P. and Kimchi, A. (1991) Science 234:117–120).

SUMMARY OF THE INVENTION

In the following, the term "programmed cell death" will be used to denote a physiological type of cell death which results from activation of some cellular mechanisms, i.e. death which is controlled by the cell's machinery. Programmed cell death may, for example, be the result of activation of the cell machinery by an external trigger, e.g. a cytokine, which leads to cell death.

The present invention is based on the pioneering finding that inhibition of expression of certain genes counteracts the cytokine-induced cell death. Namely, as long as these genes function normally, cytokine induces cell death; once the expression of said genes is inhibited, the cytokine-induced cell death is inhibited. It follows therefrom that the normal expression product of these genes is involved in programmed cell death, especially in cytokine-induced cell death. In HeLa cells, IFN-γ induces a biphasic process, which comprises an initial cytostatic phase and a subsequent cytotoxic phase (programmed cell death). The novel genes discovered in accordance with the present invention were found to affect only the later, cytotoxic phase. These genes will be referred to herein as "DAP (death-associated protein) genes". DNA molecules comprising a coding sequence encoding the expression products of the DAP genes, or expression products having a similar biological activity, will be referred to herein at times collectively as "DAP DNA molecules". The expression products of the DAP DNA molecules will be referred to herein at times collectively as "DAP products".

According to one aspect of the present invention, to be referred to herein as "the death-promoting aspect", the above DAP DNA molecules, expression vectors comprising them, or DAP products are used for promoting death of normal or tumor cells. A particular application of the death-promoting aspect is in therapy of diseases or disorders associated with uncontrolled, pathological cell growth, e.g. cancer, psoriasis, and others. The use of DAP DNA molecules in gene therapy or DAP products if produced extracellularly, in accordance with the death-promoting aspect of the invention, may be in conjunction with cytokines, e.g. IFN-γ.

According to another aspect of the invention, to be referred to herein as "the death-preventing aspect", agents which prevent the expression of said DAP DNA molecules, or agents which antagonize, inhibit or neutralize the DAP products, are used for protecting cells from programmed cell death. Examples of possible applications of the death preventing aspect of the invention are in prevention of cell death in various degenerative neurological diseases, such as Alzheimer's disease or Parkinson's disease, which are associated with premature death of particular subsets of neurons; prevention of death of T-cells in AIDS patients, which death resembles programmed cell death; prevention of rejection-associated cell death in transplants which is believed to result, at least in part, from programmed cell death; protection of normal cells from the cytotoxic effects of certain anti-cancer therapies; etc.

According to a further aspect of the present invention, referred to herein at times as "the screening aspect", DAP DNA molecules are used in order to screen individuals for predisposition to cancer. In accordance with this aspect, the screening is carried out by comparing the sequence of each of the DAP DNA molecules to each of the respective DAP genes in the individual. The absence of a DAP gene, a partial deletion or any other difference in the sequence that indicates a mutation in an essential region, may result in a loss of function and as a consequence a predisposition for cancer. For screening, preferably a battery of different DAP genes may be used.

The DAP genes seem to play an important role in programmed cell death and the inhibition of their expression or neutralization of their expression products protects the cell from cytokine-promoted cell death. Examples of such genes are those whose sequences are depicted in FIGS. 6, 8, 12 and 16 or whose partial sequences are depicted in FIG. 13. The gene for the known protease cathepsin D, whose sequence is depicted in FIG. 15, is also revealed here for the first time as functioning as a DAP gene.

DAP DNA molecules useful in the death-promoting aspect of the invention may have the nucleic acid sequence of the DAP gene or other sequences which encode a product having a similar biological activity to that of the DAP product. Such DAP molecules include DNA molecules having a sequence other than that of the DAP gene but which, owing to the degenerative nature of the genetic code, encode the same protein or polypeptide as that encoded by the DAP gene.

It is well known that it is possible at times to modify a protein by replacing or deleting certain amino acids which are not essential for a certain biological function, or adding amino acids in a region which is not essential for the protein's biological function, without such modification essentially affecting the biological activity of the protein. Thus, a DAP DNA molecule useful in the death promoting aspect of the invention may also have a modified sequence encoding such a modified protein. The modified sequence has a sequence derived from that of the DAP gene or from that of the above degenerative sequence, in which one or more nucleic acid triplets (in the open reading frame of the sequence), has been added, deleted or replaced, with the protein product encoded thereby retaining the essential biological properties of the DAP product. Furthermore, it is known that at times, fragments of proteins retain the essential biological properties of the parent, unfragmented protein, and accordingly, a DAP DNA molecule useful in the death promoting aspect of the invention may also have a sequence encoding such fragments.

A DNA molecule useful in the death-preventing aspect of the invention may have a sequence which is an antisense sequence to that of the DAP gene, or an antisense sequence to part of the DAP gene, blocking of which is sufficient to inhibit expression of the DAP gene. The part of the gene can be either the coding or the non-coding part of the DAP gene. The mRNA transcripts of the antisense sequences hybridize to the mRNA transcripts of the DAP gene and interfere with the final protein expression. Another DNA molecule useful in the death preventing aspect of the invention is a DNA molecule coding for a modified DAP product which is capable of inhibiting the activities of the unmodified DAP product in a dominant negative manner, such as catalytically inactive kinase (DAP-kinase) or any other modified protein whose presence in the cell interferes with the normal activity of the native protein, for example by producing faulty hetero dimers comprised of modified and unmodified proteins which are inactive and the like.

DNA molecules useful in the screening aspect of the invention comprise the sequence of a DAP gene or a sequence of a fragment thereof. Additionally, also the above antisense DNA sequences may be used in the screening aspect of the invention.

The present invention thus provides a DNA molecule comprising a sequence selected from the group consisting of:

(a) a gene whose expression is necessary for the mediation of the cytokine-induced programmed cell death;

(b) a DNA sequence encoding the same protein or polypeptide encoded by the gene defined in (a);

(c) a modified DNA sequence of (a) or (b) in which one or more nucleic acid triplets has been added, deleted, or replaced, the protein or polypeptide encoded by the modified DNA sequence mediating the cytokine-induced programmed cell death similarly to the protein or polypeptide encoded by the gene as defined under (a) or (b);

(d) fragments of any of the DNA sequences of (a), (b) or (c), encoding a protein or a polypeptide having said biological activity;

(e) a sequence which is an antisense to the entire or part of the DNA molecule under (a) and capable of inhibiting the expression of said gene; and (f) a modified DNA sequence of (a) or (b) in which one or more nucleic acid triplets has been added, deleted or replaced, the protein or polypeptide encoded by the modified sequence having dominant negative effect manifested by the ability of said protein or polypeptide to inhibit said cytokine-induced programmed cell death.

In accordance with a specific embodiment, the present invention provides a DNA molecule comprising a nucleic acid sequence selected from the group consisting of:

(a) A DNA molecule comprising a nucleic acid sequence expressed in cells, the expression product of which is involved in cytokine-induced programmed cell death, being one of the following:

(i) a DNA sequence comprising a coding sequence beginning at the nucleic acid triplet at position 160–162 and ending at the triplet 466–468 of the sequence depicted in FIG. 6 (SEQ ID NO: 1);

(ii) a DNA sequence comprising a coding sequence beginning at nucleic acid triplet at position 287–289 and ending at a triplet at positions 816–818 of the sequence depicted in FIG. 6 (SEQ ID NO: 2);

(iii) a DNA sequence comprising a coding sequence beginning at nucleic acid triplet at position 337–339 and ending at the triplet at position 4603–4605 of the sequence depicted in FIG. 8 (SEQ ID NO: 3);

(iv) a DNA sequence comprising a coding sequence beginning at position 74–76 and ending at position 1268–1270 of the sequence depicted in FIG. 12 (SEQ ID NO: 4);

(v) a DNA sequence comprising a sequence depicted in FIG. 13 (SEQ ID NO: 5); and (vi) a DNA sequence comprising a coding sequence beginning at the nucleic acid triplet at position 201–203 and ending at the triplet 3018–3020 of the sequence depicted in FIG. 15A–15B;

(b) a DNA molecule encoding the same protein or polypeptide encoded by any one of the DNA sequences of (a);

(c) a DNA molecule as in (a) or (b) in which one or more nucleic acid triplets has been added, deleted or replaced, the protein or polypeptide encoded by the sequence having essentially the same biological activity as that encoded by any one of the DNA molecules of either of claims (a) or (b), respectively;

(d) a fragment of any one of the DNA molecules of (a)–(c) encoding a protein or polypeptide retaining a biological activity present in the protein or polypeptide encoded by any one of the DNA molecules of either of claims (a) or (b) with the proviso that nucleotide sequence 2556–2814 of FIG. 8 and sequence 2221–2290 of FIG. 15A–15B are excluded;

(e) a molecule which comprises an antisense sequence complementary in sequence to the mRNA transcribed from the entire or part of any one of the DNA molecules according to (a) or (b) or of the cathepsin D gene in FIG. 15 and capable of inhibiting the expression of said sequences; and (f) a modified DNA sequence of any one of the sequences in (a) in which one or more nucleic acid triplets has been added, deleted or replaced, the protein or polypeptide encoded by the modified sequence having dominant negative effect and being capable of inhibiting the function of the protein or polypeptide encoded by any one of the sequences in (a).

The preferred antisense sequences as defined in (e) above are those to the sequences beginning at position 1000 and ending at position 1320 of the DAP-1 gene in FIG. 6, 3781–4148 of the DAP-2 gene in FIG. 8, 74–1270 of the DAP-3 gene in FIG. 12, and 1203–1573 of the cathepsin D gene in FIG. 15 (SEQ ID NO: 7).

The present invention also provides a vector comprising any of the above DNA molecules, the vector comprising also sequences required for maintaining and replicating it in a host cell. Vectors in accordance with the present invention may be transfer vectors for propagating and replicating the DNA sequences in a host cell or may be expression vectors comprising also sequences required for translation of said DNA sequences into an mRNA. Examples of such expression vectors are plasmids, e.g. episomes or viruses. Examples of episomes are those constructed by using the vehicles pTKO1, pTKO2 and pTKO3 (Deiss and Kimchi, supra).

The present invention also provides a DAP product which is a protein or polypeptide encoded by a DNA molecule of the invention, with the exception of the DNA molecules having an antisense sequence, or such a protein or polypeptide which has been chemically modified, for example, by methylation, glycosylation, etc. An example of a DAP product is that having the amino acid sequence depicted in FIGS. 6, 8 and 12. The DAP product is useful in the death-promoting aspect of the present invention. In accordance with this aspect, the protein may be administered to patients, in particular, to cancer patients, which administration may cause death of the transformed cells.

The present invention further provides agents which inhibit, antagonize or neutralize the DAP product, which are useful in the death-preventing aspect of the invention. Such agents are for example, antibodies directed against the DAP product; inhibitors or antagonists of the DAP product which are able to counteract their effect and prevent the death-promoting activity of the DAP product.

The present invention further provides a pharmaceutical composition comprising a pharmaceutically acceptable carrier and an active agent being selected from the group consisting of: (i) an expression vector comprising a DNA molecule of the invention or a DNA molecule coding for cathepsin D; (ii) a DAP product of the invention or cathepsin D; and (iii) an antibody, inhibitor or antagonist to the DAP product. The pharmaceutical composition of the present invention may also comprise means for targeting said active agent to the desired cell or tissue. Depending on the nature of the active agent, the composition is useful either in accordance with the death-promoting or the death-preventing aspect of the invention. In accordance with the death-promoting aspect of the invention, the pharmaceutical composition may also comprise a cytokine, e.g. IFN-γ, in combination with a suitable DAP product, or with an expression vector comprising a suitable DAP molecule.

Further provided by the present invention is a method of treatment comprising administering said active agent to an individual. Similarly as in the pharmaceutical composition, depending on the nature of said active agent, the method is practisable in either the death-promoting aspect of the invention or the death-preventing aspect of the invention. In the death-promoting aspect of the invention, said active agent may be administered in conjunction with a cytokine, e.g. IFN-γ.

In accordance with the screening aspect of the invention, there is provided a method for detecting the absence of the DAP gene, a partial deletion or a mutation (i.e. point mutation, deletion or any other mutation) in the DAP genes of an individual, comprising probing genomic DNA or cDNA from the individual with a DNA probe or a multitude of DNA probes having a complete or partial sequence of the DAP genes or having a sequence which is an antisense to the complete or partial sequence of the DAP gene. A particular application of the screening aspect of the invention is in the screening for individuals having a predisposition to cancer, an absence of the gene or a detected mutation or deletion indicating that the individual has such predisposition. The method in accordance with the screening aspect typically comprises the following steps:

(a) obtaining a sample of either genomic DNA from cells of the individual or cDNA produced from mRNA of said cells;

(b) adding one or more DNA probes each of said probes comprising a complete or partial sequence of a DAP gene, or a sequence which is an antisense sequence to the complete or partial sequence of the DAP gene;

(c) providing conditions for hybridization between the DNA probe or probes and the DNA of said sample;

(d) on the basis of the hybridization determining whether the DAP gene is absent or there is a match between the sequence of the DNA probe or probes and a sequence in the DNA of said sample or a mismatch, a mismatch indicating a deletion or a mutation in the genomic DNA and a predisposition to cancer in the tested individual.

A specific embodiment of the screening aspect of the invention involves use of a complete or partial sequence of that shown in FIGS. 6, 8, 12, 13, 14 or 15A–15B, or an antisense of the complete or partial sequence in FIGS. 6, 8, 12, 13, 14 or 15A–15B.

The mutation in the DAP gene indicating a possible predisposition to cancer can also be detected by the aid of appropriate antibodies which are able to distinguish between a mutated and non-functional and a normal functional DAP gene product.

DESCRIPTION OF THE DRAWINGS

FIGS. 1A–D show RNA and protein expression of the DAP-1 gene, wherein:

FIG. 1(A) shows a Northern blot analysis of sense and antisense mRNA obtained from HeLa cells transfected with the constructs 230, 255, 260, 259 and control cells (parental cells) and probed by labeled cDNA fragments from construct 230. Total RNA was prepared from HeLa cells either before (parental) or after transfection with pTKO1 constructs #230 or #255 (group 1), #260 (group 5) and #259 (group 3) designated 230-t1, 255-t1, 260-t1 and 259-t1, respectively. Twenty μg RNA were processed on Northern blots and DNA fragment #230 was used as a probe. The arrows point to the position of sense and antisense RNAs.

FIG. 1(B) shows a Northern blot analysis of sense and antisense mRNA obtained from HeLa cells transfected with control construct (DHFR-t2), 230 construct or control cells (parental) cells treated with (+) or without (−) 750 U/ml of IFN-γ for 24 h. The RNA was extracted from the indicated HeLa cells which were grown for 4 days in the absence (−)

or presence (+) of IFN-γ (750 U/ml). The Northern blot containing 20 μg RNA samples was hybridized with the cDNA insert of λ1 phage. The Ethidium Bromide staining of the mRNA samples is shown.

Figure 1A:
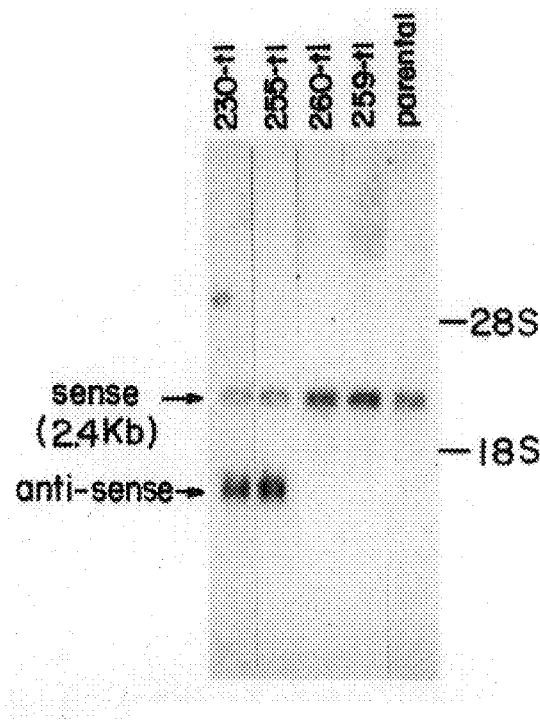
Figure 1B:
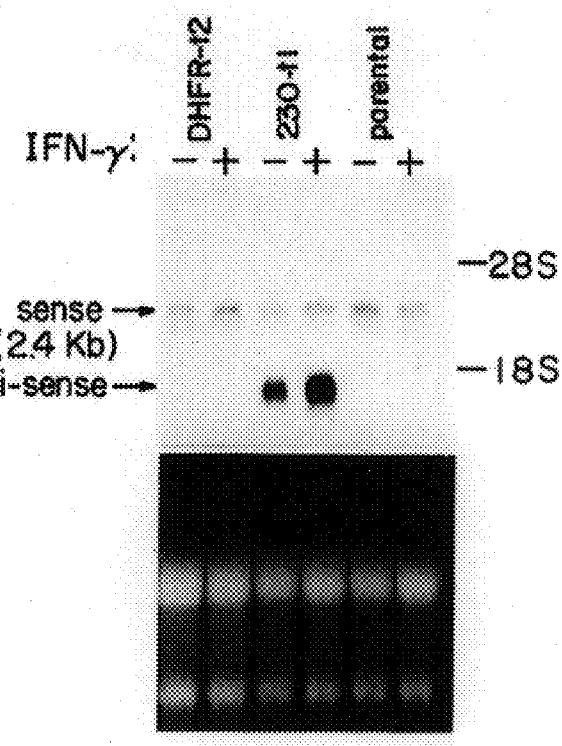
Figure 1C:
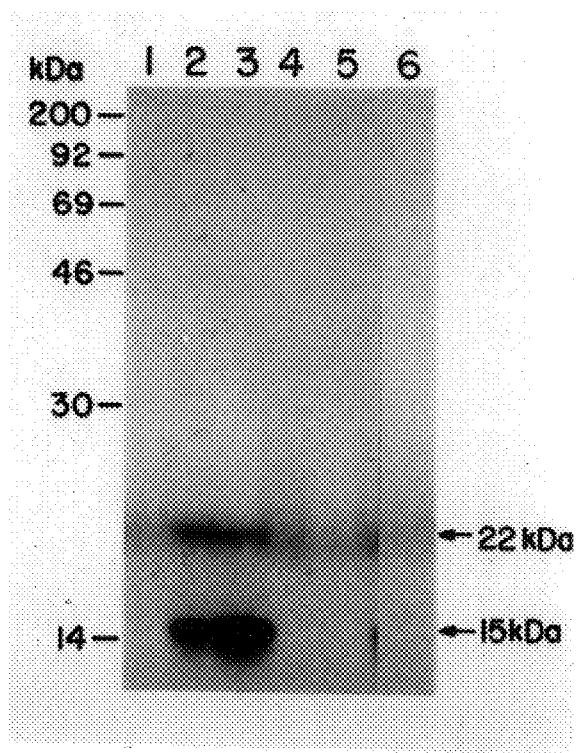

FIG. 1(C) shows an SDS polyacrylamide electrophoresis gel of the expressed protein product of DAP-1 cDNA translated in vitro in a reticulocyte lysate preparation. In vitro translation of RNA (0.5 μg) transcribed from the λ1 cDNA (lane 2) and from the subclones p6, p4, p5 and p8 are shown in lanes 3–6, respectively. Lane 1 corresponds to the background obtained in the absence of RNA administration to the reticulocyte lysates. The labeled proteins were fractionated on 12% SDS polyacrylamide gels. The position of the radioactive molecular weight markers (Amersham) is marked. The two translated proteins, the major 15 kDa and minor 22 kDa proteins, are indicated by arrows.

Figure 1D:
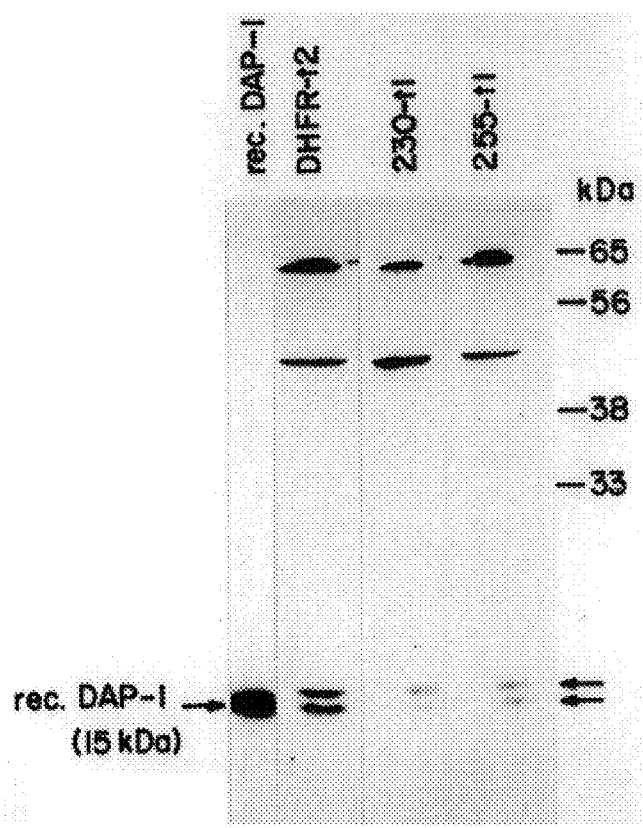

FIG. 1(D) shows an immunoblot analysis of recombinant and cellular 15 kDa DAP-1 protein. Bacterially produced DAP-1 protein (300 ng) and the indicated HeLa cell extracts (350 μg) were fractionated on SDS polyacrylamide gels (12%), blotted to nitrocellulose and reacted with affinity purified antibodies generated against the 15 kDa DAP-1. The cells were treated with IFN-γ (750 U/ml) for 4 days before their extraction. The two arrows point to the position of the cellular DAP-1 protein. The antibodies also recognize two non-relevant bands of 60 and 45 kDa that are not modulated by the antisense RNA expression. Quantitation of the reduction in DAP-1 protein was done by densitometric analysis. The calibration of the protein content in each slot was done by referring to the signals of the non-relevant bands. The prestained protein markers (Sigma) are marked.

FIGS. 2A–D show RNA and protein expression of the DAP-2 gene, wherein:

FIG. 2(A) shows a Northern blot analysis of sense and antisense mRNA obtained from two clones of HeLa cells transfected with the control constructs (DHFR-t1 and DHFR-t2) and two clones of cells transfected with the 256 construct (t1 and t2). Total RNA was prepared from the 256-t1 and 256-t2 HeLa cell transfectants either before (0 hours) or at 3 and 24 hours after treatment with IFN-γ (750 U/ml) and 20 μg samples were processed on Northern blots. Fragment #256 was used as a probe. The position of the sense and antisense mRNAs is indicated. The GAPDH mRNA levels were used for the calibration of the RNA amounts in each blot.

In FIG. 2(B) the blot consists of total RNA (20 μg) from K562 cells, parental HeLa cells, the two DHFR-transfected HeLa cell populations and the two HeLa cell populations that were transfected with the pTKO1–256. The blot was hybridized with the cDNA insert of λ29. The Ethidium Bromide staining of the RNA samples is shown.

FIG. 2(C) shows an in vitro phosphorylation assay. Cell lysates were prepared from COS-7 cells either before (lane 1) or after transfection with the PECE-FLAG expression vector that carries the coding region of the λ29 cDNA (lane 2). Samples of 400 μg were immunoprecipitated with anti-FLAG™ (M2) monoclonal antibodies (IBI) and subjected to phosphorylation assays.

FIG. 2(D) shows immunoblot analysis of recombinant and cellular DAP-2 protein. The COS-7 cells were transiently transfected with the PECE-FLAG-DAP-2 expression vector. Samples of cell lysates, 100 μg from COS-7 cells and 400 μg from HeLa cells, were fractionated on SDS polyacrylamide gels (7.5%), immunoblotted and reacted with affinity purified polyclonal antibodies raised against the N-terminal DAP-2 peptide. In the lower panel the blot was reacted with monoclonal antibodies against vinculin (Sigma Immunochemicals). Lanes: 1, non-transfected COS-1 cells; 2, transfected COS-1 cells; 3, DHFR-t1 cells; 4, 256-t1 cells; 5, 256-t2 cells. In lane 2 the same 160 kDa protein was also detected with anti-FLAG™ (M2) monoclonal antibodies (IBI) (not shown).

FIGS. 3A–C show morphological features of the cytostatic and cytotoxic responses to IFN-γ in HeLa cells. All cultures were seeded at an initial density of 10,000 cells per $cm^2$.

FIG. 3(A) shows light microscopy of HeLa cells transfected with pTKO1-DHFR construct (DHFR-t1 cells), on days 3 and 8 of culturing in the absence (a,c) or the presence (b,d) of IFN-γ (750 U/ml). (Magnification ×400). Note the absence of refractile mitotic cells during the cytostatic phase of responses to IFN-γ (in b) and the appearance of round cells that were detached from the substratum during the killing phase (in d).

FIG. 3(B) shows staining of DNA with DAPI; a. DHFR-t1 non-treated cells removed by trypsinization and mounted on glass slides. b. Detached DHFR-t1 cells collected 7 days after IFN-γ treatment. Nuclei with condensed or fragmented chromatin are indicated by arrows. (Magnification ×1000).

FIG. 3(C) shows scanning and transmission electron micrographs of cells transfected with the control construct DHFR-t1 and the 230-t1 construct. DHFR-t1 HeLa cell populations (a–d) and the 230-t1 antisense transfected cells (e and f), were cultured either in the absence (a, c, e) or in the presence (b, d, f) of IFN-γ (750 U/ml). (a,b,e,f), scanning electron micrographs were taken after 7 days using GSM 6400 SEM (Jeol). Bars=10 mm (×2200 magnitude in all the four samples). (c and d), transmission electron micrographs taken after 7 days using TEM (Philips 410) at a magnitude of ×2800. The condensed nuclei and the surface blebs are indicated by arrows.

Figure 4C:
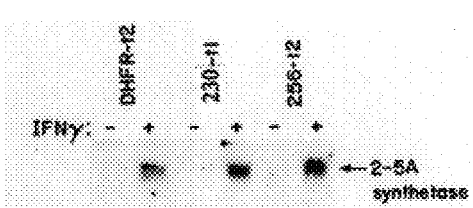

FIGS. 4A–C show that the antisense RNA expression from plasmids of groups 1 and 2 reduces the susceptibility of HeLa cells to the killing effects of IFN-γ but has no effect on early IFN-γ signalling.

FIGS. 4 (A–B) show the number of viable cells as determined by light absorption at 540 nm, as a function of time; the cells being transfected either with the control construct DHFR-t1 (●—1(A) and 1(B)); the 255 or 230 construct (▲—1(A)) or with two clones t1 and t2 of the 256 construct (▲—1(B)). The results are shown both for cell growth with (+) and without (−) administration of 750 U/ml of IFN-γ. Each point is the average of a quadruplicate determination with a SD that ranged between 2–5%.

FIG. 4(C) shows a Northern blot analysis of 2–5A synthetase gene induction. The indicated HeLa cell transfectants were incubated for 24 hours in the presence (+) or absence (−) of IFN-γ (750 U/ml). Twenty mg of total RNA were analyzed. The cDNA of the 2–5A synthetase was used as probe.

Figure 5:
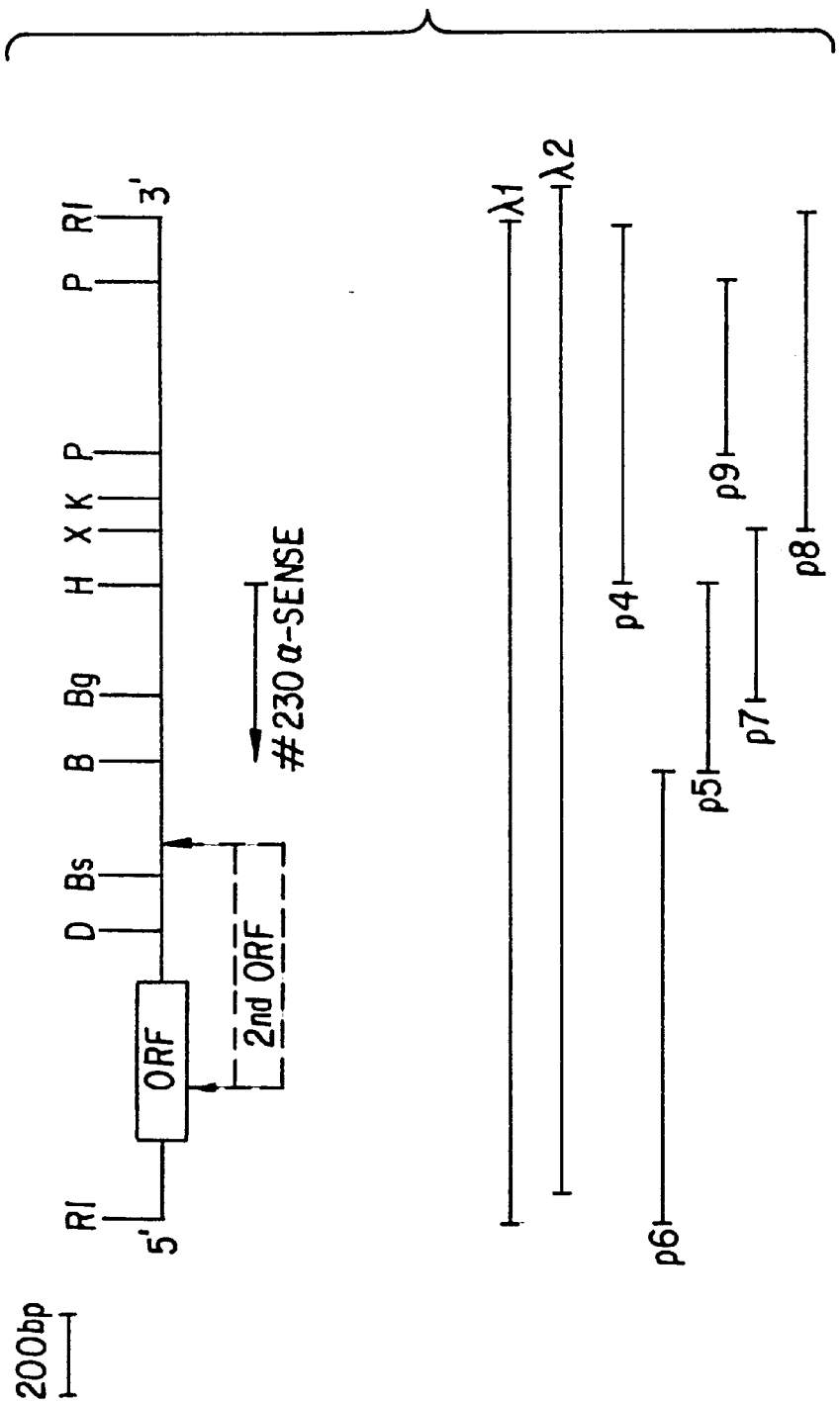

FIG. 5 shows the restriction map of the λ1 cDNA clone that carries the DAP-1 cDNA.

Figure 6A:
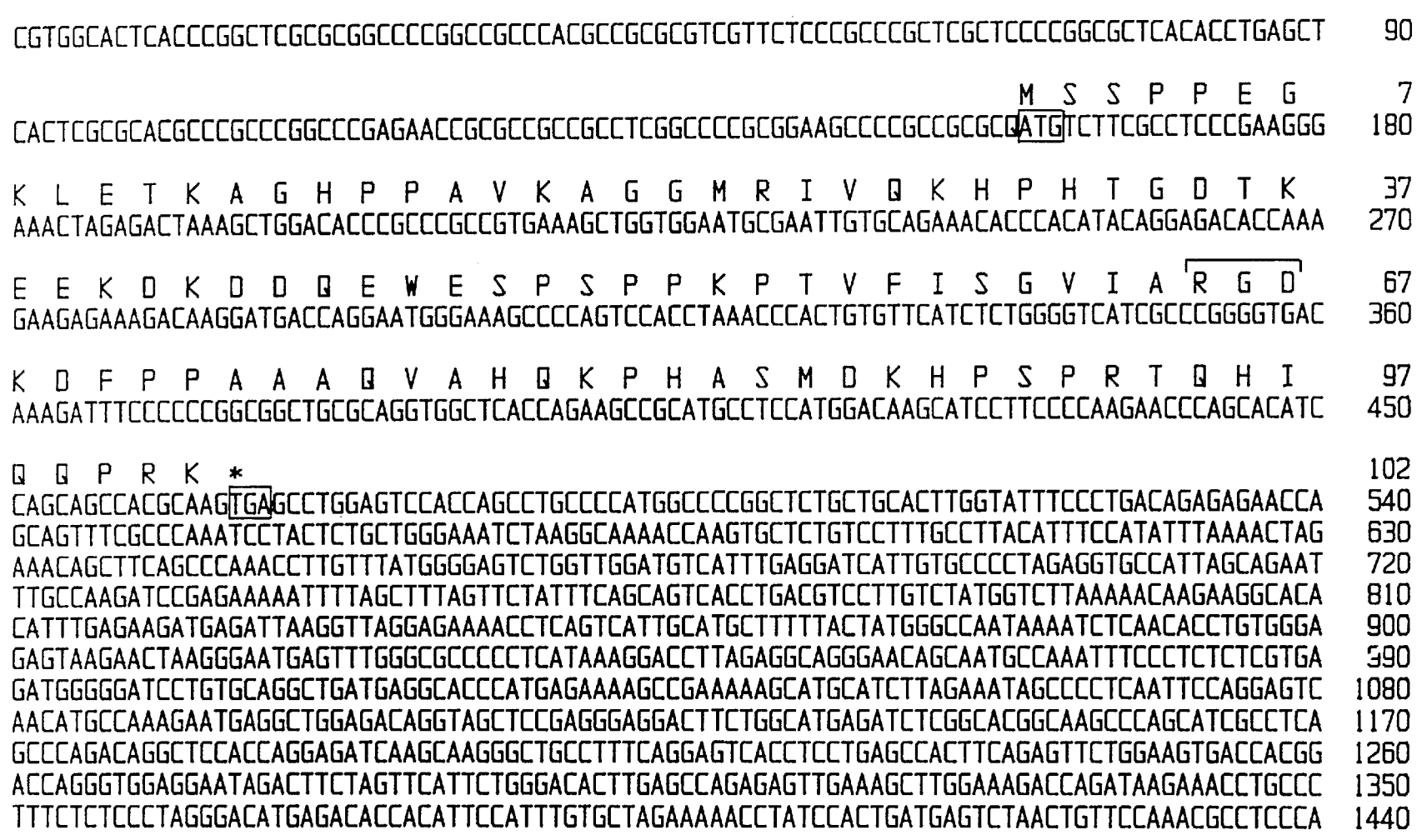

FIG. 6 shows the DNA sequence and predicted amino acid sequence of DAP-1.

Figures 7, 12B:
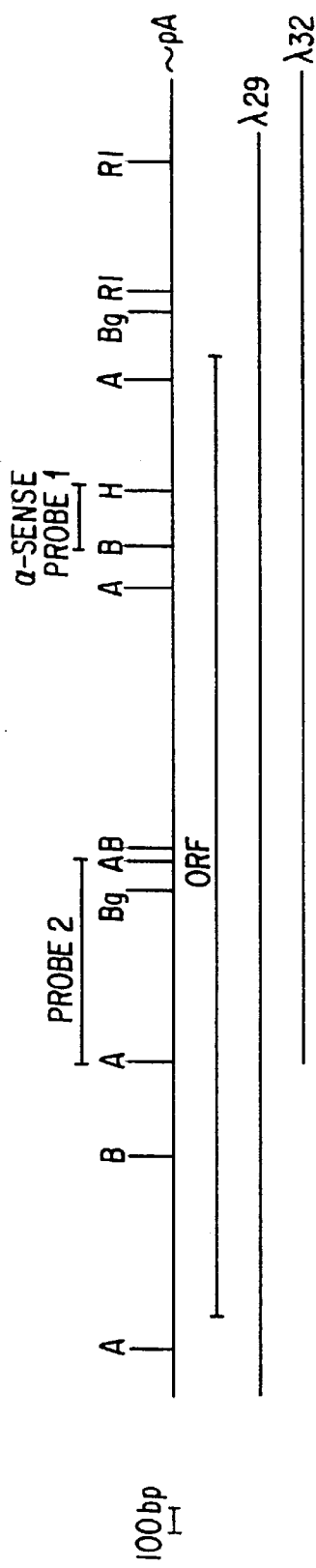

FIG. 7 shows the restriction map of the λ29 cDNA clone, that carries the DAP-2 cDNA.

Figure 8C:
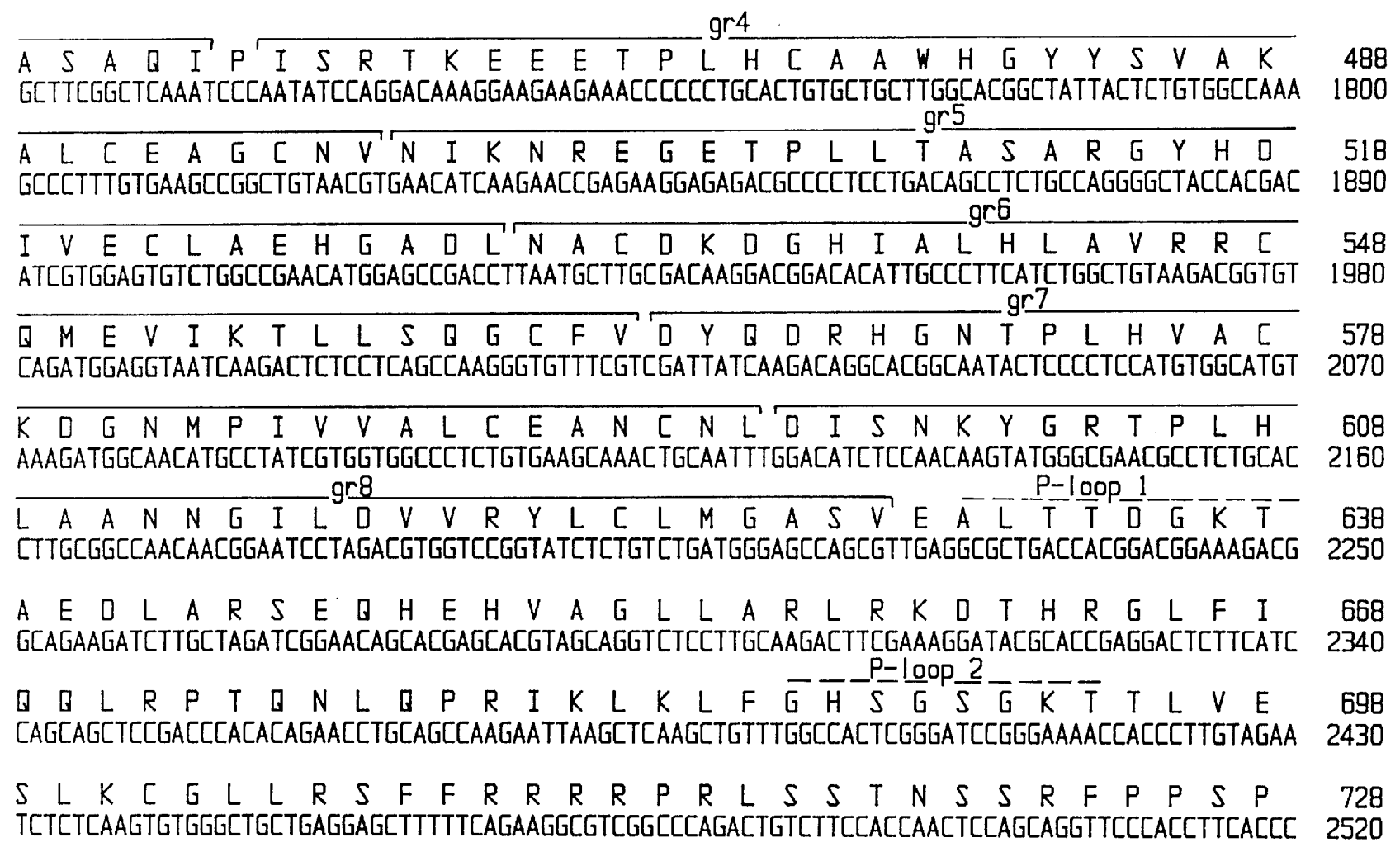
Figure 8E:
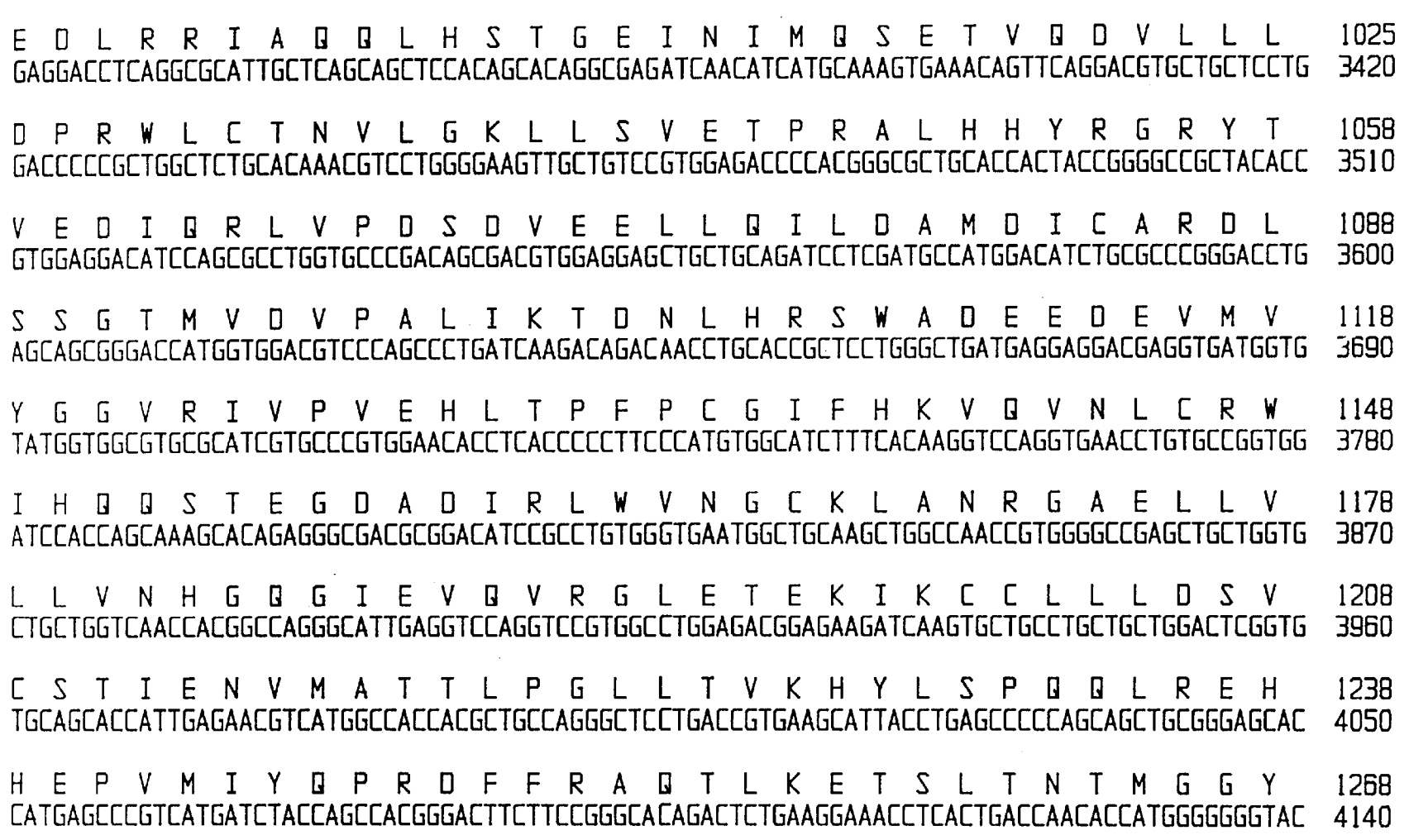

FIG. 8 shows the DNA sequence and predicted amino acid sequence of DAP-2.

Figure 9A:
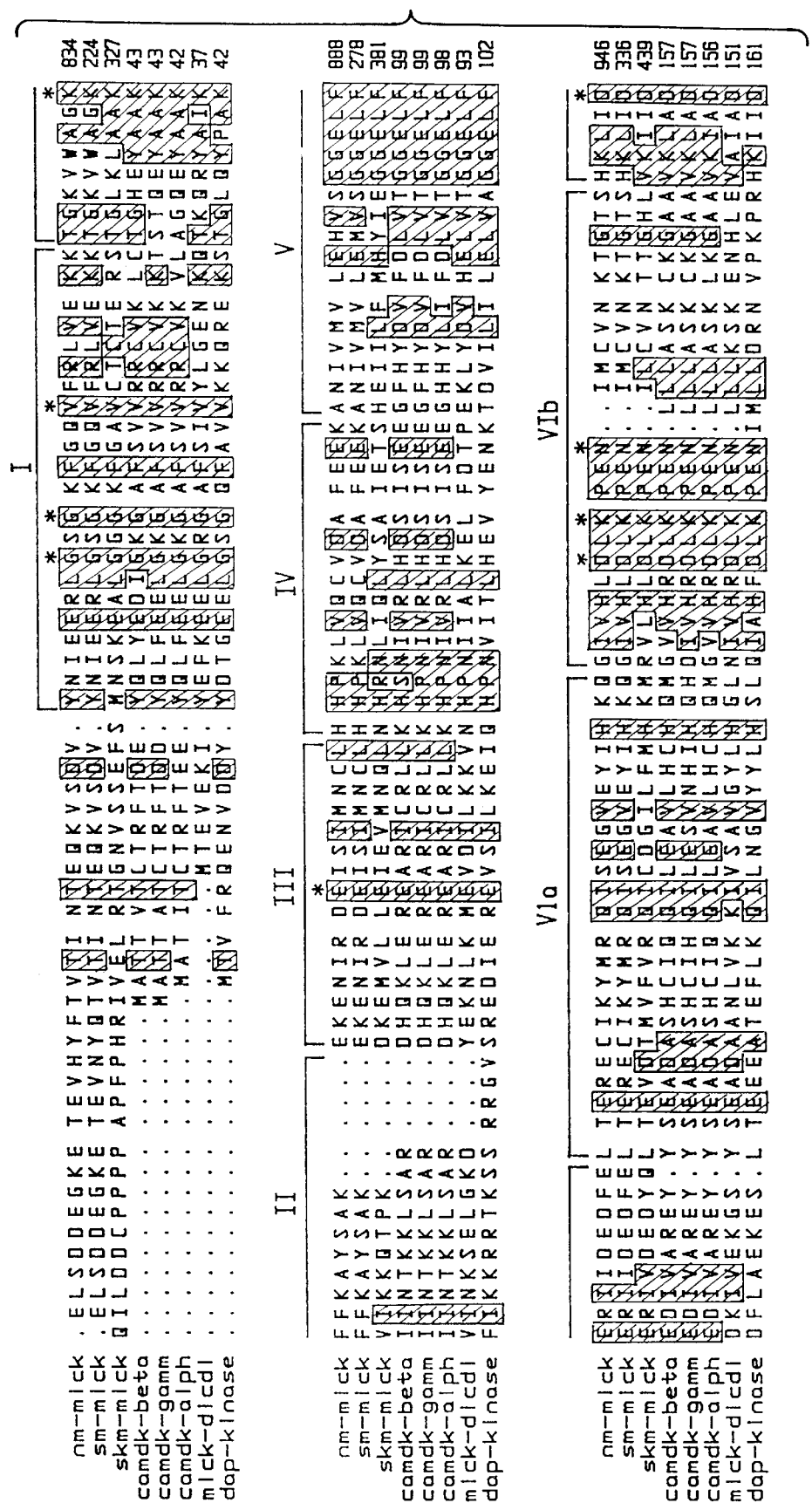

FIGS. 9A–D show DAP-2 sequence homologies to other serine/threonine kinases and alignment of the ankyrin repeats of DAP-2, wherein:

In FIG. 9(A) the protein kinase domain sequences of the DAP-2 are aligned with the corresponding domains of other calmodulin-dependent kinases. The kinase subdomain structure (numbered I–XI) and the region implicated in calmodulin recognition and binding (designated as calmodulin regulatory region) are indicated. The obligatory conserved amino acids within the kinase domain are labeled with asterisks. Numbers at the right mark positions relative to the N-terminus of primary translational products of each kinase. Solid background indicates identical amino acids within the compared kinases. Stippled background indicates positions where the amino acids are not identical but similar. nn-mlck—non-muscle myosin light chain kinase (chicken); sm-mlck—smooth muscle myosin light chain kinase (chicken); skm-mlck—skeletal muscle myosin light chain kinase (rat); camdk-alph,-beta,-gamm -calcium/calmodulin dependent protein kinase II - α-, β- and γ-subunits, respectively; mlck-dicdi—dictyostelium discoidium (slime mold) myosin light chain kinase.

Figure 9B:
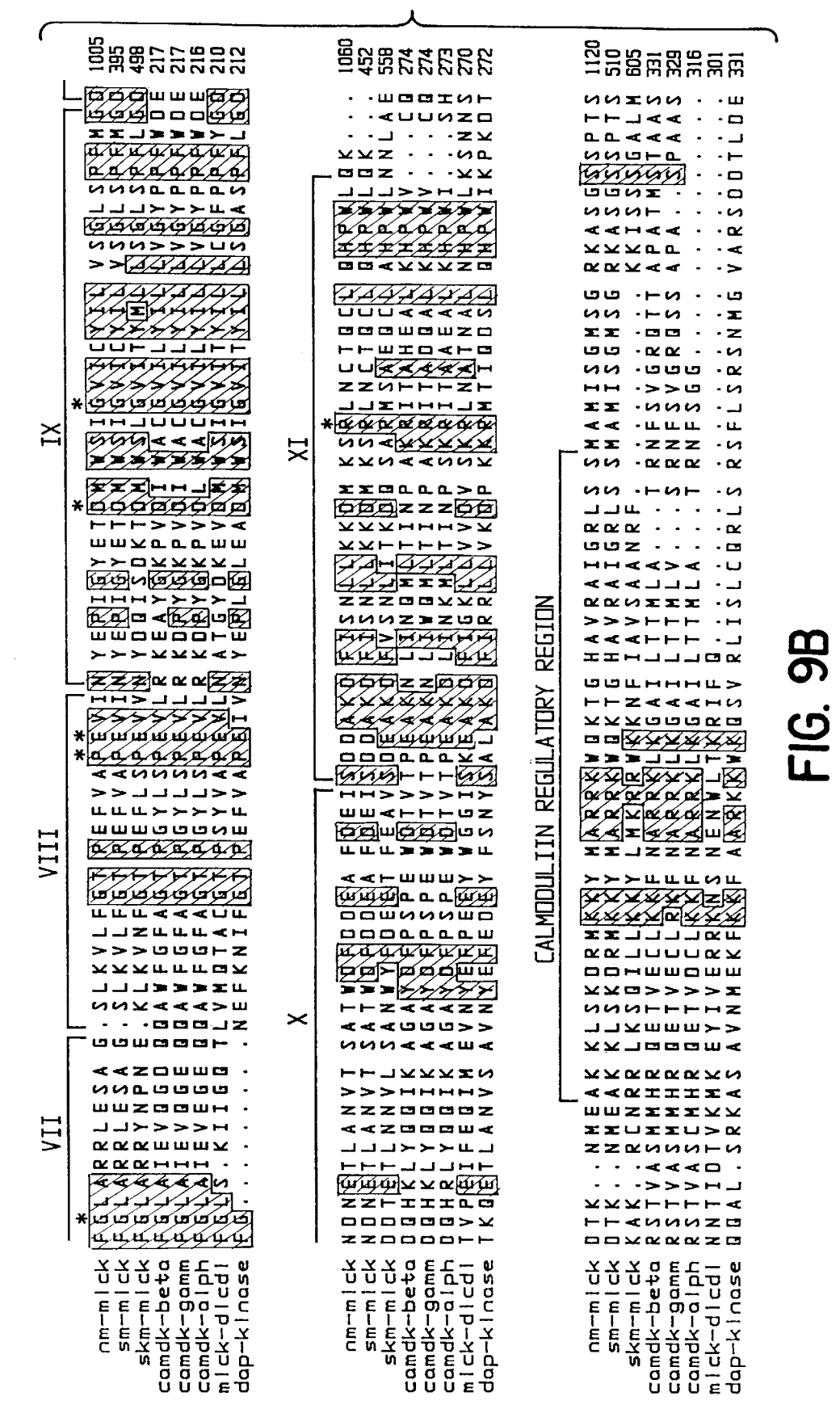

FIG. 9(B) shows alignment of kinase subdomains II and III of DAP-2 and the corresponding domains of different cell cycle dependent kinases. dm2 -Drosophila CDC2 homologue; pssalre—Human serine/threonine kinase PSSALRE; kpt2—Human serine/threonine protein kinase PCTAIRE-2; kin28—yeast (*S.cerevisiae*) putative protein kinase; mo15—Xenopus protein kinase related to cdc2 that is a negative regulator of meiotic maturation; kkialre—human serine/threonine protein kinase KKIALRE.

Figures 8G, 9C, 9D:
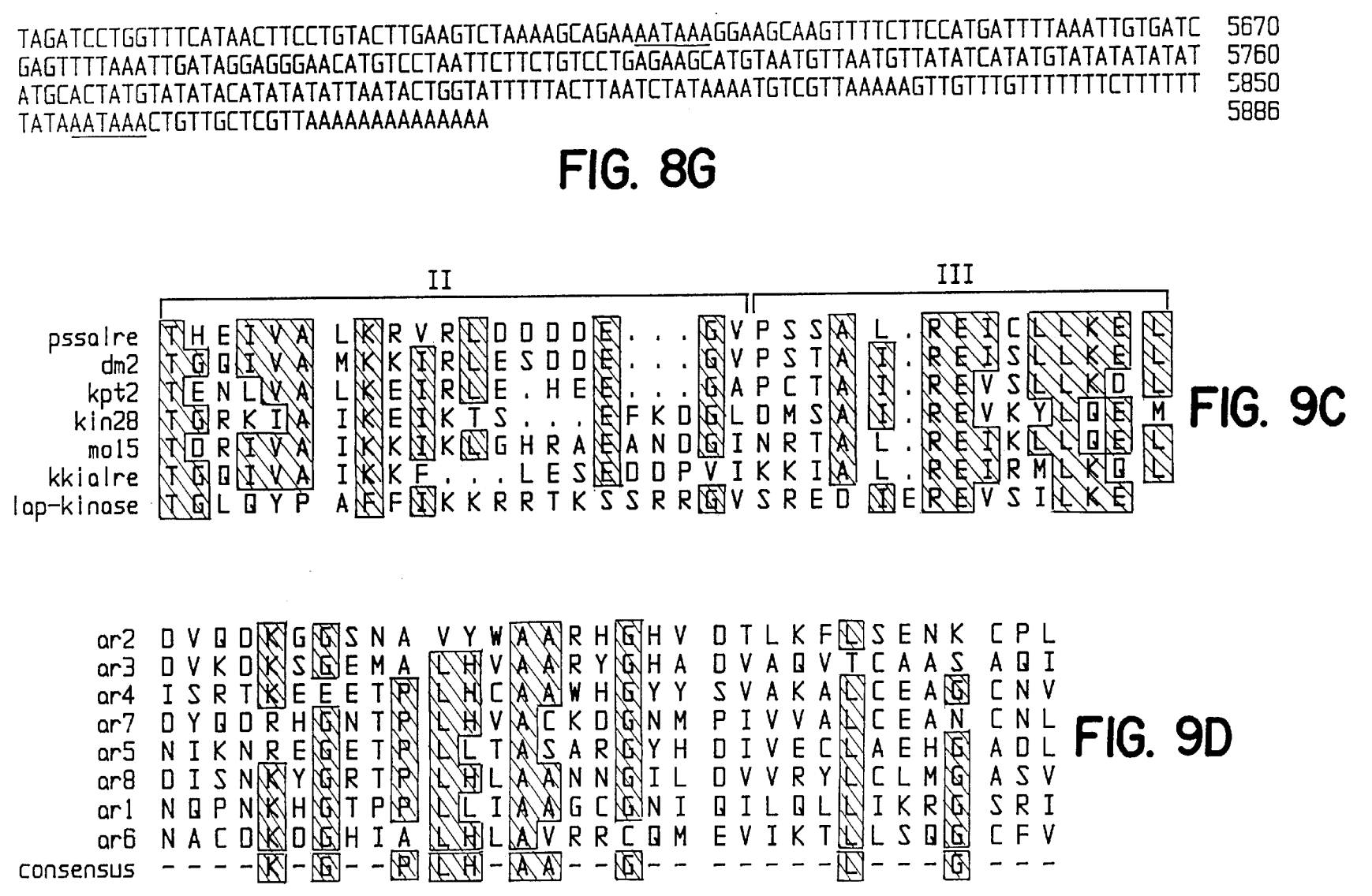

FIG. 9(C) shows alignment of DAP-2 ankyrin repeats. Solid background indicates identical amino acids. A consensus sequence of the DAP-2 ankyrin repeats is shown at the bottom. The position of each individual repeat along the cDNA is illustrated in FIG. 9(B). ar 1–8, ankyrin repeats.

Figure 10:
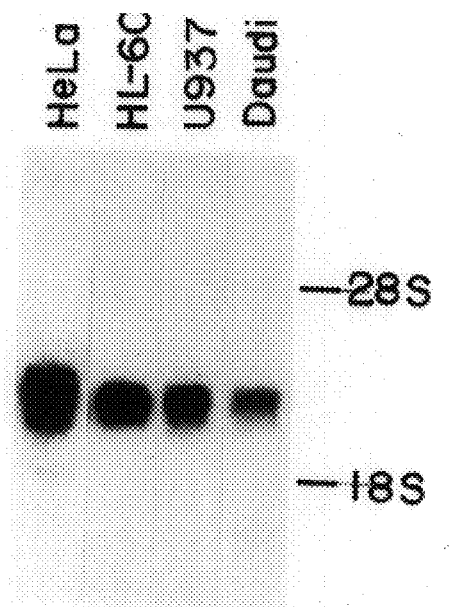

FIG. 10 shows Northern blot analysis of mRNA obtained from several hematopoietic cells probed with labeled DAP-1 cDNA.

Figure 11:
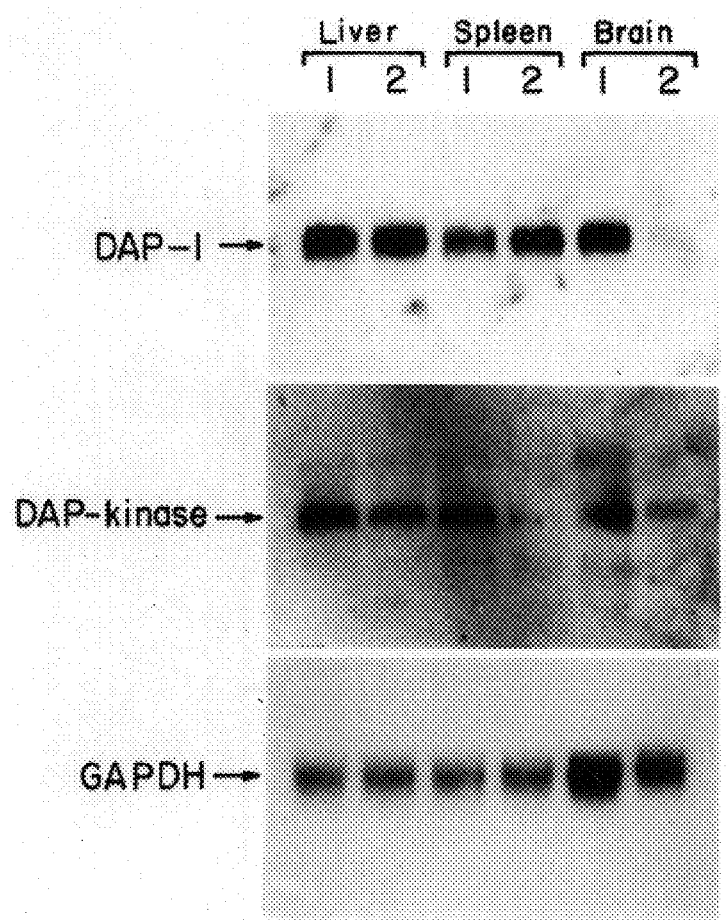

FIG. 11 shows Northern blot analysis of mRNA obtained from liver, spleen or brain of normal embryos (2) and embryos with Down Syndrome (1) both probed with the labeled cDNA or DAP-1 or DAP-2. In order to evaluate levels of total mRNA, GAPDH was used (bottom).

FIG. 12 shows the DNA sequence and predicted amino acid sequence of DAP-3.

FIG. 13 shows a partial DNA sequence of DAP-4.

FIG. 14 shows the DNA sequence and amino acid sequence of cathepsin D.

FIG. 15 shows the DNA sequence and amino acid sequence of DAP-5.

DETAILED DESCRIPTION OF THE INVENTION

I. Isolation of antisense cDNA's that protect cells from the cytotoxic effects of IFN-α

(A) Experimental procedure (A$_1$) Obtaining cDNA clones

A cDNA library (100 µg DNA) was generated from a mixture of mRNA's harvested before and at 1, 2, 4, 12, 24 and 48 hours after treatment of HeLa cells with IFN-γ (200 U/ml). It was cloned in antisense orientation into the EBV-based pTKO1 expression vector, as previously described in detail (Deiss and Kimchi, supra). The resulting expression library of about $10^5$ independent clones was introduced into $8 \times 10^6$ HeLa cells ($10^6$ cells per 9 cm plate) by the calcium phosphate transfection technique. In order to determine the efficacy of transfection, a fraction of the transfectants was selected with hygromycin B (200 µg/ml, Calbiochem). The resulted efficacy was around 5%. In parallel, the majority of the transfected cells were plated at a cell density of 1500 cells per cm$^2$ and were selected with both hygromycin B (200 µg/ml) and IFN-γ (750 U/ml). Selective media was changed every 3–4 days. After 28 days the cells that survived and/or grew in the presence of IFN-γ were expanded for 2 weeks and pooled. The extrachromosal DNA was obtained according to the method of Hirt (Hirt, B. (1967) J. Mol. Biol., 26:365), cleaved with the restriction enzyme DpnI and introduced into *Escherichia coli* HB101 host cells. The cleavage with DpnI ensured that only episomal DNA that have replicated in HeLa cells was transfected into bacteria.

A few bacterial clones were obtained by the above procedure which included DNA antisense sequences, some of which were able to protect the cells from the death-promoting effects of IFN-γ.

(A$_2$) Classification of the antisense cDNA clones

Plasmid DNAs were prepared from 10 individual bacterial clones. PCR amplified cDNA inserts were generated from each plasmid using specific primers that correspond to the immediate flanking sequence of the cDNA insertion sites in the pTKO1 vector. The size of the cDNA inserts ranged between 300 to 800 bp. The PCR fragments were used as labeled probes to search on Southern blots for possible cross hybridization between some of the rescued antisense cDNA clones.

(B) Results (B$_1$) Classification of Clones

The above 10 cDNA clones were classified into six distinct nonoverlapping groups, some constituting several members (clones) and some constituting of a single member. Those clones relevant for the present invention are shown in the following Table 1:

TABLE 1

Initial characterization of antisense cDNA clones rescued from IFN-γ-treated HeLa cells

| No. | antisense cDNA clones | cDNA length (bp) | mRNA size (Kb) | DNA product |
|---|---|---|---|---|
| 1. | 230, 254, 255, 264, 258 | 320 | 2.4 | DAP-1 |
| 2. | 256 | 367 | 6.3 | DAP-2 (kinase) |
| 3. | 259 | 252 | 1.7 | DAP-3 |
| 4. | 253 | ~300 | 4.5 | DAP-4 |
| 5. | 260 | ~800 | 4.0 | DAP-5 |
| 6. | 229 | 370 | 2.5 | Cathepsin D |

Inserts 230, 254, 255, 264 and 258 of group 1 seemed to be completely identical to one another. The PCR fragments were sequenced and the results were compared with sequences present in the EMBA nucleic acid database. All inserts of groups 1 through 5 were found to be novel.

(B$_2$) Detection of mRNA

The DNA fragments thus obtained were used to detect and determine the expression level in HeLa cells of mRNA which hybridized to these fragments. 20 µg of total RNA from the parental HeLa cells were fractionated on gels, blotted and reacted with the different probes. Each probe recognized a single mRNA transcript of a different size (Table 1). Expression levels of mRNA's reactive with group 2 were low while those reactive with group 1 were relatively high.

II. Second transfection by isolated antisense cDNA

Levels of expression of antisense RNA in secondary transfectants (A) Experimental procedure To ensure that the above isolated antisense cDNA's are sufficient in order to protect cells from the death promoting effects of IFN-γ, subconfluent monolayers of HeLa cells were transfected with 40 μg DNA of the individual rescued pTKO1 plasmids (in duplicates) and subjected to the single selection of hygromycin B. Pools of approximately $10^4$ hygromycin resistant clones were generated from each transfection and were kept as 6 duplicates of stable polyclonal populations. The sensitivities of the above clones to an application of IFN-γ was then determined.

The vector pTKO1-DHFR (Deiss and Kimchi, supra) which carried a non-relevant construct served as control. The control vector was introduced in parallel into HeLa cells and produced two independent polyclonal population of stable transfectants designated DHFR-t1 and t2.

The double stranded cDNA fragments from construct 230 and 256 (from groups 1 and 2, respectively) were used as probes in Northern blot analysis in order to detect mRNA transcripts both in non-transfected and transfected HeLa cells. These two specific cDNA inserts were labelled by commonly used commercial labelling kits. They were subcloned into Bluescript™ vectors (Stratagene, USA) to facilitate both the preparation of the cDNA inserts and the production of single stranded RNA probes therefrom.

(B) Results

Constructs 230 (group 1) As can be seen in FIG. 1A the cDNA insert in this construct hybridized to a single endogenous 2.4 Kb mRNA transcript, both in nontransfected and transfected HeLA cells. In stable transfectants containing the antisense constructs of clones 230 and 255, an additional composite antisense transcript was detected by this 230 probe. It consisted of 320 bases of the original cDNA insert and 800 additional bases of sequences derived from the expression cassette (SV40 early promoter together with sequences till the polyadenylation signal). One of the RNA labeled strands produced by the Bluescript™ vector hybridized exclusively to the endogenous 2.4 Kb mRNA while the complementary strand hybridized only to the 1.1 Kb RNA confirming that the latter is indeed an antisense mRNA (data not shown).

The amount of the antisense RNA in clones 230 and 255 exceeded the sense mRNA levels by 3 to 6 fold (FIGS. 1A, 1B). After IFN-γ treatment the level of antisense expression was further elevated due to the presence of IFN-γ-stimulated response element (ISRE) in the pTKO1 vector (Deiss and Kimchi, supra), thus leading to 15 fold excess of antisense over sense transcripts (FIG. 1B). The endogenous 2.4 Kb mRNA level was neither modulated by IFN-γ, nor influenced by the high antisense expression.

Construct 256 (group 2)

As can be seen in FIGS. 2A and 2B, the construct of the 256 clone (367 bp in size) hybridized on Northern blots to a single endogenous 6.3 Kb mRNA transcript which was expressed in all tested cells at relatively low levels. In the 256-t1 and t2 transfected cells it also hybridized to a composite 1.2 Kb RNA that consisted of 367 bases of the cDNA insert and 800 bases of sequences derived from the expression cassette in the vector (FIG. 2). The antisense orientation of fragment #256 in the pTKO1 vector was confirmed upon sequencing of the sense cDNA clone (FIG. 7). The amount of the antisense RNA expressed from pTKO-1 plasmid #256 in non-treated HeLa cells exceeded the sense mRNA levels by more than 100 fold. Moreover, due to the presence of IFN-stimulated response element (ISRE) in the pTKO1 vector, the levels of antisense mRNA expression were further elevated after IFN-γ treatment (FIG. 3).

III. Response of cells transfected with antisense cDNAs to IFN-γ

(A) Experimental procedure

The HeLa polyclonal population transfected with the individual antisense cDNAs were cultured in the presence of both hygromycin B and IFN-γ (750 U/ml). Growth and viability parameters were examined: (1) under the light microscope, (2) by electron microscopy, and (3) by DAPI staining (0.5 μg/ml; Sigma). For more detailed quantitation, a neutral red uptake assay was performed: the different polyclonal HeLa cell populations were cultivated in 96-well microtiter plates at subconfluent cell densities and then treated with IFN-γ (750 U/ml) or left untreated. All the cells were continuously maintained in a hygromycin B-containing medium to select for transfected cells. The two DHFR-transfected HeLa cell populations (t1, t2), prepared as described above, served as control cultures that display the typical growth sensitivity curves to IFN-γ. The examined antisense cDNA transfected cells were the 230-t1, 255-t1 (group 1) and 256-t1, 256-t2 (group 2). Viable cells were stained with neutral-red and the dye uptake was quantified by measuring O.D. at 540 nm in quadruplicates during the 14 days of the experiment.

(B) Results

The microscopic examination of parental and control DHFR-transfected HeLa cells revealed that IFN-γ triggered a biphasic pattern of responses. The cells stopped proliferating during the first four days of IFN-γ treatment but still remained viable (in trypan-blue exclusion tests) and displayed a flattened morphology characteristic of the cystostatic responses to IFN-γ (FIG. 3A, b). The reduction in the proliferation rate during this period was also measured by a sharp decline (by more than 90%) in the thymidine uptake into DNA (not shown). This type of IFN-γ-induced proliferation arrest was then followed by massive cell death that occurred in a non-synchronous fashion over a period of an additional 10 days. The cells gradually reduced their size, rounded up and detached from the plates (FIGS. 3A, d). Staining of DNA with DAPI after detachment of cells from the substratum revealed gross changes in the nuclear morphology characteristic of programmed cell death. This included nuclear pyknosis, chromatin condensation, sometimes detected preferentially at the nuclear periphery, and chromatin segmentation (FIG. 3B, b). Transmission electron micrographs of the IFN-γ-treated cells prior to their detachment revealed other morphological changes including the disappearance of surface microvilli, surface blebbing, budding off cytoplasmic projections and cytoplasmic disintegration, in addition to the nuclear pyknosis and chromatin condensation (details shown in FIG. 3C, d). The antisense RNA expression from pTKO-1 plasmid of group 1 reduced the susceptibility of the cells to the killing effects of IFN-γ: more cells survived on the plates and the above-mentioned death associated morphological changes appeared at much lower frequency (compare the scanning electron micrographs of the IFN-γ-treated DHFR-transfected cells in FIG. 3C, b to the IFN-γ-treated 230-t1 cells in FIG. 3C, f). Similar microscopic observations, showing protection from the IFN-γ-induced cell death, were also made with respect to three other clones from the aforementioned groups of antisense cDNAs, i.e. 2, 3, and 7 (not shown).

A neutral-red uptake assay was then performed to determine more accurately, on a quantitative basis, both the typical biphasic responses of control cultures to IFN-γ and the reduced susceptibility of the antisense expressing cultures to the IFN-γ-induced cell death. The two DHFR-transfected HeLa cell populations (t1, t2) served as the control cultures in this assay and the antisense cDNA transfected cells examined were the 230-t1, 255-t1 (group 1) (FIG. 4A) and 256-t1, 256-t2 (group 2) (FIG. 4B). In the absence of IFN-γ, all the transfected HeLa cells behaved the same and displayed practically identical growth curves suggesting that the antisense RNA expression had no effects on the normal growth of cells. Another feature that was not changed by the antisense RNA expression was the extent of the cytostatic responses to IFN-γ. As shown in FIGS. 4A and 4B, IFN-γ has similarly reduced the proliferation rate of all the transfected cultures and they all displayed the same extent of reduction in the neutral-red dye uptake during the first 4 days (before cell death starts to be microscopically evident). After 4 days of treatment the picture changed drastically. While almost all control cells died during the subsequent days of IFN-γ treatment leading to minimal values of the neutral-red dye uptake on day 14, a significant fraction of cells that expressed antisense RNA survived in the presence of IFN-γ, as reflected by the sustained values of the dye uptake. The resistance to the IFN-γ-induced cell killing was very similar in all the four tested cultures that expressed the two different antisense RNAs (FIGS. 4A, 4B). These data indicate that expression of antisense RNA from groups 1 and 2 protects the HeLa cells exclusively from the IFN-γ-induced cell death and not from its cytostatic action. It is noteworthy that the antisense RNA expression did not affect the early biochemical steps in the signaling of IFN-γ as deduced from the normal mRNA induction by IFN-γ of the 2–5A synthetase gene in these transfected cells (FIG. 4C). Altogether, it is concluded that among all criteria tested only the death inducing effects of IFN-γ were interrupted by the antisense RNA expression.

IV. Responses of cells transfected with antisense constructs to necrotic cell death It became interesting at this stage to check whether the antisense RNA expression can also protect the HeLa cells from a necrotic type of cell death. For this, the effect of TNF-α added in combination with cycloheximide (CHX) was examined in the various HeLa cell populations. Unlike the effect of IFN-γ, the cell death that was induced by TNF-α+CHX in HeLa cells was very rapid (50% killing after 3 hours) and displayed typical features of necrosis such as swelling of the cells before their lysis. As shown in Table 2, while the antisense RNA expression from groups 1 and 2 protected the cells from the IFN-γ-induced cell killing, there was no protection from the TNF-α-induced necrotic cell death. All the examined HeLa cell transfectants were killed by the TNF+CHX combination with similar time kinetics and at the same efficiency. Northern blot analysis demonstrated that the levels of the antisense mRNA transcripts in 256-t1 cells were not reduced by the TNF+CHX treatment at 5 hours (not shown) thus excluding the possibility that loss of the antisense RNA expression, caused by the treatment, may be the reason for lack of protective effects from the necrotic cell death. This further suggests a certain specificity of the protective mechanisms regarding the type of cell killing.

TABLE 2

Expression of antisense RNA (from groups 1 and 2) protects from the IFN-γ-induced programmed cell death but not from the TNF-induced necrotic cell death. (A = 540 nm)

| | | DHFR-t1 | DHFR-t2 | 230-t1 | 255-t1 | 256-t1 |
|---|---|---|---|---|---|---|
| 14 days | No treatment | 0.396 | 0.345 | 0.385 | 0.324 | 0.336 |
| | IFN-γ | 0.026 | 0.017 | 0.136 | 0.158 | 0.159 |
| 5 hours | No treatment | N.D. | 0.148 | 0.130 | N.D. | 0.140 |
| | TNF-α + CHX | N.D. | 0.053 | 0.026 | N.D. | 0.022 |
| 20 hours | No treatment | 0.211 | 0.248 | 0.223 | 0.173 | 0.190 |
| | TNF-α + CHX | 0.002 | 0.001 | 0.003 | 0.0015 | 0.002 |

Each treatment was done in quadruplicates and the average values of dye uptake, measured by the OD at 1=540 nm, is presented at the indicated time intervals. The SD was between 2–4%. N.D, not done.

V. Cloning of DAP-1 cDNA and determination of amino acid sequence.

An HL-60 cDNA library constructed in λgt10 vector was screened with the cDNA insert of pTKO1-230. Two independent clones, λ1 and λ2, almost completely overlapping and carrying cDNA inserts of about 2.3 Kb were analysed. [01 cDNA clone encompasses the 5'-untranslated region, short coding region(s) and a relatively long 3'-untranslated region that constitutes more than 60% of the cDNA clone (FIG. 5).

The nucleotide sequence of the cDNA carried by λ1 and its predicted amino acid pattern are presented in FIG. 6. This cDNA is 2232 bp long and contains a potential polyadenylation signal ATTAAA at its 3' end. The open reading frame (ORF) is very short, starting from the initiation codon at nucleotide positions 160–162 and ending at termination codon TGA at positions 466–468 (SEQ ID NO: 1). This ORF is preceded by an extremely GC-rich 5'-untranslated region and potentially codes for a protein consisting of 102 amino acids with calculated MW of 11.2 kDa. The amino acid composition predicts a basic protein (isoelectric point= 10), rich in prolines (15%) which displays two blocks of charged residues, one in the middle and the other at the 3' end of the protein. The high proline content may cause some anomalies in the protein's migration on gels. Search for motifs ("Motifs" program; GCG Software Package) indicated that the protein contains two potential sites for casein kinase II phosphorylation at positions 3 and 36, a single potential protein kinase C phosphorylation site at the C-terminus (position 91) and a consensus phosphorylation site of the cdks at position 51. In addition, the protein contains the consensus sequence RGD at position 65–67, a tripeptide that in some proteins plays a role in cell adhesion, and a potential SH3 binding motif, SPSPP, at position 49–53 (Cowburn (1994) Struc. Biol. 1, 489–491). No indications for the presence of signal peptide or transmembranal domain have been found (SAPS prediction; Brendel et al., (1992) PNAS USA, 89:2002–2006). The amino acid sequence showed no significant homology to known proteins.

Fragment #230 was used as a probe on Southern blots containing human genomic DNA, digested with various restriction enzymes that do not cut it. A single band was visualized upon hybridization with DNA cleaved with EcoRI, BamHI, PstI and XbaI, suggesting the existence of a single copy gene (not shown). This new gene was termed DAP-1 (Death Associated Protein-1).

In vitro translation assays in reticulocyte lysates confirmed that the predicted ORF codes for the major 15 kDa protein translated from the cloned 2.4 Kb transcript. The full length cDNA insert as well as four subclones that span different regions of the molecule (i.e., p6, p5, p8, and p4; see FIG. 5) were transcribed and translated in vitro. Among all the tested subclones, only the 5' 1 Kb portion of the DAP-1 cDNA (p6) directed the in vitro synthesis of proteins (FIG. 1C). The major translated product migrated on gels as a 15 kDa protein. Mutation at the ATG codon at position 160–162 (ATG to GGC) completely eliminated the synthesis of the 15 kDa protein, thus confirming the position of the start point of this protein (data not shown). In addition to the 15 kDa protein product, a second protein of 22 kDa was also translated at lower efficiency from λ1 and the p6 cDNAs (FIG. 1C). Its translation was not influenced by the elimination of the ATG codon at position 160 but the protein was shortened to a size of 16 and 18 kDa upon cleavage of the p6 subclone with DraI and BstYI restriction endonucleases, respectively (not shown; for restriction map see FIG. 5). These criteria fit another potential open reading frame, which is detected in the nucleotide sequence in a different phase with respect to the first ORF (FIG. 6). It starts at the ATG codon (positions 287–289) and ends at termination codon TGA (positions 816–818 (SEQ ID NO: 3)). It has the potential to code for a protein consisting of 176 amino acids with a calculated molecular weight of 19.9 kDa, and has no significant homology to any known proteins.

To analyse the expression of the major DAP-1 protein in cells, rabbit polyclonal antibodies were prepared against the bacterially produced 15 kDa protein. The affinity purified antibodies recognized on immunoblots two closely migrating proteins in extracts of HeLa cells; the lower band comigrated on gels with the bacterially produced 15 kDa DAP-1 protein. The slower migrating form may represent a post-translationally modified version of the protein. In the HeLa cell transfectants, 230-t1 and 255-t1, expressing the elevated levels of antisense RNA that develop in the presence of IFN-γ (15 to 1 ratio), the DAP-1 protein levels were reduced by 75% and 78%, respectively, as compared to the DHFR-tranfected cultures (FIG. 1D). The two upper non specific bands (that are not competed with excess of the bacterially produced DAP-1) were not affected by the antisense expression, thus supporting the selectivity of the effect.

VI. Cloning of DAP-2 and determination of amino acid sequence

As mentioned above, expression studies indicated that the double-stranded cDNA fragment #256 (367 bp in size) hybridized on Northern blots to an endogenous 6.3 Kb mRNA transcript. The same single 6.3 Kb mRNA transcript was detected in HeLa (parental and transfectants) and in K562 cells when the full length cDNA (see below) was used as a probe on Northern blots (FIG. 2B). The cDNA insert from pTKO1-256 was therefore used to screen a K562 cDNA library.

Approximately 4×10[6] pfu were screened with the #256 cDNA insert and 40 positive clones were isolated after two rounds of sequential walking screening. The sequencing was performed on an Applied Bio-systems DNA sequencer 373 A. Sequence uniqueness and relatedness were determined using FASTA (GCG software package) at the nucleotide level and FASTA, BLASTP, and BLOCKS programs at the amino acid level (S. Henikoff and J. G. Henikoff, Nucleic Acids Res. 19, 6565 (1991).

Two clones, λ29 and λ32, were chosen for sequencing (FIG. 7). The resulting composite sequence of both cDNAs consists of 5886 nucleotides and contains a poly A tail that starts at position 5872 and is preceded by two polyadenylation signals AATAAA (FIG. 8). The 3'-untranslated region also contains two ATTTA instability motifs found in the 3'-noncoding portions of short-lived mRNAs (G. Shaw and R. Kamen, Cell 46, 659 (1986)). The mRNA contains a single long open reading frame that starts at position 337, ends at position 4605 and potentially codes for a protein of 1423 amino acids (FIG. 8) (SEQ ID NO: 3). The calculated molecular weight of the protein product is about 160 kDa. Affinity purified polyclonal antibodies were raised against the N-terminal 20 amino acid peptide of the protein. These antibodies recognized on immunoblots a 160 kDa recombinant protein that was produced in COS-1 cells after transfection with a vector that expressed the entire coding region of the cDNA (FIG. 2D). These antibodies reacted in HeLa cells with an endogenous protein of the same size. In the antisense RNA expressing cells, 256-t1 and 256-t2, the steady state levels of the 160 kDa protein were 10 and 5 fold lower than in the DHFR control cells while a non relevant protein, vinculin, displayed similar expression levels in all HeLa cell transfectants (FIG. 2D). Thus, expression of anti-sense RNA from pTKO-1 plasmid #256 in HeLa cells resulted in a significant reduction in the amount of the corresponding protein.

We were able to define several known domains and motifs that are present in this protein. Its extreme N-terminus is composed of a protein kinase domain that spans 255 amino acids from position 13-267. On the basis of its structure, it is likely to be a serine/threonine type of protein kinase having a classical composition of XI subdomains with all conserved motifs present (FIG. 8) (S. K. Hanks and A. M. Quinn, Methods Enzymol. 200, 38 (1991)). This novel kinase was termed DAP-2 or DAP-kinase (Death Associated Protein-kinase).

The kinase domain falls into a family of that of calmodulin-dependent kinases. The homology to known kinase domains that constitute this group, including the myosin light chain kinases, ranges between 34%–49% (FIG. 9A). Three main differences distinguish the kinase domain of DAP-kinase from other members of calmodulin-dependent kinase family: 1) Subdomain 11 is relatively long and has a stretch of basic amino acids (KKRRTKSSRR); 2) Subdomain III mostly resembles that of the cell cycle dependent kinases (FIG. 9B). Interestingly, the typical sequences of the cell cycle dependent kinases (PSTAIRE, PSSALRE, PCTAIRE, KKIALRE) are located in subdomain III; and 3) Subdomain VII is extremely short and consists of only 7 amino acids.

Right downstream to the kinase domain there is an additional stretch of homology that is present in almost all members of the family of calmodulin-dependent kinases, and was implicated in calmodulin-recognition and binding; B. P. Herring, J. T. Stull, P. J. Gallagher, J. Biol. Chem. 265, 1724 (1990); M. O. Shoemaker et al., J.Cell. Biol. 111, 1107 (1990); F. H. Cruzalegui et al., Proc. Nath. Acad. Sci. USA 89, 12127 (1992)). Downstream of the calmodulin-recognition domain, an ankyrin repeats domain was identified spanning 265 amino acids from position 365 to 629. It is composed of 8 repeats of 33 amino acids each, not separated by spacers except for a single proline residue that separates three N-terminal repeats from five C-terminal ones (FIGS. 8 and 9C). Ankyrin repeats are involved in protein—protein interactions in a variety of proteins (P. Michaely and V. Bennett, Trends in Cell Biology 2, 127 (1992)), but were not described before in the context of serine/threonine kinases. One tyrosine kinase carrying ankyrin repeats has been recently identified in Hydra vulgaris (T. A. Chan et al., Oncogene 9, 1253 (1994)). In the DAP-kinase, the 8 ankyrin repeats may mediate the interaction with a putative effector or a regulatory molecule, or influence the substrate selectivity and/or stability of the kinase-substrate interactions.

Immediately downstream to ankyrin repeats there are two subsequent potential P-loop motifs, ALTTDGKT and GHSGSGKT, identified through the consensus sequence, G[A]XXXXGKT[S]. Comparison of DAP-kinase potential P-loop motifs to the corresponding consensus sequences within seven ATP or GTP-binding protein families demonstrates that only the 3'P-loop has some similarity to P-loop consensus of elongation factors, ATP synthase b-subunits and thymidine kinase. Actually, a stretch of 33 amino acids following the eighth ankyrin repeat that encompasses the putative 5' P-loop, may represent a ninth ankyrin repeat that is less conserved than others. DAP-kinase also carries multiple potential sites for post-translational modifications, and has neither transmembranal domain nor signal peptide. The Prosite bank search, using the program Motifs (GCG Software Package) revealed that the DAP-kinase protein contains a consensus sequence for the C-terminal amidation site at position 1376 (this suggests that 47 C-terminal amino acids can be cleaved from the protein body). It also contains consensus sequences for six N-glycosylation sites, and potential phosphorylation sites for cAMP-dependent kinase (six), casein kinase II (twenty eight) and protein kinase C (twenty).

Altogether, the deduced amino acid sequence of the DAP-kinase suggests that a very unique type of calmodulin-regulated serine/threonine kinase has been rescued. The combination of serine/threonine kinase domain, ankyrin repeats and additional possible ATP/GTP binding sites outside the kinase domain in one protein (FIG. 10) has not been previously described. A size of 160 kDa is rare among serine/threonine kinases and DAP-kinase is actually the largest calmodulin-dependent kinase known to date. The ability of DAP-kinase to bind calmodulin, recently confirmed in yeast two hybrid system (not shown), is consistent with the notion that in many cases programmed cell death is $Ca^{2+}$ dependent (S. Sen, Biol. Rev. Camb. Philos. Soc. 67, 287 (1992); S. Lee, S. Christakos, M. B. Small, Curr. Opin. Cell. Biol. 5, 286 (1993)). Moreover, it has been recently reported that calmodulin antagonists inhibited the glucocorticoid-induced apoptosis (D. R. Dowd, D. P. Mac, B. S. Komm, M. R. Haussler, R. Miesfeld, J. Biol. Chem. 266, 18423 (1991)), and that inhibitors of myosin light chain kinases blocked the TNF-induced apoptotic cell death (S. C. Wright, H. Zheng, J. Zhong, F. M. Torti, J. W. Larrick, J. Cell. Biochem. 53, 222 (1993)).

In order to verify that DAP-2 is truely a kinase, COS cells were transiently transfected with an expression vector (PECE-FLAG) that carries a fragment of the 129 cDNA that encompasses the entire coding region (from the abovementioned start ATG to the first EcoRI site at the 3'end). Cell lysates were immunoprecipitated by anti-FLAG monoclonal antibodies and washed immunoprecipitates were assayed for in-vitro autophosphorylation in the presence of calmodulin and $Ca^{2+}$. As shown in FIG. 2C, a single phosphorylated band of 160 kDa appeared upon fractionation of the in-vitro reaction products on polyacrylamide gels. This experiment provides the first direct proof that the recombinant protein has intrinsic kinase activity, as suggested by the predicted amino acid structure.

VII. Expression of DAP-1 and DAP-2 proteins in various cells and tissues

Examination of a variety of cell lines and tissues revealed that these two genes are likely to be ubiquitously expressed. FIG. 10 shows the Northern blot analysis of RNA from different hematopoietic cells probed with the DAP-1 cDNA. The 2.4 Kb mRNA transcript of this gene was detected in granulocytes (HL-60) B lymphoid (Daudi) and macrophage (U937) cells. The expression levels in the hematopoietic cells was lower than in HeLa cells. FIG. 11 shows results of examination of the mRNA expression in human embryonic tissues: brain, spleen (predominantly B cells) and liver (predominantly erythrocytes). Again the single 2.4 Kb mRNA transcript was detected in these tissues by the DAP-1 cDNA probe.

The DAP-2 cDNA probe 2 recognized the 6.3 Kb mRNA encoded by this gene in these different tissues (FIG. 11). The embryonal liver and spleen tissues from Down syndrome seemed in this blot to express higher levels of the DAP-2 gene (compared to the GAPDH levels) while the brain tissue from Down syndrome contained higher levels of DAP-1 mRNA than the corresponding normal brain.

VIII. Cloning and sequencing of DAP-3, DAP-4 and DAP-5

Clone 259 (DAP-3) was sequenced and used to screen a K562 λgt10 cDNA library as described above for DAP-1 and DAP-2. The sequence of the (almost) full length cDNA of DAP-3 and the deduced amino acid sequence is shown in FIG. 12.

Clone 253 (DAP-4) was partially sequenced as described above for DAP-1 and DAP-2 and the results are shown in FIG. 13.

Clone 260 was among the rescued vectors described in Table 1 which protected the HeLa cells from IFN-γ-induced programmed cell death. It was isolated as described in the detailed description of the invention (section I(A)). It carried a cDNA fragment of 863 bp and the sequence analysis indicated that it corresponded to a novel gene (named DAP-5). Northern blot analysis indicated that DAP-5 is transcribed into a 4.5 Kb mRNA. DAP-5 mRNA was found to be widely expressed in a variety of normal tissues.

The 863 cDNA fragment was used for screening a cDNA library originating from KS62 cells. The phage clone that carried the longest cDNA insert (3.9 Kb) was sequenced. This cDNA clone comprises of an open reading frame (ORF) that corresponds to 900 amino acids, as shown in FIG. 15A–15B (SEQ ID NO: 8). The deduced amino acid sequence predicts that the protein is highly homologous, yet not identical, to the translation initiation factor 4γ(eIF4γ, p220). Thus, DAP-5 may be regarded as a novel member of what appears to be a family of the eIF4γ type of translation initiation factors. Most interestingly, and very much unexpectedly, the 863 bp fragment that was presented in the original clone #260 was inserted in the vector in the sense orientation. In this region (marked by a solid line in FIG. 15A–15B; nucleotides 1764–2528) there is an ATG codon that could drive the synthesis of a mini protein that is 230 amino acids long. Indeed, in vitro transcription and translation of this fragment yielded a protein of that predicted size, and mutation of this ATG eliminated the mini-protein synthesis. Transfections of HeLa cells with vectors that express the 863 cDNA fragment from the tetracycline regulated promoter protected the cells from cytokine-induced cell death. One possibility is that the mini-protein functions as a dominant negative mutant that competes with the death-inducing properties of the full length protein. Other possibilities also exist.

IX. Identification of DAP-7

The initial microscopic observations, performed on the different HeLa cells that had been transfected with the individual rescued pTKO1 clones (described in Table 1), indicated that plasmid pKTO1-229 (group 7) conveyed similar effects to those conferred by the plasmids from group 1. It reduced the susceptibility of the cells to the IFN-γ-induced cell death but not to its cytostatic effects.

The cDNA carried by plasmid pTKO1-229 was identified upon sequencing as a BamHI-HindIII fragment of human cathepsin D cDNA, which was present in the expression vector in the antisense orientation. The DNA probe, corresponding to fragment #229, hybridized as expected to a single endogenous 2.5 Kb mRNA, both in control and in the transfected HeLa cells. The steady state levels of cathepsin D sense mRNA were not affected by the IFN-γ treatment. In the pTKO1-229 transfected cells the DNA probe also hybridized to the composite antisense RNA. The levels of antisense cathepsin D RNA were stimulated 5-fold in response to IFN-γ due to the presence of an ISRE enhancer element in the pTKO1 expression vector (not shown).

The cathepsin D protein was identified on immunoblots using commercially available polyclonal antibodies (Oncogene Science). It was found that in the control clones, IFN-γ prevented the appearence of the mature 34 kDa chain while the 48 kDa active single chain precursor was retained at abnormal high levels in these cells. It appears that this single chain precursor is the specific cathepsin form that functions during cell death.

Cathepsin D is an aspartic protease that is found normally in lysosomes where it functions in protein catabolism. Yet, in some pathological situations it has been suggested that this protease can function in the cytosol, and its activity was associated with degenerative brain changes, muscular dystrophy and connective tissue disease pathology (Matus and Green (1987); Biochemistry, 26, 8083–8036). The present invention shows for the first time that the expression of this protease is indispensable for the execution of programmed cell death that is induced by IFN-γ. Thus, cathepsin D joins the growing list of proteases that play a key role in different scenarios of programmed cell death.

The DNA sequence and amino acid sequence of cathepsin D are shown in FIG. 15 (Faust, P. L. et al. (1985) PNAS USA 82, 4910–4914).

---

I claim:

1. An isolated DNA molecule, the expression product of which is involved in cytokine-induced programmed cell death, said molecule comprising nucleotides 337 to 4605 of FIG. 9 (SEQ ID NO: 3).

2. The isolated DNA comprising a sequence encoding a protein or polypeptide encoded by the DNA molecule of claim 1.

3. An isolated nucleic acid having a sequence fully complementary to the DNA molecule of claim 1.

4. The nucleic acid of claim 3 wherein said nucleic acid is a probe.

5. An isolated vector comprising the DNA molecule of claim 1 and promoter sequence operably linked to the DNA molecule for propagating and replicating the DNA sequence in a host cell.

6. The isolated vector according to claim 5, wherein said vector further comprises sequences operably linked to the DNA molecule for transcribing said DNA molecule into an m-RNA.

* * * * *

UNITED STATES PATENT AND TRADEMARK OFFICE
CERTIFICATE OF CORRECTION

PATENT NO.   : 5,968,816
DATED        : October 19, 1999
INVENTOR(S)  : Adi Kimchi It is certified that error appears in the above-identified patent and that said Letters Patent is hereby corrected as shown below:

Drawings,
Sheet 10 of 23, consisting of Figs. 6B, 13 and 14, has been deleted and replaced with the corrected Sheet 10 of 32, consisting of Figs. 6B and 13, as shown on the attached page. Sheets 22 of 23 and 23 of 23, consisting of Figs. 15A-15B have been deleted and replaced with the corrected Sheets 22 of 32 and 23 of 32, consisting of Figs. 14A-14B, as shown on the attached pages.
Add the drawing sheets 24-32, consisting of new Figs. 15A-15I, as shown on the attached pages.

Column 3,
Line 3, change "16" to -- 15A-15I --.
Line 5, change "15" to -- 14A-14B --.

Column 4,
Lines 47 and 62, change "15B" to -- 15I --.
Line 66, change "15" to -- 14A-14B --.

Column 5,
Line 13, change "15" to -- 14A-14B --.

Column 6,
Lines 38 and 40, change 14" to -- 14A-14B --.
Lines 38 and 40, change "15B" to -- 15I --.

Column 9,
Line 46, change "14" to -- 14A-14B --.
Line 48, change "15" to -- 15A-15I --.

Column 18,
Line 47, change "15A" to -- 15I --.
Line 56, change "15B" to -- 15I --.

UNITED STATES PATENT AND TRADEMARK OFFICE
CERTIFICATE OF CORRECTION

PATENT NO.    : 5,968,816
DATED         : October 19, 1999
INVENTOR(S)   : Adi Kimchi It is certified that error appears in the above-identified patent and that said Letters Patent is hereby corrected as shown below:

Column 20,
Line 22, change "15" to -- 14A-14B --.

Column 53,
Line 20, change "Fig. 9" to -- Fig. 8 --.

Signed and Sealed this

Tenth Day of September, 2002

Attest:

Attesting Officer

JAMES E. ROGAN
Director of the United States Patent and Trademark Office

FIG. 6B

```
CCTGGTGTGCACAGCTGCCTGGGTCCATTGTCATCAGGTTGTCCTCCGATTTTTAGATGAGTTTCCTGTCTAGAGATGTC  1530
CTAGTCTGCTCACTTGGCTGGTGGCAGTAGGGTACCCTGCCGTCCTGAAAAGCCAGAGGGTTCACCTAGTCAGACGAAACTCAGAACAGT  1620
GCTTGTGGAGGGCCTGACTGTCCTGCTCACCCACAGCCGATCTGCTGCAGGTCAGCAACTGTGTCGTGAGCAGTGCCAACCACCAGCCT  1710
TTCTGGCTGTGTTCCAGTTCAGTCTGCCAGCTGGTGAGGGCAGAGGCAGCAGCGCCCCTCCTCCTGAGGGAGC  1800
ATGGCACAGCCTCACACTTGAAAGACGGTGTTTGGTTTCCCATCTAATCAACTTAAGGGAAGCGGGCATGTACCCTTCAAGGCCTGTCA  1890
CCACCTATTTCCTGATCAGTTGGTATAAACTGAGGGTGGCTTTTAGAGACCCAGACTTGGTTGGCAGCGTGCCTGCATGCAGGCGTGCCAGC  1980
AAGCACCTCCCAGCTGCCTTTGGAGCAGCAGCATCCTAATGTCTTCAGCCAGAGGGATGCCGCGTCCAGAACACCAGTTAGGCCTGAGACCCTGCC  2070
CTGCCTGCTGCAGAAATCCAGAAGCATCCTAATGTCTTCAGCCAGCAGGGAGGGCTGTATTTCCAGAGGTGCGCTTTTTATG  2160
TACTTTTAGCTAGATGTGGCATGCATGTGTGAGTTTAGATCATTAAATCCAAAATGTTTGCCTAAATGAGG  2232
```

FIG. 13

```
CTAGATGAGGCAGATATAAGAGTCA     25
TCCAAAAAGGACAGAGAAAAAAAA     50
CAGACAAATCAGTTGTCAGTATCCA    75
TGGCCTCTGATTCTGTCTCAACCAT   100
GAAACAGAAGTGACACATATAC       122
CTGCTAAAAG
```

```
                                                                        M  Q  P
  1  GGCTATAAGCGGCACGGCCTCGGGCACCCTTCTGGGACCCTTCGACCCGGCCGCGCCGCATGCAGCCC   60
     S  S  L  L  P  L  A  L  L  L  L  A  A  P  A  S  A  L  V  R
 61  TCCAGCCTTCTGCCGCTGGCTCTGCCCTTGCCTGCTGGTGCACCGCTTGGTGCTCGGCTGTCAGG    120
     I  P  L  H  K  F  T  S  I  R  R  T  M  S  E  V  G  G  S  V
121  ATCCCGCTGCACAAGTTCACGTCCATCCGCCGGACCATGTCGGAGGTTGGGGGCTCTGTG        180
     E  D  L  I  A  K  G  P  V  S  K  Y  S  Q  A  V  P  A  V  T
181  GAGGACCTGATTGCCAAAGGCCCCGTCTCAAAGTACTCCCAGGCGGTGCCAGCCGTGACC         240
     E  G  P  I  P  E  V  L  K  N  Y  M  D  A  Q  Y  G  E  I
241  GAGGGGCCCATTCCGGAGGTGCTCAAGAACTACATGGACGCCCAGTACTACGGGGAGATT        300
     G  I  G  T  P  P  Q  C  F  T  V  V  F  D  T  G  S  S  N  L
301  GGCATCGGGACGCCCCCCCAGTGCTTCACAGTCGTCTTTGACACGGGCTCTTCCAACCTG        360
     W  V  P  S  I  H  C  K  L  L  D  I  A  C  W  I  H  H  K  Y
361  TGGGTCCCCTCCATCCATTGCAAACTGCTTGACATCGCTTGCTGGATCCACCACAAGTAC        420
     N  S  D  K  S  S  T  Y  V  K  N  G  T  S  F  D  I  H  Y  G
421  AACAGGACAAGTCCAGCATCACTTACGTCAAGAATGGTACCTCGTTTGACATCCACTATGGC      480
     S  G  S  L  S  G  Y  L  S  Q  D  T  V  S  V  P  C  Q  S  A
481  TCGGGGAGCCTCTCCGGGTACCTGAGCCAGGACACTGTGTCGGTCCCTGCAGTCAGCG         540
     S  S  A  S  A  L  G  G  V  K  E  R  Q  V  F  G  E  A  T
541  TCGTCAGCCTGCCCTGGGGTGTCAAAGTGGAGAGGCAGGTCTTTGGGGAGGCCACC          600
     K  Q  P  G  I  T  F  I  A  A  K  F  D  G  I  L  G  M  A  Y
601  AAGCAGCCAGGCATCACTTTCATCGCAGCCAAGTTCGATGGCATCCTGGGCATGGCCTAC       660
     P  R  I  S  V  N  N  V  L  P  V  F  D  N  L  M  Q  Q  K  L
661  CCCCGCATCTCCGTCAACAACGTGCTGCCCGTCTTCGACAACCTGATGCAGCAGAAGTTG      720
     V  D  N  I  F  S  F  Y  L  S  R  D  P  D  A  Q  P  G  G
721  GTGGACCAGAACATCTTCTCCTTCTACCTGAGCAGGGACCCAGATGCGCAGCCTGGGGGT      780
     E  L  M  L  G  G  T  D  S  K  Y  Y  K  G  S  L  S  Y  L  N
781  GAGCTGATGCTGGGTGGCACAGACTCCAAGTATTACAAGGGTTCTCTGTCCTACCTGAAT      840
```

FIG.14A

```
     V  T  R  K  A  Y  W  Q  V  H  L  D  Q  V  E  V  A  S  G  L
841  GTCACCCGCAAGGCCTACTGGCAGGTCCACCTGGACCAGGTGGAGGTGGCCAGCGGGCTG    900
     T  L  C  K  E  G  C  E  A  I  V  D  T  G  T  S  L  M  V  G
901  ACCCTGTGCAAGGAGGGCTGTGAGGCCATTGTGGACACAGGCACTTCCTCATGGTGGGC     960
     P  V  D  E  V  R  E  L  Q  K  A  I  G  A  V  P  L  I  Q  G
961  CCGGTGGATGAGGTGCGGGAGCTGCAGAAGGCCATCGGGGCCGTGCCGTTGATTCAGGGC    1020
     E  Y  M  I  P  C  E  K  V  S  T  L  P  A  I  T  L  K  L  G
1021 GAGTACATGATCCCCTGTGAGAAGGTGTCCACTCTGCCTGCCATCACACTGAAGCTGGGA    1080
     G  K  G  Y  K  L  S  P  E  D  Y  T  L  K  V  S  Q  A  G  K
1081 GGCAAAGGCTACAAGCTGTCCCAGGAGGACTACACGCTCAAGGTGTCGCAGGCGGGAAAG    1140
     T  L  L  S  G  F  M  G  M  D  I  P  P  P  S  G  P  L  W
1141 ACCCTTCTGCTGAGGGCTTCATGGGCATGGACATCCCGCCACCCAGCGGGCCACTCTGG    1200
     I  L  G  D  V  F  I  G  R  Y  Y  T  V  F  D  R  D  N  N  R
1201 ATCCTGGGGGACGTCTTCATCGGCCGCTACTACACTGTGTTTGACCGTGACAACAACAGG    1260
     V  G  F  A  E  A  A  R  L  *
1261 GTGGGCTTCGCCGAGGCTGCCCGCCTCTAGTTCCCAAGGCGTCCGCGCAGCACACAGAA     1320
1321 ACAGAGGAGAGTCCCAGAGACAGGAGGCCCCTGGCCGCAGGCCCCTCCCAGCACACACCA    1380
1381 CACACTCGCCCGCCACTGTCCTGGAAGCCGGCCCTGGAAGCCGGAGGCCAAGCCGACTTGC   1440
1441 TGTTTGTTCTGTTGGTGGGGGTCAGAGCTGATCCAGAGCACAGATCTGTTGTTGCATTGGAA 1500
1501 TCCATCTGTTGTTGGGGGGTAGAGCTGATCCAGAGCACAGATCTGTTGTTGCATTGGAA    1560
1561 GACCCCACCCAAGCTTGGCAGCCGAGCTGTCGTGTATCCTGGGGCTCCCTTCATCTCCAGG   1620
1621 AGTCCCTCCGGCCCTCGTTCCTTGAAACCTGCCAGCCCCTACCCCACACCAGGCCG       1680
1681 TCCTCCCCGGGCCTTCTGCACCAGCCCCTTGTTCAGTGTCCGGGCCGGAGATGAGGCCG    1740
1741 CCCAGTGGGGTCTGAGGATGAGCTGGAAGGAGTGAGAGGGGACAAAACCCACTTGTTGGAGC 1800
1801 CTAGAGGCCTGAGGATGAGCTGGAAGGAGTGAGAGGGGACAAAACCCACTTGTTGGAGC    1860
1861 CTGCAGGGTGGTGCTGGGGCTGTGCCAGCTCCTTCTGCCAGTGCATGTATTGGCCTGAGAGC 1920
1921 TTGGGATTGGGGGCTGGTGCTGGGGCTGTGCCAGCTGACCTCGTTGTTCCTCCCTTG     1980
1981 GGCGGCTGAGAGCCCAGCTGACTGACATACAGTGTTGTTGGCCTCCGGCCTCCCCCTC    2038
```

FIG.14B

```
         10                               30                                   50
GAATTCCGCTCTATGGAGGTGGCAGCGGGTACCGAGTGGCGGCTGCAGCAGGACTCCTC 70                             90                          110
TGAGCTGAGTTTGAGGCCGTCCCCGACTCCTTCCTCCCCCTTCCCTCCCCCTTTTTTG 130                           150                      170
TTTTCCGTTCCCCCTTCCCCTCCCTATCCCCGACGACCGGATCCTGAGGAGGGCA 190                        210                           230
GCTGCGGTGGCAGCTGCTGAGTTCTCGGTGAAGGTATTTCATTTCTCCTGTCCCCTCCCC
                                 V  L  G  E  G  I  S  F  L  S  P  P  L
                                                             270           290
TCCCCACCCCATCTATTAATATTATTCTTTGAAGATTCTTCGTTGTCAAGCCGGAAAG
 P  T  P  S  I  N  I  L  L  K  I  L  R  C  Q  A  A  K  V
         250
          310                         330                         350
TGGAGAGTGCGATTGCAGAAGGGGTGCTTCTGTTTCAGTGCTTCTTCGGGCGGAGGAG
 E  S  A  I  A  E  G  G  A  S  R  F  S  A  S  S  G  G  G  G 370                         390                           410
GAAGTAGGGGTGCACCTCAGCACCTCAGCACTATCCCAAGACTGCTGGCAACACGGAGTTCCTGGGA
 S  R  G  A  P  Q  H  Y  P  K  T  A  G  N  S  E  F  L  G  K 430                        450                             470
AAACCCCAGGGGCAAAAACGCTCAGAAATGGATTCCTGCACGAAGCACTAGACGAGATGACA
 T  P  G  Q  N  A  Q  K  W  I  P  A  R  S  T  R  R  D  D  N
```

FIG. 15A

```
        490                                510                              530
ACTCCGGCAGCAAACAACTCCGCAAACGAAAAAGAACGACATGATGCAATCTTCAGGAAAG
 S  A  A  N  N  S  A  N  E  K  E  R  H  D  A  I  F  R  K  V 550                                570                              590
TAAGAGGCATACTAAATAAGCTTACTCCTGAAAAGTTTGACAAGCTATGCCTTGAGCTCC
 R  G  I  L  N  K  L  T  P  E  K  F  D  K  L  C  L  E  L  L 610                                630                              650
TCAATGTGGGTGTAGAGTCTAAAACTCATCCTTAAAGGGGTCATACTGCTGATTGTGGACA
 N  V  G  V  E  S  K  L  I  L  K  G  V  I  L  L  I  V  D  K 670                                690                              710
AAGCCCTAGAAGAGCCAAAGTATAGCTCACTGTATGCTCAGCTATGTCTGCGATTGGCAG
 A  L  E  E  P  K  Y  S  S  L  Y  A  Q  L  C  L  R  L  A  E 730                                750                              770
AAGATGCACCAAACTTTGATGGCCCAGCAGAGGGTCAACCAGGAGAAGCAAAGCA
 D  A  P  N  F  D  G  P  A  A  E  G  Q  P  G  Q  K  Q  S  T 790                                810                              830
CCACATTCAGACGCCTCCTAATTTCCAAATTACAAGATGAATTTGAAAACCGAACTAGAA
 T  F  R  R  L  L  I  S  K  L  Q  D  E  F  E  N  R  T  R  N 850                                870                              890
ATGTTGATGTCTATGATAAGGTGAAAATCCCCTCCTCCCGAGGAGGAGAACAGAGAG
 V  D  V  Y  D  K  R  E  N  P  L  L  P  E  E  E  E  Q  R  A
```

FIG. 15B

```
                910                         930                              950
CCATTGCTAAGATCAAGATGTTGGGAAACATCAAATTCATTGGAGAGCTTGGCAAGCTTG
 I  A  K  I  K  M  L  G  N  I  K  F  I  G  E  L  G  K  L  D
                970                         990                             1010
ATCTTATTCACGAATCTATCCTTCATAAGTGCATCAAAACACTTTTGGAAAGAAGAAGA
 L  I  H  E  S  I  L  H  K  C  I  K  T  L  L  E  K  K  K  R
               1030                        1050                             1070
GAGTCCAACTCAAAAGATATGGGAGAGGATTTGGAGTGCCTCTGTCAGATAATGAGGACAG
 V  Q  L  K  D  M  G  E  D  L  E  C  L  C  Q  I  M  R  T  V
               1090                        1110                             1130
TGGGACCTAGATTAGACCATGAACGAGCCAAGTCCTTAATGGATCAGTACTTTGCCCGAA
 G  P  R  L  D  H  E  R  A  K  S  L  M  D  Q  Y  F  A  R  M
               1150                        1170                             1190
TGTGCTCCTTGATGTTAAGTAAGGAATTGCCAGCAAGGATTCGTTCCTGCTGCAGGATA
 C  S  L  M  L  S  K  E  L  P  A  R  I  R  F  L  L  Q  D  T
               1210                        1230                             1250
CCGTAGAGTTGCGAGAACACCATTGGGTTCCTCGCAAGGCTTTTCTTGACAATGGACCAA
 V  E  L  R  E  H  H  W  V  P  R  K  A  F  L  D  N  G  P  K
               1270                        1290                             1310
AGACGATCAATCAAATTCGTCAAGATGCAGTAAAAGATCTAGGGGTGTTTATTCCTGCTC
 T  I  N  Q  I  R  Q  D  A  V  K  D  L  G  V  F  I  P  A  P
```

FIG. 15C

```
                    1330                                              1370
CTATGGCTCAAGGGATGAGAAGTGACTTCTTTCTGGAGGGACCGTTCATGCCACCCAGGA
 M  A  Q  G  M  R  S  D  F  F  L  E  G  P  F  M  P  P  R  M
         1390                                1430
TGAAAATGGATAGGGACCCACTTGGAGGACTTGCTGATATGTTTGGACAAATGCCAGGTA
 K  M  D  R  D  P  L  G  G  L  A  D  M  F  G  Q  M  P  G  S
                    1450                                1490
GCGGAATTGGTACTGGTCCAGGAGTTATCCAGGATAGATTTCACCCACCATGGGACGTC
 G  I  G  T  G  P  G  V  I  Q  D  R  F  S  P  T  M  G  R  H
         1510                                1550
ATCGTTCAAATCAACTCTTCAATGGCCATGGGGACACATCATGCCTCCCACACAATCGC
 R  S  N  Q  L  F  N  G  H  G  G  H  I  M  P  P  T  Q  S  Q
                    1570                                1610
AGTTTGGAGAGAGATGGGAGGCAAGTTTATGAAAAGCCAGGGCTAAGCCAGTCTACCATA
 F  G  E  M  G  G  K  F  M  K  S  Q  G  L  S  Q  L  Y  H  N
         1630                                1670
ACCAGAGTCAGGGACTCAGGGACTCTTATCCCAGCTGCAAGGACAGTCGAAGGATATGCCACCTCGGT
 Q  S  Q  G  L  L  S  Q  L  Q  G  Q  S  K  D  M  P  P  R  F
                    1690                                1730
TTTCTAAGAAAGGACAGCTTAATGCAGATGAGATTAGCCTGAGGCCTGCTCAGTCGTTCC
 S  K  K  G  Q  L  N  A  D  E  I  S  L  R  P  A  Q  S  F  L
```

FIG. 15D

```
                        1750                              1770                              1790
TAATGAATAAAAATCAAGTGCCAAAGCTTCAGCCCCAGATAACTATGATTCCTCCTAGTG
 M  N  K  N  Q  V  P  K  L  Q  P  Q  I  T  M  I  P  P  S  A 1810                              1830                              1850
CACAACCACCAGCACTCAAACACCACCTCTGGGACAGACACCTCAGCTTGGTCTCAAAA
 Q  P  P  R  T  Q  T  P  P  L  G  Q  T  P  Q  L  G  L  K  T 1870                              1890                              1910
CTAATCCACCACTTATCCAGGAAAAGCCTGCCAAGACCAGCAAAAAGCCACCACCGTCAA
 N  P  P  L  I  Q  E  K  P  A  K  T  S  K  K  P  P  P  S  K 1930                              1950                              1970
AGGAAGAACYCCYYAAACYAACYHAAACYHYYYHYHACYHAAYAYCYAAAYAHYHHAAATH
 E  E  L  K  L  T  E  T  V  V  T  E  Y  L  N  S  G  N  A 1990                              2010                              2030
CAAATGAGGAGGCTGTCAATGGTGTAAGAGAAATGAGGGCTCCTAAACACTTTCTTCCTGAGA
 N  E  A  V  N  G  V  R  E  M  R  A  P  K  H  F  L  P  E  M 2050                              2070                              2090
TGTTAAGCAAAGTAATCATCCTGTCACTAGATAGAAGCGATGAAGATAAAGAAAAAGCAA
 L  S  K  V  I  I  L  S  L  D  R  S  D  E  D  K  E  K  A  S 2110                              2130                              2150
GTTCTTTGATCAGTTACTCAAACAGGAAGGGATAGCCACAAGTGACAACTTCATGCAGG
 S  L  I  S  L  L  K  Q  E  G  I  A  T  S  D  N  F  M  Q  A
```

FIG. 15E

```
2170                              2190                                  2210
CTTTCCTGAATGTATTGGACCAGTGTCCCAAAACTGGAGGTTGACATCCCTTTGGTGAAAT
 F   L   N   V   L   D   Q   C   P   K   L   E   V   D   I   P   L   V   K   S 2230                              2250                                  2270
CCTATTTAGCACACAGTTTGCAGCTCGTGCCATCATTTCAGAGAGGTGGTGAGCATTTCAGAAC
 Y   L   A   Q   F   A   A   R   A   I   I   S   E   L   V   S   I   S   E   L 2290                              2310                                  2330
TAGCTCAACCACTACTAGAAAAGTGGCACCCATTTTCCTCTCTTCCTACTTTGTCTTCAGCAGT
 A   Q   P   L   E   S   G   T   H   F   P   L   F   L   C   L   Q   Q   L 2350                              2370                                  2390
TAGCTAAATTACAAGATGAGAATGGTTAACAGAACTTTTCAACAAAGCAAGGTCAATA
 A   K   L   Q   D   R   E   W   L   T   E   L   F   Q   Q   S   K   V   N   M 2410                              2430                                  2450
TGCAGAAAATGCTCCCAGAAATTGATCAGAATAAGGACCGCATGTTGGAGATTTTGGAAG
 Q   K   M   L   P   E   I   D   Q   N   K   D   R   M   L   E   I   L   E   G 2470                              2490                                  2510
GAAAGGGACTGAGTTTCTTATTCCCACTCCTCAAATTGGAGAAGGAACTGTTGAAGCAAA
 K   G   L   S   F   L   F   P   L   L   K   E   K   E   L   L   K   Q   I 2530                              2550                                  2570
TAAAGTTGGATCCATCCCCTCAAACCATATATAAATGGATTAAAGATAACATCTCTCCA
 K   L   D   P   S   P   Q   T   I   Y   K   W   I   K   D   N   I   S   P   K
```

FIG. 15F

```
                2610
AACTTCATGTAGATAAAGGATTTGTGAACATCTTAATGACTAGCTTCTTACAGTACATTT
 L  H  V  D  K  G  F  V  N  I  L  M  T  S  F  L  Q  Y  I  S
      2650                                  2690
CTAGTGAAGTAAACCCCCCAGCGATGAAACAGATTCATCCTCTGCTCCTTCCAAAGAAC
 S  E  V  N  P  P  S  D  E  T  D  S  S  A  P  S  K  W  Q
    2710                      2750
AGTTAGAGCAGGAAAAAGAAGAGTACTACTATCTTTCAAGCCAGTAATGCAGAAATTCTTC
 L  E  Q  E  K  Q  L  L  L  S  F  K  P  V  M  Q  K  F  L  H
      2770                                    2810
ATGATCACGTTGATCTACAAGTCAGTGCCCTGTATGCTCTCCAGGGCACTGCRARAACA
 D  H  V  D  L  Q  V  S  A  L  Y  A  L  Q  V  H  C  Y  N  S
              2830                              2870
GCAACTTCCCAAAAGGCATGTTACTTCGCTTTTTTGTGCACTTCTATGACATGGAAATTA
 N  F  P  K  G  M  L  L  R  F  F  V  H  F  Y  D  M  E  I  I
    2890                            2930
TTGAAGAAGAAGCTTTCTTGGCTTGGAAGAAGAAGATATAACCCAAGAGTTTCCGGGAAAAG
 E  E  E  A  F  L  A  W  K  E  D  I  T  Q  E  F  P  G  K  G
      2950                        2990
GCAAGGCTTTGTTCCAGGTGAATCAGTGGCTAACCTGGTTAGAAAGTGCTGAAGAAGAAG
 K  A  L  F  Q  V  N  Q  W  L  T  W  L  E  T  A  E  E  E  E
```

FIG. 15G

```
             3030                                    3050
AATCAGAGGAAGAAGCTGACTAAAGAAGGCGCCAAAGCCTTAAATTGTGCAAAAGATACT
 S  E  E  E  A  D
             3070                                    3090                                    3110
GTTGCTATGATGTAACTGCATTTGACCTAACCACTGCGAAAATTCATTCCGCTGTAATGT
             3130                                    3150                                    3170
TTTCACAATATTTAAAGCAGAAGCACGTCAGTTAGGATTTCCTTCTGCATAAGGTTTTTT
             3190                                    3210                                    3230
TGTAGTGTAATGTCTTAATCATAGTCTACCATCAAATATTTAGGAGTATCTTTAATGTT
             3250                                    3270                                    3290
TAGATAGTATATTAGCAGCATGCAATAATTACATCATAAGTTCTCAAGCAGAGGCAGTCT
             3310                                    3330                                    3350
ATTGCAAGGACCTTCTTTGCTGCCAGTTATCATAGGCTGTGTTTAAGCTAGAAAACTGAAT
             3370                                    3390                                    3410
AGCAACACTGAATACTGTAGAAATGCACTTGCTCAGTAATACTTGAGTTGTTGCAATAT
             3430                                    3450                                    3470
TTGATTATCCATTGGTTGTTACAGAAAAATTCTTAACTGTAATTGATGGTTGTTGCCGT
             3490                                    3510                                    3530
AATAGTATATTGCCTGTATTTCTACCTGTAGTAATGGGCTTTATGTGCTAGATTTTAATA
```

FIG. 15H

```
      3550                            3570                            3590
TCCTTGAGCCTGGGCAAGTGCAGAAGTCTTTTTAAAAGAAACATGGTTTACTTGCACAAA
      3610                            3630                            3650
ACTGATCAGTTTTGAGAGATCGTTAATGCCCTTGAAGTGGTTTTTGTGGGTGTGAAACAA
      3670                            3690                            3710
ATGGTGAGAATTTGAATTGGTCCCTCCTATTATAGTATTGAAATTAAGTCTACTTAATTT
      3730                            3750                            3770
ATCAAGTCATGTTCATGCCCTGATTTTATATACTTGTATCTATCAATAAACATTGTGATA
      3790                            3810
CTTGAAAAAAAAAAAAAAAAAAAAAAAAAAAAAAAAAAAGGGAATTC
```

FIG. 15I

SEQUENCE LISTING

```
(1) GENERAL INFORMATION:

(iii) NUMBER OF SEQUENCES: 7

(2) INFORMATION FOR SEQ ID NO:1:

(i) SEQUENCE CHARACTERISTICS:
         (A) LENGTH:309 base pairs
         (B) TYPE:nucleic acid
         (C) STRANDEDNESS:Double
         (D) TOPOLOGY:Linear (ii) MOLECULE TYPE:Genomic DNA (iii) HYPOTHETICAL:  No (iv) ANTI-SENSE:  No (v) FRAGMENT TYPE:Not applicable (vi) ORIGINAL SOURCE:
         (A) ORGANISM:  homo sapiens
         (B) STRAIN:  not applicable
         (C) INDIVIDUAL ISOLATE:  not applicable
         (D) DEVELOPMENTAL STAGE:  not applicable
         (E) HAPLOTYPE:  not applicable
         (F) TISSUE TYPE:  blood
         (G) CELL TYPE:  leucocyte
         (H) CELL LINE:  HeLa
         (I) ORGANELLE:  not applicable (vii) IMMEDIATE SOURCE:
         (A) LIBRARY:  not applicable
         (B) CLONE:  not applicable (viii) POSITION IN GENOME:
         (A) CHROMOSOME/SEGMENT: not applicable
         (B) MAP POSITION: not applicable
         (C) UNITS:  not applicable (ix) FEATURE:
         (A) NAME/KEY:  SEQ ID NO.1 is the sequence
             in Claim 1(i) starting at triplet 160-162 and ending at
             the triplet 466-468
         (B) LOCATION:  not available
         (C) IDENTIFICATION METHOD:  experiment-
``` in specification
      (D) OTHER INFORMATION: prevention of IFN-2
          promoted cell death (x) PUBLICATION INFORMATION: not available (xi) SEQUENCE DESCRIPTION: SEQ ID. NO: 1:

| | | | | | | | | | | | | | | | | |
|---|---|---|---|---|---|---|---|---|---|---|---|---|---|---|---|---|
| ATG | TCT | TCG | CCT | CCC | GAA | GGG | AAA | CTA | GAG | ACT | AAA | GCT | GGA | CAC | CCG | 48 |
| Met | Ser | Ser | Pro | Pro | Glu | Gly | Lys | Leu | Gly | Thr | Lys | Ala | Gly | His | Pro | |
| | | | | 5 | | | | | 10 | | | | | 15 | | |
| CCC | GCC | GTG | AAA | GCT | GGT | GGA | ATG | CGA | ATT | GTG | GAG | AAA | CAC | CCA | CAT | 96 |
| Pro | Ala | Val | Lys | Ala | Gly | Gly | Met | Arg | Ile | Val | Gln | Lys | His | Pro | His | |
| | | | 20 | | | | | 25 | | | | | 30 | | | |
| ACA | GGA | GAC | ACC | AAA | GAA | GAG | AAA | GAC | AAG | GAT | GAC | CAG | GAA | TGG | GAA | 144 |
| Thr | Glu | Asp | Thr | Lys | Glu | Glu | Lys | Asp | Lys | Asp | Asp | Gln | Glu | Trp | Glu | |
| | | | 35 | | | | | 40 | | | | | 45 | | | |
| AGC | CCC | AGT | CCA | CCT | AAA | CCC | ACT | GTG | TTC | ATC | TCT | GGG | GTC | ATC | GCC | 192 |
| Ser | Pro | Ser | Pro | Pro | Lys | Pro | Thr | Val | Phe | Ile | Ser | Gly | Val | Ile | Ala | |
| | 50 | | | | | 55 | | | | | 60 | | | | | |
| CGG | GGT | GAC | AAA | GAT | TTC | CCC | CCG | GCG | GCT | GCG | CAG | GTG | GCT | CAC | CAG | 240 |
| Arg | Gly | Asp | Lys | Asp | Phe | Pro | Pro | Ala | Ala | Ala | Gln | Val | Ala | His | Gln | |
| 65 | | | | | 70 | | | | | 75 | | | | | 80 | |
| AAG | CCG | CAT | GCC | TCC | ATG | GAC | AAG | CAT | CCT | TCC | CCA | AGA | ACC | CAG | CAC | 288 |
| Lys | Pro | His | Ala | Ser | Met | Asp | Lys | His | Pro | Ser | Pro | Arg | Thr | Gln | His | |
| | | | | 85 | | | | | 90 | | | | | 95 | | |
| ATC | CAG | CAG | CCA | CGC | AAG | TGA | | | | | | | | | | 309 |
| Ile | Gln | Gln | Pro | Arg | Lys | | | | | | | | | | | |
| | | | | 100 | | | | | | | | | | | | |

(2) INFORMATION FOR SEQ ID NO:2:

(i) SEQUENCE CHARACTERISTICS:
        (A) LENGTH:531 base pair
        (B) TYPE:nucleic acid
        (C) STRANDEDNESS: double
        (D) TOPOLOGY:linear (ii) MOLECULE TYPE:Genomic DNA (iii) HYPOTHETICAL: No (iv) ANTI-SENSE: No (v) FRAGMENT TYPE:Not applicable (vi) ORIGINAL SOURCE:
        (A) ORGANISM: homo sapiens
        (B) STRAIN: not applicable
        (C) INDIVIDUAL ISOLATE: not applicable
        (D) DEVELOPMENTAL STAGE: not applicable
        (E) HAPLOTYPE: not applicable
        (F) TISSUE TYPE: blood
        (G) CELL TYPE: Leucocyte
        (H) CELL LINE: HeLa
        (I) ORGANELLE: not applicable (vii) IMMEDIATE SOURCE:
        (A) LIBRARY: not applicable
        (B) CLONE: not applicable (viii) POSITION IN GENOME:
        (A) CHROMOSOME/SEGMENT: not applicable
        (B) MAP POSITION: not applicable
        (C) UNITS: not applicable (ix) FEATURE:
        (A) NAME/KEY: SEQ ID. NO: 2 is the
            sequence in Claim 1(ii) starting at triplet in
            position 287-289 and ending at position 816-818
            triplet 466-468
        (B) LOCATION: not available
        (C) IDENTIFICATION METHOD: experimentin specification
        (D) OTHER INFORMATION: prevention of IFN-2
            promoted cell death (x) PUBLICATION INFORMATION: not available (xi) SEQUENCE DESCRIPTION: SEQ ID. NO: 2:

```
ATG ACC AGG AAT GGG AAA GCC CCA GTC CAC CTA AAC CCA CTG TGT TCA        48
Met Thr Arg Asn Gly Lys Ala Pro Val His Leu Asn Pro Leu Cys Ser
              5                  10                  15

TCT CTG GGG TCA TCG CCC GGG GTG ACA AAG ATT TCC CCC CGG CGG CTG        96
Ser Leu Gly Ser Ser Pro Gly Val Thr Lys Ile Pro Pro Arg Arg Leu
             20                  25                  30

CGC AGG TGG CTC ACC AGA AGC CGC ATG CCT CCA TGG ACA AGC ATC CTT       144
Arg Arg Trp Leu Thr Arg Ser Arg Met Pro Pro Trp Thr Ser Ile Leu
             35                  40                  45

CCC CAA GAA CCC AGC ACA TCC AGC AGC CAC GCA AGT GAG CCT GGA GTC       192
Pro Gln Glu Pro Ser Thr Ser Ser Ser His Ala Ser Glu Pro Gly Val
 50                  55                  60

CAC CAG CCT GCC CCA TGG CCC CGG CTC TGC TGC ACT TGG TAT TTC CCT       240
His Gln Pro Ala Pro Trp Pro Arg Leu Cys Cys Thr Trp Tyr Phe Pro
 65                  70                  75                  80

GAC AGA GAG AAC CAG CAG TTT CGC CCA AAT CCT ACT CTG CTG GGA AAT       288
Asp Arg Glu Asn Gln Gln Phe Arg Pro Asn Pro Thr Leu Leu Gly Asn
             85                  90                  95

CTA AGG CAA AAC CAA GTG CTC TGT CCT TTG CCT TAC ATT TCC ATA TTT       336
Leu Arg Gln Asn Gln Val Leu Cys Pro Leu Pro Tyr Ile Ser Ile Phe
             100                 105                 110

AAA ACT AGA AAC AGC TTC AGC CCA AAC CTT GTT TAT GGG GAG TCT GGT       384
Lys Thr Arg Asn Ser Phe Ser Pro Asn Leu Val Tyr Gly Glu Ser Gly
             115                 120                 125

TGC ATG TCA TTT GAG GAT CAT TGT GCC CCT AGA GGT GCC ATT AGC AGA       432
Trp Met Ser Phe Glu Asp His Cys Ala Pro Arg Gly Ala Ile Ser Arg
 130                 135                 140

ATT TGC CAA GAT CCG AGA AAA ATT TTA GCT TTA GTT CTA TTT CAG CAG       480
Ile Cys Gln Asp Pro Arg Lys Ile Leu Ala Leu Val Leu Phe Gln Gln
 145                 150                 155                 160

TCA CCT GAC GTC CTT GTC TAT GGT CTT AAA AAC AAG AAG GCA CAC ATT       528
Ser Pro Asp Val Leu Val Tyr Gly Leu Lys Asn Lys Lys Ala His Ile
             165                 170                 175

TGA                                                                   531
```

(2) INFORMATION FOR SEQ ID NO:3:

(i) SEQUENCE CHARACTERISTICS:
        (A) LENGTH: 4935 base pairs
        (B) TYPE:nucleic acid
        (C) STRANDEDNESS: double
        (D) TOPOLOGY:linear (ii) MOLECULE TYPE:Genomic DNA (iii) HYPOTHETICAL: No (iv) ANTI-SENSE: No (v) FRAGMENT TYPE:Not applicable (vi) ORIGINAL SOURCE:
        (A) ORGANISM: homo sapiens
        (B) STRAIN: not applicable
        (C) INDIVIDUAL ISOLATE: not applicable
        (D) DEVELOPMENTAL STAGE: not applicable
        (E) HAPLOTYPE: not applicable
        (F) TISSUE TYPE: blood
        (G) CELL TYPE: Leucocyte
        (H) CELL LINE: HeLa

```
             (I) ORGANELLE:   not applicable (vii) IMMEDIATE SOURCE:
             (A) LIBRARY:  not applicable
             (B) CLONE:  not applicable (viii) POSITION IN GENOME:
             (A) CHROMOSOME/SEGMENT: not applicable
             (B) MAP POSITION: not applicable
             (C) UNITS:  not applicable (ix) FEATURE:
             (A) NAME/KEY:  Seq. ID. NO.: 3 is
                 the sequence in claim 1(iii) as Figure 8 of the
                 specification
             (B) LOCATION:  not available
             (C) IDENTIFICATION METHOD: experiment-
                 in specification
             (D) OTHER INFORMATION: prevention of IFN-2
                 promoted cell death (x) PUBLICATION INFORMATION:  not available (xi) SEQUENCE DESCRIPTION: SEQ ID. NO:   3:

CGGAGGACAG CCGGACCGAG CCAACGCCGG GGACTTTGTT CCCTCCACGG AGGGGACTCG         60

GCAACTCGCA GCGGCAGGGT CTGGGGCCGG CGCCTGGGAG GGATCTGCGC CCCCCACTCA        120

CTCCCTAGCT GTGTTCCCGC CGCCGCCCCG GCTAGTCTCC GGCGCTGGCG CCTATGGTCG        180

GCCTCCGACA GCGCTCCGGA GGGACCGGGG GAGCTCCCAG GCGCCCGGGA CTGGAGACTG        240

ATGCATGAGG GGCCTACGGA GGCGCAGGAG CGGTGGTGAT GGTCTGGGAA GCGGAGCTGA        300

AGTCCCCTGG GCTTTGGTGA GGCGTGACAG TTTATC ATG ACC GTG TTC AGG CAG         354
                                         Met Thr Val Phe Arg Gln
                                                             5

GAA AAC GTG GAT GAT TAC TAC GAC ACC GGC GAG GAA CTT GGC AGT GGA         402
Glu Asn Val Asp Asp Tyr Tyr Asp Thr Gly Glu Glu Leu Gly Ser Gly
          10                  15                  20

CAG TTT GCG GTT GTG AAG AAA TGC CGT GAG AAA AGT ACC GGC CTC CAG         450
Gln Phe Ala Val Val Lys Lys Cys Arg Glu Lys Ser Thr Gly Leu Gln
        25                  30                  35

TAT CCC GCC AAA TTC ATC AAG AAA AGG AGG ACT AAG TCC AGC CGG CGG         498
Tyr Pro Ala Lys Phe Ile Lys Lys Arg Arg Thr Lys Ser Ser Arg Arg
    40                  45                  50

GGT GTG AGC CGC GAG GAC ATC GAG CGG GAG GTC AGC ATC CTG AAG GAG         546
Gly Val Ser Arg Glu Asp Ile Glu Arg Glu Val Ser Ile Leu Lys Glu
55                  60                  65                  70

ATC CAG CAC CCC AAT GTC ATC ACC CTG CAC GAG GTC TAT GAG AAC AAG         594
Ile Gln His Pro Asn Val Ile Thr Leu His Glu Val Tyr Glu Asn Lys
                75                  80                  85

ACG GAC GTC ATC CTG ATC TTG GAA CTC GTT GCA GGT GGC GAG CTG TTT         642
Thr Asp Val Ile Leu Ile Leu Glu Leu Val Ala Gly Gly Glu Leu Phe
            90                  95                 100

GAC TTC TTA GCT GAA AAG GAA TCT TTA ACT GAA GAG GAA GCA ACT GAA         690
Asp Phe Leu Ala Glu Lys Glu Ser Leu Thr Glu Glu Glu Ala Thr Glu
        105                 110                 115

TTT CTC AAA CAA ATT CTT AAT GGT GTT TAC TAC CTG CAC TCC CTT CAA         738
Phe Leu Lys Gln Ile Leu Asn Gly Val Tyr Tyr Leu His Ser Leu Gln
    120                 125                 130

ATC GCC CAC TTT GAT CTT AAG CCT GAG AAC ATA ATG CTT TTG GAT AGA         786
Ile Ala His Phe Asp Leu Lys Pro Glu Asn Ile Met Leu Leu Asp Arg
135                 140                 145                 150

AAT GTC CCC AAA CCT CGG ATC AAG ATC ATT GAC TTT GGA AAT GAA TTT         834
Asn Val Pro Lys Pro Arg Ile Lys Ile Ile Asp Phe Gly Asn Glu Phe
                155                 160                 165

AAA AAC ATA TTT GGG ACT CCA GAG TTT GTC GCT CCT GAG ATA GTC AAC         882
```

```
Lys Asn Ile Phe Gly Thr Pro Glu Phe Val Ala Pro Glu Ile Val Asn
                170                 175                 180

TAT GAA CCT CTT GGT CTT GAG GCA GAT ATG TGG AGT ATC GGG GTA ATA         930
Tyr Glu Pro Leu Gly Leu Glu Ala Asp Met Trp Ser Ile Gly Val Ile
            185                 190                 195

ACC TAT ATC CTC CTA AGT GGG GCC TCC CCA TTT CTT GGA GAC ACT AAG         978
Thr Tyr Ile Leu Leu Ser Gly Ala Ser Pro Phe Leu Gly Asp Thr Lys
        200                 205                 210

CAA GAA ACG TTA GCA AAT GTA TCC GCT GTC AAC TAC GAA TTT GAG GAT        1026
Gln Glu Thr Leu Ala Asn Val Ser Ala Val Asn Tyr Glu Phe Glu Asp
215                 220                 225                 230

GAA TAC TTC AGT AAT ACC AGT GCC CTA GCC AAA GAT TTC ATA AGA AGA        1074
Glu Tyr Phe Ser Asn Thr Ser Ala Leu Ala Lys Asp Phe Ile Arg Arg
                235                 240                 245

CTT CTG GTC AAG GAT CCA AAG AAG AGA ATG ACA ATT CAA GAT AGT TTG        1122
Leu Leu Val Lys Asp Pro Lys Lys Arg Met Thr Ile Gln Asp Ser Leu
            250                 255                 260

CAG CAT CCC TGG ATC AAG CCT AAA GAT ACA CAA CAG GCA CTT AGT AGA        1170
Gln His Pro Trp Ile Lys Pro Lys Asp Thr Gln Gln Ala Leu Ser Arg
        265                 270                 275

AAA GCA TCA GCA GTA AAC ATG GAG AAA TTC AAG AAG TTT GCA GCC CGG        1218
Lys Ala Ser Ala Val Asn Met Glu Lys Phe Lys Lys Phe Ala Ala Arg
280                 285                 290

AAA AAA TGG AAA CAA TCC GTT CGC TTG ATA TCA CTG TGC CAA AGA TTA        1266
Lys Lys Trp Lys Gln Ser Val Arg Leu Ile Ser Leu Cys Gln Arg Leu
295                 300                 305                 310

TCC AGG TCA TTC CTG TCC AGA AGT AAC ATG AGT GTT GCC AGA AGC GAT        1314
Ser Arg Ser Phe Leu Ser Arg Ser Asn Met Ser Val Ala Arg Ser Asp
                315                 320                 325

GAT ACT CTG GAT GAG GAA GAC TCC TTT GTG ATG AAA GCC ATC ATC CAT        1362
Asp Thr Leu Asp Glu Glu Asp Ser Phe Val Met Lys Ala Ile Ile His
            330                 335                 340

GCC ATC AAC GAT GAC AAT GTC CCA GGC CTG CAG CAC CTT CTG GGC TCA        1410
Ala Ile Asn Asp Asp Asn Val Pro Gly Leu Gln His Leu Leu Gly Ser
        345                 350                 355

TTA TCC AAC TAT GAT GTT AAC CAA CCC AAC AAG CAC GGG ACA CCT CCA        1458
Leu Ser Asn Tyr Asp Val Asn Gln Pro Asn Lsy His Gly Thr Pro Pro
360                 365                 370

TTA CTC ATT GCT GCT GGC TGT GGG AAT ATT CAA ATA CTA CAG TTG CTC        1506
Leu Leu Ile Ala Ala Gly Cys Gly Asn Ile Gln Ile Leu Gln Leu Leu
375                 380                 385                 390

ATT AAA AGA GGC TCG AGA ATC GAT GTC CAG GAT AAG GGC GGG TCC AAT        1554
Ile Lys Arg Gly Ser Arg Ile Asp Val Gln Asp Lys Gly Gly Ser Asn
                395                 400                 405

GCC GTC TAC TGG GCT GCT CGG CAT GGC CAC GTC GAT ACC TTG AAA TTT        1602
Ala Val Tyr Trp Ala Ala Arg His Gly His Val Asp Thr Leu Lys Phe
            410                 415                 420

CTC AGT GAG AAC AAA TGC CCT TTG GAT GTG AAA GAC AAG TCT GGA GAG        1650
Leu Ser Gly Asn Lys Cys Pro Leu Asp Val Lys Asp Lys Ser Gly Glu
        425                 430                 435

ATG GCC CTC CAC GTG GCA GCT CGC TAT GGC CAT GCT GAC GTG GCT CAA        1698
Met Ala Leu His Val Ala Ala Arg Tyr Gly His Ala Asp Val Ala Gln
            440                 445                 450

GTT ACT TGT GCA GCT TCG GCT CAA ATC CCA ATA TCC AGG ACA AAG GAA        1746
Val Thr Cys Ala Ala Ser Ala Gln Ile Pro Ile Ser Arg Thr Lys Glu
455                 460                 465                 470

GAA GAA ACC CCC CTG CAC TGT GCT GCT TGG CAC GGC TAT TAC TCT GTG        1794
Glu Glu Thr Pro Leu His Cys Ala Ala Trp His Gly Tyr Tyr Ser Val
                475                 480                 485

GCC AAA GCC CTT TGT GAA GCC GGC TGT AAC GTG AAC ATC AAG AAC CGA        1842
```

```
              Ala Lys Ala Leu Cys Glu Ala Gly Cys Asn Val Asn Ile Lys Asn Arg
                      490                 495                 500

GAA GGA GAG ACG CCC CTC CTG ACA GCC TCT GCC AGG GGC TAC CAC GAC              1890
Glu Gly Glu Thr Pro Leu Leu Thr Ala Ser Ala Arg Gly Tyr His Asp
            505                 510                 515

ATC GTG GAG TGT CTG GCC GAA CAT GGA GCC GAC CTT AAT GCT TGC GAC              1938
Ile Val Glu Cys Leu Ala Glu His Gly Ala Asp Leu Asn Ala Cys Asp
        520                 525                 530

AAG GAC GGA CAC ATT GCC CTT CAT CTG GCT GTA AGA CGG TGT CAG ATG              1986
Lys Asp Gly His Ile Ala Leu His Leu Ala Val Arg Arg Cys Gln Met
535                 540                 545                 550

GAG GTA ATC AAG ACT CTC CTC AGC CAA GGG TGT TTC GTC GAT TAT CAA              2034
Glu Val Ile Lys Thr Leu Leu Ser Gln Gly Cys Phe Val Asp Tyr Gln
                555                 560                 565

GAC AGG CAC GGC AAT ACT CCC CTC CAT GTG GCA TGT AAA GAT GGC AAC              2082
Asp Arg His Gly Asn Thr Pro Leu His Val Ala Cys Lys Asp Gly Asn
            570                 575                 580

ATG CCT ATC GTG GTG GCC CTC TGT GAA GCA AAC TGC AAT TTG GAC ATC              2130
Met Pro Ile Val Val Ala Leu Cys Glu Ala Asn Cys Asn Leu Asp Ile
        585                 590                 595

TCC AAC AAG TAT GGG CGA ACG CCT CTG CAC CTT GCG GCC AAC AAC GGA              2178
Ser Asn Lys Tyr Gly Arg Thr Pro Leu His Leu Ala Ala Asn Asn Gly
    600                 605                 610

ATC CTA GAC GTG GTC CGG TAT CTC TGT CTG ATG GGA GCC AGC GTT GAG              2226
Ile Leu Asp Val Val Arg Tyr Leu Cys Leu Met Gly Ala Ser Val Glu
615                 620                 625                 630

GCG CTG ACC ACG GAC GGA AAG ACG GCA GAA GAT CTT GCT AGA TCG GAA              2274
Ala Leu Thr Thr Asp Gly Lys Thr Ala Glu Asp Leu Ala Arg Ser Glu
                635                 640                 645

CAG CAC GAG CAC GTA GCA GGT CTC CTT GCA AGA CTT CGA AAG GAT ACG              2322
Gln His Glu His Val Ala Gly Leu Leu Ala Arg Leu Arg Lys Asp Thr
            650                 655                 660

CAC CGA GGA CTC TTC ATC CAG CAG CTC CGA CCC ACA CAG AAC CTG CAG              2370
His Arg Gly Leu Phe Ile Gln Gln Leu Arg Pro Thr Gln Asn Leu Gln
        665                 670                 675

CCA AGA ATT AAG CTC AAG CTG TTT GGC CAC TCG GGA TCC GGG AAA ACC              2418
Pro Arg Ile Lys Leu Lys Leu Phe Gly His Ser Gly Ser Gly Lys Thr
    680                 685                 690

ACC CTT GTA GAA TCT CTC AAG TGT GGG CTG CTG AGG AGC TTT TTC AGA              2466
Thr Leu Val Glu Ser Leu Lys Cys Gly Leu Leu Arg Ser Phe Phe Arg
695                 700                 705                 710

AGG CGT CGG CCC AGA CTG TCT TCC ACC AAC TCC AGC AGG TTC CCA CCT              2514
Arg Arg Arg Pro Arg Leu Ser Ser Thr Asn Ser Ser Arg Phe Pro Pro
                715                 720                 725

TCA CCC CTG GCT TCT AAG CCC ACA GTC TCA GTG AGC ATC AAC AAC CTG              2562
Ser Pro Leu Ala Ser Lys Pro Thr Val Ser Val Ser Ile Asn Asn Leu
            730                 735                 740

TAC CCA GGC TGC GAG AAC GTG AGT GTG AGG AGC CGC AGC ATG ATG TTC              2610
Tyr Pro Gly Cys Glu Asn Val Ser Val Arg Ser Arg Ser Met Met Phe
        745                 750                 755

GAG CCG GGT CTT ACC AAA GGG ATG CTG GAG GTG TTT GTG GCC CCG ACC              2658
Glu Pro Gly Leu Thr Lys Gly Met Leu Glu Val Phe Val Ala Pro Thr
    760                 765                 770

CAC CAC CCG CAC TGC TCG GCC GAT GAC CAG TCC ACC AAG GCC ATC GAC              2706
His His Pro His Cys Ser Ala Asp Asp Gln Ser Thr Lys Ala Ile Asp
775                 780                 785                 790

ATC CAG AAC GCT TAT TTG AAT GGA GTT GGC GAT TTC AGC GTG TGG GAG              2754
Ile Gln Asn Ala Tyr Leu Asn Gly Val Gly Asp Phe Ser Val Trp Glu
                795                 800                 805

TTC TCT GGA AAT CCT GTG TAT TTC TGC TGT TAT GAC TAT TTT GCT GCA              2802
```

```
                                                                -continued

Phe Ser Gly Asn Pro Val Tyr Phe Cys Cys Tyr Asp Tyr Phe Ala Ala
        810                 815                 820

AAT GAT CCC ACG TCA ATC CAT GTT GTT GTC TTT AGT CTA GAA GAG CCC         2850
Asn Asp Pro Thr Ser Ile His Val Val Val Phe Ser Leu Glu Glu Pro
            825                 830                 835

TAT GAG ATC CAG CTG AAC CCA GTG ATT TTC TGG CTC AGT TTC CTG AAG         2898
Tyr Glu Ile Gln Leu Asn Pro Val Ile Phe Trp Leu Ser Phe Leu Cys
        840                 845                 850

TCC CTT GTC CCA GTT GAA GAA CCC ATA GCC TTC GGT GGC AAG CTG AAG         2946
Ser Leu Val Pro Val Glu Glu Pro Ile Ala Phe Gly Gly Cys Leu Lys
855                 860                 865                 870

AAC CCA CTC CAA GTT GTC CTG GTG GCC ACC CAC GCT GAC ATC ATG AAT         2994
Asn Pro Leu Gln Val Val Leu Val Ala Thr His Ala Asp Ile Met Asn
            875                 880                 885

GTT CCT CGA CCG GCT GGA GGC GAG TTT GGA TAT GAC AAA GAC ACA TCG         3042
Val Pro Arg Pro Ala Gly Gly Glu Phe Gly Tyr Asp Lys Asp Thr Ser
        890                 895                 900

TTG CTG AAA GAG ATT AGG AAC AGG TTT GGA AAT GAT CTT CAC ATT TCA         3090
Leu Leu Lys Glu Ile Arg Asn Arg Phe Gly Asn Asp Leu His Ile Ser
            905                 910                 915

AAT AAG CTG TTT GTT CTG GAT GCT GGG GCT TCT GGG TCA AAG GAC ATG         3138
Asn Lys Leu Phe Val Leu Asp Ala Gly Ala Ser Gly Ser Lys Asp Met
        920                 925                 930

AAG GTA CTT CGA AAT CAT CTG CAA GAA ATA CGA AGC CAG ATT GTT TCG         3186
Lys Val Leu Arg Asn His Leu Gln Glu Ile Arg Ser Gln Ile Val Ser
935                 940                 945                 950

GTC TGT CCT CCC ATG ACT CAC CTG TGT GAG AAA ATC ATC TCC ACG CTG         3234
Val Cys Pro Pro Met Thr His Leu Cys Glu Lys Ile Ile Ser Thr Leu
            955                 960                 965

CCT TCC TGG AGG AAG CTC AAT GGA CCC AAC CAG CTG ATG TCG CTG CAG         3282
Pro Ser Trp Arg Lys Leu Asn Gly Pro Asn Gln Leu Met Ser Leu Gln
        970                 975                 980

CAG TTT GTG TAC GAC GTG CAG GAC CAG CTG AAC CCC CTG GCC AGC GAG         3330
Gln Phe Val Tyr Asp Val Gln Asp Gln Leu Asn Pro Leu Ala Ser Glu
985                 990                 995                 1000

GAG GAC CTC AGG CGC ATT GCT CAG CAG CTC CAC AGC ACA GGC GAG ATC         3378
Glu Asp Leu Arg Arg Ile Ala Gln Gln Leu His Ser Thr Gly Glu Ile
                1005                1010                1015

AAC ATC ATG CAA AGT GAA ACA GTT CAG GAC GTG CTG CTC CTG GAC CCC         3426
Asn Ile Met Gln Ser Glu Thr Val Gln Asp Val Leu Leu Leu Asp Pro
            1020                1025                1030

CGC TGG CTC TGC ACA AAC GTC CTG GGG AAG TTG CTG TCC GTG GAG ACC         3474
Arg Trp Leu Cys Thr Asn Val Leu Gly Lys Leu Leu Ser Val Glu Thr
        1035                1040                1045

CCA CGG GCG CTG CAC CAC TAC CGG GGC CGC TAC ACC GTG GAG GAC ATC         3522
Pro Arg Ala Leu His His Tyr Arg Gly Arg Tyr Thr Val Glu Asp Ile
    1050                1055                1060

CAG CGC CTG GTG CCC GAC AGC GAC GTG GAG GAG CTG CTG CAG ATC CTC         3570
Gln Arg Leu Val Pro Asp Ser Asp Val Glu Glu Leu Leu Gln Ile Leu
1065                1070                1075                1080

GAT GCC ATG GAC ATC TGC GCC CGG GAC CTG AGC AGC GGG ACC ATG GTG         3618
Asp Ala Met Asp Ile Cys Ala Arg Asp Leu Ser Ser Gly Thr Met Val
                1085                1090                1095

GAC GTC CCA GCC CTG ATC AAG ACA GAC AAC CTG CAC CGC TCC TGG GCT         3666
Asp Val Pro Ala Leu Ile Lys Thr Asp Asn Leu His Arg Ser Trp Ala
            1100                1105                1110

GAT GAG GAG GAC GAG GTG ATG GTG TAT GGT GGC GTG CGC ATC GTG CCC         3714
Asp Glu Glu Asp Glu Val Met Val Tyr Gly Gly Val Arg Ile Val Pro
        1115                1120                1125

GTG GAA CAC CTC ACC CCC TTC CCA TGT GGC ATC TTT CAC AAG GTC CAG         3762
```

-continued

| | |
|---|---|
| Val Glu His Leu Thr Pro Phe Phe Cys Gly Ile Phe His Lys Val Gln<br>1130    1135    1140    1045 | |
| GTG AAC CTG TGC CGG TGG ATC CAC CAG CAA AGC ACA GAG GGC GAC GCG<br>Val Asn Leu Cys Arg Trp Ile His Gln Gln Ser Thr Glu Gly Asp Ala<br>    1150    1155    1160 | 3810 |
| GAC ATC CGC CTG TGG GTG AAT GGC TGC AAG CTG GCC AAC CGT GGG GCC<br>Asp Ile Arg Leu Trp Val Asn Gly Cys Lys Leu Ala Asn Arg Gly Ala<br>    1165    1170    1175 | 3858 |
| GAG CTG CTG GTG CTG CTG GTC AAC CAC GGC CAG GGC ATT GAG GTC CAG<br>Glu Leu Leu Val Leu Leu Val Asn His Gly Gln Gly Ile Glu Val Gln<br>    1180    1185    1190 | 3906 |
| GTC CGT GGC CTG GAG ACG GAG AAG ATC AAG TGC TGC CTG CTG CTG GAC<br>Val Arg Gly Leu Glu Thr Glu Lys Ile Lys Cys Cys Leu Leu Leu Asp<br>    1195    1200    1205 | 3954 |
| TCG GTG TGC AGC ACC ATT GAG AAC GTC ATG GCC ACC ACG CTG CCA GGG<br>Ser Val Cys Ser Thr Ile Glu Asn Val Met Ala Thr Thr Leu Pro Gly<br>1210    1215    1220    1225 | 4002 |
| CTC CTG ACC GTG AAG CAT TAC CTG AGC CCC CAG CAG CTG CGG GAG CAC<br>Leu Leu Thr Val Lys His Tyr Leu Ser Pro Gln Gln Leu Arg Glu His<br>    1230    1235    1240 | 4050 |
| CAT GAG CCC GTC ATG ATC TAC CAG CCA CGG GAC TTC TTC CGG GCA CAG<br>His Glu Pro Val Met Ile Tyr Gln Pro Arg Asp Phe Phe Arg Ala Gln<br>    1240    1245    1250 | 4098 |
| ACT CTG AAG GAA ACC TCA CTG ACC AAC ACC ATG GGG GGG TAC AAG GAA<br>Thr Leu Lys Glu Thr Ser Leu Thr Asn Thr Met Gly Gly Tyr Lys Glu<br>    1255    1260    1265 | 4146 |
| AGC TTC AGC AGC ATC ATG TGC TTC GGG TGT CAC GAC GTC TAC TCA CAG<br>Ser Phe Ser Ser Ile Met Cys Phe Gly Cys His Asp Val Tyr Ser Gln<br>1270    1275    1280 | 4194 |
| GCC AGC CTC GGC ATG GAC ATC CAT GCA TCA GAC CTG AAC CTC CTC ACT<br>Ala Ser Leu Gly Met Asp Ile His Ala Ser Asp Leu Asn Leu Leu Thr<br>1285    1290    1295    1300 | 4242 |
| CGG AGG AAA CTG AGT CGC CTG CTG GAC CCG CCC GAC CCC CTG GGG AAG<br>Arg Arg Lys Leu Ser Arg Leu Leu Asp Pro Pro Asp Pro Leu Gly Lys<br>    1305    1310    1315 | 4290 |
| GAC TGG TGC CTT CTC GCC ATG AAC TTA GGC CTC CCT GAC CTC GTG GCA<br>Asp Trp Cys Leu Leu Ala Met Asn Leu Gly Leu Pro Asp Leu Val Ala<br>    1320    1325    1330 | 4338 |
| AAG TAC AAC ACC AAT AAC GGG GCT CCC AAG GAT TTC CTC CCC AGC CCC<br>Lys Tyr Asn Thr Asn Asn Gly Ala Pro Lys Asp Phe Leu Pro Ser Pro<br>    1335    1340    1345 | 4386 |
| CTC CAC GCC CTG CTG CGG GAA TGG ACC ACC TAC CCT GAG AGC ACA GTG<br>Leu His Ala Leu Leu Arg Glu Trp Thr Thr Tyr Pro Glu Ser Thr Val<br>    1350    1355    1360 | 4434 |
| GGC ACC CTC ATG TCC AAA CTG AGG GAG CTG GGT CGC CGG GAT GCC GCA<br>Gly Thr Leu Met Ser Lys Leu Arg Glu Leu Gly Arg Arg Asp Ala Ala<br>1365    1370    1375    1380 | 4482 |
| GAC CTT TTG CTG AAG GCA TCC TCT GTG TTC AAA ATC AAC CTG GAT GGC<br>Asp Leu Leu Leu Lys Ala Ser Ser Val Phe Lys Ile Asn Leu Asp Gly<br>    1385    1390    1395 | 4530 |
| AAT GGC CAG GAG GCC TAT GCC TCG AGC TGC AAC AGC GGC ACC TCT TAC<br>Asn Gly Gln Glu Ala Tyr Ala Ser Ser Cys Asn Ser Gly Thr Ser Tyr<br>    1400    1405    1410 | 4578 |
| AAT TCC ATT AGC TCT GTT GTA TCC CGG TGAGGGCAGC CTCTGGCTTG GACAGGGTCT<br>Asn Ser Ile Ser Ser Val Val Ser Arg<br>    1415    1420 | 4635 |
| GTTTGGACTG CAGAACCAAG GGGGTGATGT AGCCCATCCT TCCCTTTGGA GATGCTGAGG | 4695 |
| GTGTTTCTTC CTGCACCCAC AGCCAGGGGG ATGCCACTCC TCCCTCCGGC TTGACCTGTT | 4755 |
| TCTCTGCCGC TACCTCCCTC CCCGTCTCAT TCCGTTGTCT GTGGATGGTC ATTGCAGTTT | 4815 |

-continued

```
AAGAGCAGAA CAGATCTTTT ACTTTGGCCG CTTGAAAAGC TAGTGTACCT CCTCTCAGTG    4875

TTTTGGACTC CATCTCTCAT CCTCCAGTAC CTTGCTTCTT ACTGATAATT TTGCTGGAAT    4935
```

(2) INFORMATION FOR SEQ ID NO:4:

(i) SEQUENCE CHARACTERISTICS:
        (A) LENGTH:  1568 base pairs
        (B) TYPE:nucleic acid
        (C) STRANDEDNESS:Double
        (D) TOPOLOGY:Linear (ii) MOLECULE TYPE:Genomic DNA (iii) HYPOTHETICAL:  No (iv) ANTI-SENSE:  No (v) FRAGMENT TYPE:Not applicable (vi) ORIGINAL SOURCE:
        (A) ORGANISM:  homo sapiens
        (B) STRAIN:  not applicable
        (C) INDIVIDUAL ISOLATE:  not applicable
        (D) DEVELOPMENTAL STAGE:  not applicable
        (E) HAPLOTYPE:  not applicable
        (F) TISSUE TYPE:  blood
        (G) CELL TYPE:  Leucocyte
        (H) CELL LINE:  HeLa
        (I) ORGANELLE:  not applicable (vii) IMMEDIATE SOURCE:
        (A) LIBRARY:  not applicable
        (B) CLONE:  not applicable (viii) POSITION IN GENOME:
        (A) CHROMOSOME/SEGMENT: not applicable
        (B) MAP POSITION: not applicable
        (C) UNITS:  not applicable (ix) FEATURE:
        (A) NAME/KEY:  SEQ ID NO.: 4 is
            the sequence in claim 1(iv) starting at triplet
            position 74-76 and ending at triplet position
            1268-1270
        (B) LOCATION:not available
        (C) IDENTIFICATION METHOD:  experiment-
           in specification
        (D) OTHER INFORMATION:  prevention of IFN-2
           promoted cell death (x) PUBLICATION INFORMATION:  not available (xi) SEQUENCE DESCRIPTION:  SEQ  ID. NO: 4:

```
GAATTCCGCC GGCCCCAGGC AGCGTGTGTC GGTCGCCTAG GCTGGAGAAC TAGTCCTCGA     60

CTCACGTGCA AGG ATG ATG CTG AAA GGA ATA ACA AGG CTT ATC TCT AGG      109
            Met Met Leu Lys Gly Ile Thr Arg Leu Ile Ser Arg
                         5                  10

ATC CAT AAG TTG GAC CCT GGG CGT TTT TTA CAC ATG GGG ACC CAG GCT     157
Ile His Lys Leu Asp Pro Gly Arg Phe Leu His Met Gly Thr Gln Ala
         15                  20                  25

CGC CAA AGC ATT GCT GCT CAC CTA GAT AAC CAG GTT CCA GTT GAG AGT     205
Arg Gln Ser Ile Ala Ala His Leu Asp Asn Gln Val Pro Val Gly Ser
     30                  35                  40

CCG AGA GCT ATT TCC CGC ACC AAT GAG AAT GAC CCG GCC AAG CAT GGG     253
Pro Arg Ala Ile Ser Arg Thr Asn Gly Asn Asp Pro Ala Lys His Gly
 45                  50                  55                  60

GAT CAG CAC GAG GGT CAG CAC TAC AAC ATC TCC CCC CAG GAT TTG GAG     301
Asp Gln His Glu Gly Gln His Tyr Asn Ile Ser Pro Gln Asp Leu Glu
                 65                  70                  75

ACT GTA TTT CCC CAT GGC CTT CCT CCT CGC TTT GTG ATG CAG GTG AAG     349
```

```
            Thr Val Phe Pro His Gly Leu Pro Pro Arg Phe Val Met Gln Val Lys
                        80                  85                  90

ACA TTC AGT GAA GCT TGC CTG ATG GTA AGG AAA CCA GCC CTA GAA CTT                397
Thr Phe Ser Glu Ala Cys Leu Met Val Arg Lys Pro Ala Leu Glu Leu
            95                  100                 105

CTG CAT TAC CTG AAA AAC ACC AGT TTT GCT TAT CCA GCT ATA CGA TAT                445
Leu His Tyr Leu Lys Asn Thr Ser Phe Ala Tyr Pro Ala Ile Arg Tyr
        110                 115                 120

CTT CTG TAT GGA GAG AAG GGA ACA GGA AAA ACC CTA AGT CTT TGC CAT                493
Leu Leu Tyr Gly Glu Lys Gly Thr Gly Lys Thr Leu Ser Leu Cys His
125                 130                 135                 140

GTT ATT CAT TTC TGT GCA AAA CAG GAC TGG CTG ATA CTA CAT ATT CCA                541
Val Ile His Phe Cys Ala Lys Gln Asp Trp Leu Ile Leu His Ile Pro
                145                 150                 155

GAT GCT CAT CTT TGG GTG AAA AAT TGT CGG GAT CTT CTG CAG TCC AGC                589
Asp Ala His Leu Trp Val Lys Asn Cys Arg Asp Leu Leu Gln Ser Ser
            160                 165                 170

TAC AAC AAA CAG CGC TTT GAT CAA CCT TTA GAG GCT TCA ACC TGG CTG                637
Tyr Asn Lys Gln Arg Phe Asp Gln Pro Leu Glu Ala Ser Thr Trp Leu
        175                 180                 185

AAG AAT TTC AAA ACT ACA AAT GAG CGC TTC CTG AAC CAG ATA AAA GTT                685
Lys Asn Phe Lys Thr Thr Asn Glu Arg Phe Leu Asn Gln Ile Lys Val
    190                 195                 200

CAA GAG AAG TAT GTC TGG AAT AAG AGA GAA AGC ACT GAG AAA GGG AGT                733
Gln Glu Lys Tyr Val Trp Asn Lys Arg Glu Ser Thr Glu Lys Gly Ser
                205                 210                 215

CCT CTG GGA GAA GTG GTT GAA CAG GGC ATA ACA CGG GTG AGG AAC GCC                781
Pro Leu Gly Glu Val Val Glu Gln Gly Ile Thr Arg Val Arg Asn Ala
            220                 225                 230

ACA GAT GCA GTT GGA ATT GTG CTG AAA GAG CTA AAG AGG CAA AGT TCT                829
Thr Asp Ala Val Gly Ile Val Leu Lys Glu Leu Lys Arg Gln Ser Ser
        235                 240                 245

TTG GGT ATG TTT CAC CTC CTA GTG GCC GTG GAT GGA ATC AAT GCT CTT                877
Leu Gly Met Phe His Leu Leu Val Ala Val Asp Gly Ile Asn Ala Leu
250                 255                 260

TGG GGA AGA ACC ACT CTG AAA AGA GAA GAT AAA AGC CCG ATT GCC CCC                925
Trp Gly Arg Thr Thr Leu Lys Arg Glu Asp Lys Ser Pro Ile Ala Pro
265                 270                 275                 280

GAG GAA TTA GCA CTT GTT CAC AAC TTG AGG AAA ATG ATG AAA AAT GAT                973
Glu Glu Leu Ala Leu Val His Asn Leu Arg Lys Met Met Lys Asn Asp
                285                 290                 295

TGG CAT GGA GGC GCC ATT GTG TCG GCT TTG AGC CAG ACT GGG TCT CTC                1021
Trp His Gly Gly Ala Ile Val Ser Ala Leu Ser Gln Thr Gly Ser Leu
            300                 305                 310

TTT AAG CCC CGG AAA GCC TAT CTG CCC CAG GAG TTG CTG GGA AAG GAA                1069
Phe Lys Pro Arg Lys Ala Tyr Leu Pro Gln Glu Leu Leu Gly Lys Glu
        315                 320                 325

GGA TTT GAT GCC CTG GAT CCC TTT ATT CCC ATC CTG GTT TCC AAC TAT                1117
Gly Phe Asp Ala Leu Asp Pro Phe Ile Pro Ile Leu Val Ser Asn Tyr
330                 335                 340

AAC CCA AAG GAA TTT GAA AGT TGT ATT CAG TAT TAT TTG GAA AAC AAT                1165
Asn Pro Lys Glu Phe Glu Ser Cys Ile Gln Tyr Tyr Leu Glu Asn Asn
345                 350                 355                 360

TGG CTT CAA CAT GAG AAA GCT CCT ACA GAA GAA GGG AAA AAA GAG CTG                1213
Trp Leu Gln His Glu Lys Ala Pro Thr Glu Glu Gly Lys Lys Glu Leu
                365                 370                 375

CTG TTC CTA AGT AAC GCG AAC CCC TCG CTG CTG GAG CGG CAC TGT GCC                1261
Leu Phe Leu Ser Asn Ala Asn Pro Ser Leu Leu Glu Arg His Cys Ala
            380                 385                 390

TAC CTC TAA GCCAAGATCA CAGCATGTGA GGAAGACAGT GGACATCTGC TTTATGCTGG            1320
Tyr Leu
```

Tyr Leu Xaa
395

| | |
|---|---|
| ACCCAGTAAG ATGAGGAAGT CGGGCAGTAC ACAGGAAGAG GAGCCAGGCC CTTGTACCTA | 1380 |
| TGGGATTGGA CAGGACTGCA GTTGGCTCTG GACCTGCATT AAAATGGGTT TCACTGTGAA | 1440 |
| TGCGTGACAA TAAGATATTC CCTTGTTCCT AAAACTTTAT ATCAGTTTAT TGGATGTGGG | 1500 |
| TTTTTCACAT TTAAGATAAT TATGGCTCTT TTCCTAAAAA ATAAAATATC TTTCTAAAAA | 1560 |
| AAAAAAAA | 1568 |

(2) INFORMATION FOR SEQ ID NO: 5:

(i) SEQUENCE CHARACTERISTICS:
        (A) LENGTH: 132 base pair
        (B) TYPE: nucleic acid
        (C) STRANDEDNESS:Double
        (D) TOPOLOGY:Linear (ii) MOLECULE TYPE:Genomic DNA (iii) HYPOTHETICAL: No (iv) ANTI-SENSE: No (v) FRAGMENT TYPE:Not applicable (vi) ORIGINAL SOURCE:
        (A) ORGANISM: homo sapiens
        (B) STRAIN: not applicable
        (C) INDIVIDUAL ISOLATE: not applicable
        (D) DEVELOPMENTAL STAGE: not applicable
        (E) HAPLOTYPE: not applicable
        (F) TISSUE TYPE: blood
        (G) CELL TYPE: Leucocyte
        (H) CELL LINE: HeLa
        (I) ORGANELLE: not applicable (vii) IMMEDIATE SOURCE:
        (A) LIBRARY: not applicable
        (B) CLONE: not applicable (viii) POSITION IN GENOME:
        (A) CHROMOSOME/SEGMENT: not applicable
        (B) MAP POSITION: not applicable
        (C) UNITS: not applicable (ix) FEATURE:
        (A) NAME/KEY: SEQ ID NO.: 5 is the
            sequence in Claim 1(v) depicted in FIG. 13
        (B) LOCATION:not available
        (C) IDENTIFICATION METHOD: experiment-
           in specification
        (D) OTHER INFORMATION: prevention of IFN-2
           promoted cell death (x) PUBLICATION INFORMATION: not available (xi) SEQUENCE DESCRIPTION: SEQ ID. NO: 5:

| | |
|---|---|
| CTAGATGAGG CAGATATAAG AGTCATGGAA AAAAGGACAG AGAAAAAAAA CAGACAAATC | 60 |
| AGTTGTCAGT ATCCATGGCC TCTGATTCTG TCTCAACCAT GAAACAGAAG TGACACATAT | 120 |
| ACCTGCTAAA AG | 132 |

(2) INFORMATION FOR SEQ ID NO:7:

(i) SEQUENCE CHARACTERISTICS:
        (A) LENGTH: 2038 base pairs
        (B) TYPE: nucleic acid
        (C) STRANDEDNESS:Double
        (D) TOPOLOGY:Linear (ii) MOLECULE TYPE:Genomic DNA (iii) HYPOTHETICAL: No (iv) ANTI-SENSE: No (v) FRAGMENT TYPE: Not applicable (vi) ORIGINAL SOURCE:
        (A) ORGANISM: homo sapiens
        (B) STRAIN: not applicable
        (C) INDIVIDUAL ISOLATE: not applicable
        (D) DEVELOPMENTAL STAGE: not applicable
        (E) HAPLOTYPE: not applicable
        (F) TISSUE TYPE: blood
        (G) CELL TYPE: Luecocyte
        (H) CELL LINE: HeLa
        (I) ORGANELLE: not applicable (vii) IMMEDIATE SOURCE:
        (A) LIBRARY: not applicable
        (B) CLONE: not applicable (viii) POSITION IN GENOME:
        (A) CHROMOSOME/SEGMENT: not applicable
        (B) MAP POSITION: not applicable
        (C) UNITS: not applicable (ix) FEATURE:
        (A) NAME/KEY: This is the DNA sequence
            claimed in 15(vi) as the Cathepsin gene in FIG. 15.
        (B) LOCATION: not available
        (C) IDENTIFICATION METHOD: experiment-
            in specification
        (D) OTHER INFORMATION: prevention of IFN-2
            promoted cell death (x) PUBLICATION INFORMATION: not available (xi) SEQUENCE DESCRIPTION: SEQ ID. NO: 7:

```
GGCTATAAGC GCACGGCCTC GGCGACCCTC TCCGACCCGG CCGCCGCCGC C ATG CAG        57
                                                          Met Gln

CCC TCC AGC CTT CTG CCG CTC GCC CTC TGC CTG CTG GCT GCA CCC GCC       105
Pro Ser Ser Leu Leu Pro Leu Ala Leu Cys Leu Leu Ala Ala Pro Ala
          5                  10                  15

TCC GCG CTC GTC AGG ATC CCG CTG CAC AAG TTC ACG TCC ATC CGC CGG       153
Ser Ala Leu Val Arg Ile Pro Leu His Lys Phe Thr Ser Ile Arg Arg
     20                  25                  30

ACC ATG TCG GAG GTT GGG GGC TCT GTG GAG GAC CTG ATT GCC AAA GGC       201
Thr Met Ser Glu Val Gly Gly Ser Val Glu Asp Leu Ile Ala Lys Gly
 35                  40                  45                  50

CCC GTC TCA AAG TAC TCC CAG GCG GTG CCA GCC GTG ACC GAG GGG CCC       249
Pro Val Ser Lys Tyr Ser Gln Ala Val Pro Ala Val Thr Glu Gly Pro
                 55                  60                  65

ATT CCC GAG GTG CTC AAG AAC TAC ATG GAC GCC CAG TAC TAC GGG GAG       297
Ile Pro Glu Val Leu Lys Asn Tyr Met Asp Ala Gln Tyr Tyr Gly Glu
             70                  75                  80

ATT GGC ATC GGG ACG CCC CCC CAG TGC TTC ACA GTC GTC TTC GAC ACG       345
Ile Gly Ile Gly Trw Pro Pro Gln Cys Phe Thr Val Val Phe Asp Thr
         85                  90                  95

GGC TCC TCC AAC CTG TGG GTC CCC TCC ATC CAC TGC AAA CTG CTG GAC       393
Gly Ser Ser Asn Leu Trp Val Pro Ser Ile His Cys Lys Leu Leu Asp
100                 105                 110

ATC GCT TGC TGG ATC CAC CAC AAG TAC AAC AGC GAC AAG TCC AGC ACC       441
Ile Ala Cys Trp Ile His His Lys Tyr Asn Ser Asp Lys Ser Ser Thr
115                 120                 125                 130

TAC GTG AAG AAT GGT ACC TCG TTT GAC ATC CAC TAT GGC TCG GGC AGC       489
Tyr Val Lys Asn Gly Thr Ser Phe Asp Ile His Tyr Gly Ser Gly Ser
                135                 140                 145

CTC TCC GGG TAC CTG AGC CAG GAC ACT GTG TCG GTG CCC TGC CAG TCA       537
Leu Ser Gly Tyr Leu Ser Gln Asp Thr Val Ser Val Pro Cys Gln Ser
```

-continued

```
                    150                 155                 160
GCG TCG TCA GCC TCT GCC CTG GGC GGT GTC AAA GTG GAG AGG CAG GTC       585
Ala Ser Ser Ala Ser Ala Leu Gly Gly Val Lys Val Glu Arg Gln Val
        165                 170                 175

TTT GGG GAG GCC ACC AAG CAG CCA GGC ATC ACC TTC ATC GCA GCC AAG       633
Phe Gly Glu Ala Thr Lys Gln Pro Gly Ile Thr Phe Ile Ala Ala Lys
180                 185                 190

TTC GAT GGC ATC CTG GGC ATG GCC TAC CCC CGC ATC TCC GTC AAC AAC       681
Phe Asp Gly Ile Leu Gly Met Ala Tyr Pro Arg Ile Ser Val Asn Asn
195                 200                 205                 210

GTG CTG CCC GTC TTC GAC AAC CTG ATG CAG CAG AAG CTG GTG GAC CAG       729
Val Leu Pro Val Phe Asp Asn Leu Met Gln Gln Lys Leu Val Asp Gln
            215                 220                 225

AAC ATC TTC TCC TTC TAC CTG AGC AGG GAC CCA GAT GCG CAG CCT GGG       777
Asn Ile Phe Ser Phe Tyr Leu Ser Arg Asp Pro Asp Ala Gln Pro Gly
        230                 235                 240

GGT GAG CTG ATG CTG GGT GGC ACA GAC TCC AAG TAT TAC AAG GGT TCT       825
Cly Glu Leu Met Leu Gly Gly Thr Asp Ser Lys Tyr Tyr Lys Gly Ser
        245                 250                 255

CTG TCC TAC CTG AAT GTC ACC CGC AAG GCC TAC TGG CAG GTC CAC CTG       873
Leu Ser Tyr Leu Asn Val Thr Arg Lys Ala Tyr Trp Gln Val His Leu
260                 265                 270

GAC CAG GTG GAG GTG GCC AGC GGG CTG ACC CTG TGC AAG GAG GGC TGT       921
Asp Gln Val Glu Val Ala Ser Gly Leu Thr Leu Cys Lys Glu Gly Cys
275                 280                 285                 290

GAG GCC ATT GTG GAC ACA GGC ACT TCC CTC ATG GTG GGC CCG GTG GAT       969
Glu Ala Ile Val Asp Thr Gly Thr Ser Leu Met Val Gly Pro Val Asp
                295                 300                 305

GAG GTG CGC GAG CTG CAG AAG GCC ATC GGG GCC GTG CCG CTG ATT CAG      1017
Glu Val Arg Glu Leu Gln Lys Ala Ile Gly Ala Val Pro Leu Ile Glu
            310                 315                 320

GGC GAG TAC ATG ATC CCC TGT GAG AAG GTG TCC ACC CTG CCC GCG ATC      1065
Gly Glu Tyr Met Ile Pro Cys Glu Lys Val Ser Thr Leu Pro Ala Ile
        325                 330                 335

ACA CTG AAG CTG GGA GGC AAA GGC TAC AAG CTG TCC CCA GAG GAC TAC      1113
Thr Leu Lys Leu Gly Gly Lys Gly Tyr Lys Leu Ser Pro Glu Asp Tyr
        340                 345                 350

ACG CTC AAG GTG TCG CAG GCC GGG AAG ACC CTC TGC CTG AGC GGC TTC      1161
Thr Leu Lys Val Ser Gln Aly Gly Lys Tmr Leu Cys Leu Ser Gly Phe
335                 360                 365                 370

ATG GGC ATG GAC ATC CCG CCA CCC AGC GGG CCA CTC TGG ATC CTG GGC      1209
Met Gly Met Asp Ile Pro Pro Pro Ser Gly Pro Leu Trp Ile Leu Gly
                375                 380                 385

GAC GTC TTC ATC GGC CGC TAC TAC ACT GTG TTT GAC CGT GAC AAC AAC      1257
Asp Val Phe Ile Gly Arg Tyr Tyr Thr Val Pme Asp Arg Asp Asn Asn
            390                 395                 400

AGG GTG GGC TTC GCC GAG GCT GCC CGC CTC TAGTTCCCAA GGCGTCCGCG        1307
Arg Val Gly Phe Ala Glu Ala Ala Arg Leu
        405                 410

CGCCAGCACA GAAACAGAGG AGAGTCCCAG AGCAGGAGGC CCCTGGCCCA GCGGCCCCTC   1367

CCACACACAC CCACACACTC GCCCGCCCAC TGTCCTGGGC GCCCTGGAAG CCGGCGGCCC   1427

AAGCCCGACT TGCTGTTTTG TTCTGTGGTT TTCCCCTCCC TGGGTTCAGA AATGCTGCCT   1487

GCCTGTCTGT CTCTCCATCT GTTTGGTGGG GGTAGAGCTG ATCCAGAGCA CAGATCTGTT   1547

TCGTGCATTG GAAGACCCCA CCCAAGCTTG GCAGCCGAGC TCGTGTATCC  TGGGGCTCCC  1607

TTCATCTCCA GGGAGTCCCC TCCCCGGCCC TACCAGCGCC CGCTGGGCTG AGCCCCTACC   1667

CCACACCAGG CCGTCCTCCC GGGCCCTCCC TTGGAAACCT GCCCTGCCTG AGGGCCCCTC   1727
```

```
TGCCCAGCTT GGGCCCAGCT GGGCTCTGCC ACCCTACCTG TTCAGTGTCC CGGGCCCGTT    1787

GAGGATGAGG CCGCTAGAGG CCTGAGGATG AGCTGGAAGG AGTGAGAGGG GACAAAACCC    1847

ACCTTGTTGG AGCCTGCAGG GTGGTGCTGG GACTGAGCCA GTCCCAGGGG CATGTATTGG    1907

CCTGGAGGTG GGGTTGGGAT TGGGGGCTGG TGCCAGCCTT CCTCTGCAGC TGACCTCTGT    1967

TGTCCTCCCC TTGGGCGGCT GAGAGCCCCA GCTGACATGG AAATACAGTT GTTGGCCTCC    2027

GGCCTCCCCT C                                                        2038
```

(2) INFORMATION FOR SEQ ID NO:8:

(i) SEQUENCE CHARACTERISTICS:
        (A) LENGTH: 3829 base pair
        (B) TYPE: nucleic acid
        (C) STRANDEDNESS: double
        (D) TOPOLOGY: linear (ii) MOLECULE TYPE: Genomic DNA (iii) HYPOTHETICAL: No (iv) ANTI-SENSE: No (v) FRAGMENT TYPE: not applicable (vi) ORIGINAL SOURCE:
        (A) ORGANISM: homo sapiens
        (B) STRAIN: not applicable
        (C) INDIVIDUAL ISOLATE: not applicable
        (D) DEVELOPMENTAL STAGE: not applicable
        (E) HAPLOTYPE: not applicable
        (F) TISSUE TYPE: blood
        (G) CELL TYPE: leucocyte
        (H) CELL LINE: HeLa
        (I) ORGANELLE: not applicable (vii) IMMEDIATE SOURCE:
        (A) LIBRARY: not applicable
        (B) CLONE: not applicable (viii) POSITION IN GENOME:
        (A) CHROMOSOME/SEGMENT: not applicable
        (B) MAP POSITION: not applicable
        (C) UNITS: not applicable (ix) FEATURE:
        (A) NAME/KEY: SEQ ID. NO:8 is the sequence
            in claim 1(vi) starting at triplet in position 201-203
            and ending at the triplet 3018-3020
        (B) LOCATION: not available
        (C) IDENTIFICATION METHOD: experiment-
            in specification
        (D) OTHER INFORMATION: prevention of IFN- -induced
            programmed cell death (x) PUBLICATION INFORMATION: not available (xi) SEQUENCE DESCRIPTION: SEQ ID. NO: 8:

```
GAATTCCGCT CTATGGAGGT GGCAGCGGGT ACCGAGTGGC GGCTGCAGCA GCGACTCCTC    60

TGAGCTGAGT TTGAGGCCGT CCCCGACTCC TTCCTCCCCC TTCCCTCCCC CTTTTTTTTG    120

TTTTCCGTTC CCCTTTCCCC TCCCTTCCCT ATCCCCGACG ACCGGATCCT GAGGAGGGCA    180

GCTGCGGTGG CAGCTGCTGA GTT CTC GGT GAA GGT ATT TCA TTT CTC CTG TCC    233
                     Val Leu Gly Glu Gly Ile Ser Phe Leu Leu Ser
                                      5                  10

CCT CCC CTC CCC ACC CCA TCT ATT AAT ATT ATT CTT TTG AAG ATT CTT     281
Pro Pro Leu Pro Thr Pro Ser Ile Asn Ile Ile Leu Leu Lys Ile Leu
             15                  20                  25

CGT TGT CAA GCC GCC AAA GTG GAG AGT GCG ATT GCA GAA GGG GGT GCT     329
Arg Cys Gln Ala Ala Lys Val Glu Ser Ala Ile Ala Glu Gly Gly Ala
         30                  35                  40
```

```
TCT CGT TTC AGT GCT TCT TCG GGC GGA GGA GGA AGT AGG GGT GCA CCT      377
Ser Arg Phe Ser Ala Ser Ser Gly Gly Gly Gly Ser Arg Gly Ala Pro
    45                  50                  55

CAG CAC TAT CCC AAG ACT GCT GGC AAC AGC GAG TTC CTG GGG AAA ACC      425
Gln His Tyr Pro Lys Thr Ala Gly Asn Ser Glu Phe Leu Gly Lys Thr
60                  65                  70                  75

CCA GGG CAA AAC GCT CAG AAA TGG ATT CCT GCA CGA AGC ACT AGA CGA      473
Pro Gly Gln Asn Ala Gln Lys Trp Ile Pro Ala Arg Ser Thr Arg Arg
                75                  80                  85

GAT GAC AAC TCC GCA GCA AAC AAC TCC GCA AAC GAA AAA GAA CGA CAT      521
Asp Asp Asn Ser Ala Ala Asn Asn Ser Ala Asn Glu Lys Glu Arg His
            90                  95                  100

GAT GCA ATC TTC AGG AAA GTA AGA GGC ATA CTA AAT AAG CTT ACT CCT      569
Asp Ala Ile Phe Arg Lys Val Arg Gly Ile Leu Asn Lys Leu Thr Pro
        105                 110                 115

GAA AAG TTT GAC AAG CTA TGC CTT GAG CTC CTC AAT GTG GGT GTA GAG      617
Glu Lys Phe Asp Lys Leu Cys Leu Glu Leu Leu Asn Val Gly Val Glu
120                 125                 130

TCT AAA CTC ATC CTT AAA GGG GTC ATA CTG CTG ATT GTG GAC AAA GCC      665
Ser Lys Leu Ile Leu Lys Gly Val Ile Leu Leu Ile Val Asp Lys Ala
135                 140                 145                 150

CTA GAA GAG CCA AAG TAT AGC TCA CTG TAT GCT CAG CTA TGT CTG CGA      713
Leu Glu Glu Pro Lys Tyr Ser Ser Leu Tyr Ala Gln Leu Cys Leu Arg
                155                 160                 165

TTG GCA GAA GAT GCA CCA AAC TTT GAT GGC CCA GCA GCA GAG GGT CAA      761
Leu Ala Glu Asp Ala Pro Asn Phe Asp Gly Pro Ala Ala Glu Gly Gln
            170                 175                 180

CCA GGA CAG AAG CAA AGC ACC ACA TTC AGA CGC CTC CTA ATT TCC AAA      809
Pro Gly Gln Lys Gln Ser Thr Thr Phe Arg Arg Leu Leu Ile Ser Lys
        185                 190                 195

TTA CAA GAT GAA TTT GAA AAC CGA ACT AGA AAT GTT GAT GTC TAT GAT      857
Leu Gln Asp Glu Phe Glu Asn Arg Thr Arg Asn Val Asp Val Tyr Asp
200                 205                 210

AAG CGT GAA AAT CCC CTC CTC CCC GAG GAG GAG GAA CAG AGA GCC ATT      905
Lys Arg Glu Asn Pro Leu Leu Pro Glu Glu Glu Glu Gln Arg Ala Ile
220                 225                 230                 235

GCT AAG ATC AAG ATG TTG GGA AAC ATC AAA TTC ATT GGA GAG CTT GGC      953
Ala Lys Ile Lys Met Leu Gly Asn Ile Lys Phe Ile Gly Glu Leu Gly
                240                 245                 250

AAG CTT GAT CTT ATT CAC GAA TCT ATC CTT CAT AAG TGC ATC AAA ACA     1001
Lys Leu Asp Leu Ile His Glu Ser Ile Leu His Lys Cys Ile Lys Thr
            255                 260                 265

CTT TTG GAA AAG AAG AAG AGA GTC CAA CTC AAA GAT ATG GGA GAG GAT     1049
Leu Leu Glu Lys Lys Lys Arg Val Gln Leu Lys Asp Met Gly Glu Asp
        270                 275                 280

TTG GAG TGC CTC TGT CAG ATA ATG AGG ACA GTG GGA CCT AGA TTA GAC     1097
Leu Glu Cys Leu Cys Gln Ile Met Arg Thr Val Gly Pro Arg Leu Asp
285                 290                 295

CAT GAA CGA GCC AAG TCC TTA ATG GAT CAG TAC TTT GCC CGA ATG TGC     1145
His Glu Arg Ala Lys Ser Leu Met Asp Gln Tyr Phe Ala Arg Met Cys
300                 305                 310                 315

TCC TTG ATG TTA AGT AAG GAA TTG CCA GCA AGG ATT CGT TTC CTG CTG     1193
Ser Leu Met Leu Ser Lys Glu Leu Pro Ala Arg Ile Arg Phe Leu Leu
                320                 325                 330

CAG GAT ACC GTA GAG TTG CGA GAA CAC CAT TGG GTT CCT CGC AAG GCT     1241
Gln Asp Thr Val Glu Leu Arg Glu His His Trp Val Pro Arg Lys Ala
            335                 340                 345

TTT CTT GAC AAT GGA CCA AAG ACG ATC AAT CAA ATT CGT CAA GAT GCA     1289
Phe Leu Asp Asn Gly Pro Lys Thr Ile Asn Gln Ile Arg Gln Asp Ala
        350                 355                 360
```

-continued

| | | |
|---|---|---|
| GTA AAA GAT CTA GGG GTG TTT ATT CCT GCT CCT ATG GCT CAA GGG ATG<br>Val Lys Asp Leu Gly Val Phe Ile Pro Ala Pro Met Ala Gln Gly Met<br>365                                    370                          375 | 1337 |
| AGA AGT GAC TTC TTT CTG GAG GGA CCG TTC ATG CCA CCC AGG ATG AAA<br>Arg Ser Asp Phe Phe Leu Glu Gly Pro Phe Met Pro Pro Arg Met Lys<br>380                                    385                          390                          395 | 1385 |
| ATG GAT AGG GAC CCA CTT GGA GGA CTT GCT GAT ATG TTT GGA CAA ATG<br>Met Asp Arg Asp Pro Leu Gly Gly Leu Ala Asp Met Phe Gly Gln Met<br>                          400                                405                              410 | 1433 |
| CCA GGT AGC GGA ATT GGT ACT GGT CCA GGA GTT ATC CAG GAT AGA TTT<br>Pro Gly Ser Gly Ile Gly Thr Gly Pro Gly Val Ile Gln Asp Arg Phe<br>                        415                                420                          425 | 1481 |
| TCA CCC ACC ATG GGA CGT CAT CGT TCA AAT CAA CTC TTC AAT GGC CAT<br>Ser Pro Thr Met Gly Arg His Arg Ser Asn Gln Leu Phe Asn Gly His<br>              430                                435                                440 | 1529 |
| GGG GGA CAC ATC ATG CCT CCC ACA CAA TCG CAG TTT GGA GAG ATG GGA<br>Gly Gly His Ile Met Pro Pro Thr Gln Ser Gln Phe Gly Glu Met Gly<br>              445                                450                                455 | 1577 |
| GGC AAG TTT ATG AAA AGC CAG GGG CTA AGC CAG CTC TAC CAT AAC CAG<br>Gly Lys Phe Met Lys Ser Gln Gly Leu Ser Gln Leu Tyr His Asn Gln<br>460                                    465                          470                          475 | 1625 |
| AGT CAG GGA CTC TTA TCC CAG CTG CAA GGA CAG TCG AAG GAT ATG CCA<br>Ser Gln Gly Leu Leu Ser Gln Leu Gln Gly Gln Ser Lys Asp Met Pro<br>                          480                                485                              490 | 1673 |
| CCT CGG TTT TCT AAG AAA GGA CAG CTT AAT GCA GAT GAG ATT AGC CTG<br>Pro Arg Phe Ser Lys Lys Gly Gln Leu Asn Ala Asp Glu Ile Ser Leu<br>                        495                                500                          505 | 1721 |
| AGG CCT GCT CAG TCG TTC CTA ATG AAT AAA AAT CAA GTG CCA AAG CTT<br>Arg Pro Ala Gln Ser Phe Leu Met Asn Lys Asn Gln Val Pro Lys Leu<br>              510                                515                                520 | 1769 |
| CAG CCC CAG ATA ACT ATG ATT CCT CCT AGT GCA CAA CCA CCA CGC ACT<br>Gln Pro Gln Ile Thr Met Ile Pro Pro Ser Ala Gln Pro Pro Arg Thr<br>525                                    530                          535 | 1817 |
| CAA ACA CCA CCT CTG GGA CAG ACA CCT CAG CTT GGT CTC AAA ACT AAT<br>Gln Thr Pro Pro Leu Gly Gln Thr Pro Gln Leu Gly Leu Lys Thr Asn<br>540                                    545                          550                          555 | 1865 |
| CCA CCA CTT ATC CAG GAA AAG CCT GCC AAG ACC AGC AAA AAG CCA CCA<br>Pro Pro Leu Ile Gln Glu Lys Pro Ala Lys Thr Ser Lys Lys Pro Pro<br>                        560                                565                              570 | 1913 |
| CCG TCA AAG GAA GAA CTC CTT AAA CTA ACT GAA ACT GTT GTG ACT GAA<br>Pro Ser Lys Glu Glu Leu Leu Lys Leu Thr Glu Thr Val Val Thr Glu<br>              575                                580                                585 | 1961 |
| TAT CTA AAT AGT GGA AAT GCA AAT GAG GCT GTC AAT GGT GTA AGA GAA<br>Tyr Leu Asn Ser Gly Asn Ala Asn Glu Ala Val Asn Gly Val Arg Glu<br>              590                                595                                600 | 2009 |
| ATG AGG GCT CCT AAA CAC TTT CTT CCT GAG ATG TTA AGC AAA GTA ATC<br>Met Arg Ala Pro Lys His Phe Leu Pro Glu Met Leu Ser Lys Val Ile<br>605                                    610                          615 | 2057 |
| ATC CTG TCA CTA GAT AGA AGC GAT GAA GAT AAA GAA AAA GCA AGT TCT<br>Ile Leu Ser Leu Asp Arg Ser Asp Glu Asp Lys Glu Lys Ala Ser Ser<br>620                                    625                          630                          635 | 2105 |
| TTG ATC AGT TTA CTC AAA CAG GAA GGG ATA GCC ACA AGT GAC AAC TTC<br>Leu Ile Ser Leu Leu Lys Gln Glu Gly Ile Ala Thr Ser Asp Asn Phe<br>                        640                                645                              650 | 2153 |
| ATG CAG GCT TTC CTG AAT GTA TTG GAC CAG TGT CCC AAA CTG GAG GTT<br>Met Gln Ala Phe Leu Asn Val Leu Asp Gln Cys Pro Lys Leu Glu Val<br>                        655                                660                          665 | 2201 |
| GAC ATC CCT TTG GTG AAA TCC TAT TTA GCA CAG TTT GCA GCT CGT GCC<br>Asp Ile Pro Leu Val Lys Ser Tyr Leu Ala Gln Phe Ala Ala Arg Ala<br>                        670                                675                          680 | 2249 |

| | | |
|---|---|---|
| ATC ATT TCA GAG CTG GTG AGC ATT TCA GAA CTA GCT CAA CCA CTA GAA<br>Ile Ile Ser Glu Leu Val Ser Ile Ser Glu Leu Ala Gln Pro Leu Glu<br>685                   690                   695 | 2297 |
| AGT GGC ACC CAT TTT CCT CTC TTC CTA CTT TGT CTT CAG CAG TTA GCT<br>Ser Gly Thr His Phe Pro Leu Phe Leu Leu Cys Leu Gln Gln Leu Ala<br>700                   705                   710                   715 | 2345 |
| AAA TTA CAA GAT CGA GAA TGG TTA ACA GAA CTT TTT CAA CAA AGC AAG<br>Lys Leu Gln Asp Arg Glu Trp Leu Thr Glu Leu Phe Gln Gln Ser Lys<br>                   720                   725                   730 | 2393 |
| GTC AAT ATG CAG AAA ATG CTC CCA GAA ATT GAT CAG AAT AAG GAC CGC<br>Val Asn Met Gln Lys Met Leu Pro Glu Ile Asp Gln Asn Lys Asp Arg<br>             735                   740                   745 | 2441 |
| ATG TTG GAG ATT TTG GAA GGA AAG GGA CTG AGT TTC TTA TTC CCA CTC<br>Met Leu Glu Ile Leu Glu Gly Lys Gly Leu Ser Phe Leu Phe Pro Leu<br>750                   755                   760 | 2489 |
| CTC AAA TTG GAG AAG GAA CTG TTG AAG CAA ATA AAG TTG GAT CCA TCC<br>Leu Lys Leu Glu Lys Glu Leu Leu Lys Gln Ile Lys Leu Asp Pro Ser<br>765                   770                   775 | 2537 |
| CCT CAA ACC ATA TAT AAA TGG ATT AAA GAT AAC ATC TCT CCC AAA CTT<br>Pro Gln Thr Ile Tyr Lys Trp Ile Lys Asp Asn Ile Ser Pro Lys Leu<br>780                   785                   790                   795 | 2585 |
| CAT GTA GAT AAA GGA TTT GTG AAC ATC TTA ATG ACT AGC TTC TTA CAG<br>His Val Asp Lys Gly Phe Val Asn Ile Leu Met Thr Ser Phe Leu Gln<br>             800                   805                   810 | 2633 |
| TAC ATT TCT AGT GAA GTA AAC CCC CCC AGC GAT GAA ACA GAT TCA TCC<br>Tyr Ile Ser Ser Glu Val Asn Pro Pro Ser Asp Glu Thr Asp Ser Ser<br>815                   820                   825 | 2681 |
| TCT GCT CCT TCC AAA GAA CAG TTA GAG CAG GAA AAA CAA CTA CTA CTA<br>Ser Ala Pro Ser Lys Glu Gln Leu Glu Gln Glu Lys Gln Leu Leu Leu<br>830                   835                   840 | 2729 |
| TCT TTC AAG CCA GTA ATG CAG AAA TTT CTT CAT GAT CAC GTT GAT CTA<br>Ser Phe Lys Pro Val Met Gln Lys Phe Leu His Asp His Val Asp Leu<br>845                   850                   855 | 2777 |
| CAA GTC AGT GCC CTG TAT GCT CTC CAG GTG CAC TGC TAT AAC AGC AAC<br>Gln Val Ser Ala Leu Tyr Ala Leu Gln Val His Cys Tyr Asn Ser Asn<br>860                   865                   870                   875 | 2825 |
| TTC CCA AAA GGC ATG TTA CTT CGC TTT TTT GTG CAC TTC TAT GAC ATG<br>Phe Pro Lys Gly Met Leu Leu Arg Phe Phe Val His Phe Tyr Asp Met<br>             880                   885                   890 | 2873 |
| GAA ATT ATT GAA GAA GAA GCT TTC TTG GCT TGG AAA GAA GAT ATA ACC<br>Glu Ile Ile Glu Glu Glu Ala Phe Leu Ala Trp Lys Glu Asp Ile Thr<br>                   895                   900                   905 | 2921 |
| CAA GAG TTT CCG GGA AAA GGC AAG GCT TTG TTC CAG GTG AAT CAG TGG<br>Gln Glu Phe Pro Gly Lys Gly Lys Ala Leu Phe Gln Val Asn Gln Trp<br>             910                   915                   920 | 2969 |
| CTA ACC TGG TTA GAA ACT GCT GAA GAA GAA GAA TCA GAG GAA GAA GCT<br>Leu Thr Trp Leu Glu Thr Ala Glu Glu Glu Glu Ser Glu Glu Glu Ala<br>925                   930                   935 | 3017 |
| GAC TAAAGAACCA GCCAAAGCCT TAAATTGTGC AAAACATACT GTTGCTATGA<br>Asp<br>940 | 3070 |
| TGTAACTGCA TTTGACCTAA CCACTGCGAA AATTCATTCC GCTGTAATGT TTCACAATA | 3130 |
| TTTAAAGCAG AAGCACGTCA GTTAGGATTT CCTTCTGCAT AAGGTTTTTT TGTAGTGTAA | 3190 |
| TGTCTTAATC ATAGTCTACC ATCAAATATT TTAGGAGTAT CTTTAATGTT TAGATAGTAT | 3250 |
| ATTAGCAGCA TGCAATAATT ACATCATAAG TTCTCAAGCA GAGGCAGTCT ATTGCAAGGA | 3310 |
| CCTTCTTTGC TGCCAGTTAT CATAGGCTGT TTTAAGCTAG AAAACTGAAT AGCAACACTG | 3370 |
| AATACTGTAG AAATGCACTT TGCTCAGTAA TACTTGAGTT GTTGCAATAT TTGATTATCC | 3430 |

```
ATTTGGTTGT TACAGAAAAA TTCTTAACTG TAATTGATGG TTGTTGCCGT AATAGTATAT    3490

TGCCTGTATT TCTACCTCTA GTAATGGGCT TTATGTGCTA GATTTTAATA TCCTTGAGCC    3550

TGGGCAAGTG CACAAGTCTT TTTAAAAGAA ACATGGTTTA CTTGCACAAA ACTGATCAGT    3610

TTTGAGAGAT CGTTAATGCC CTTGAAGTGG TTTTTGTGGG TGTGAAACAA ATGGTGAGAA    3670

TTTGAATTGG TCCCTCCTAT TATAGTATTG AAATTAAGTC TACTTAATTT ATCAAGTCAT    3730

GTTCATGCCC TGATTTTATA TACTTGTATC TATCAATAAA CATTGTGATA CTTGAAAAAA    3790

AAAAAAAAAA AAAAAAAAA AAAAAAAAA AGGGAATTC                             3829
```